US008518675B2

(12) United States Patent
DiCosimo et al.

(10) Patent No.: US 8,518,675 B2
(45) Date of Patent: *Aug. 27, 2013

(54) PRODUCTION OF PERACIDS USING AN ENZYME HAVING PERHYDROLYSIS ACTIVITY

(75) Inventors: Robert DiCosimo, Chadds Ford, PA (US); John E. Gavagan, Wilmington, DE (US); Mark S. Payne, Wilmington, DE (US); Frederick B. Cooling, III, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 134 days.

This patent is subject to a terminal disclaimer.

(21) Appl. No.: 11/943,872

(22) Filed: Nov. 21, 2007

(65) Prior Publication Data
US 2008/0176299 A1    Jul. 24, 2008

Related U.S. Application Data

(63) Continuation-in-part of application No. 11/743,354, filed on May 2, 2007, now Pat. No. 7,951,566, which is a continuation-in-part of application No. 11/638,635, filed on Dec. 12, 2006, now Pat. No. 7,964,378.

(60) Provisional application No. 60/750,092, filed on Dec. 13, 2005, provisional application No. 60/853,065, filed on Oct. 20, 2006.

(51) Int. Cl.
*C12P 7/40* (2006.01)
*C12N 9/14* (2006.01)

(52) U.S. Cl.
USPC .......................................... 435/136; 435/197

(58) Field of Classification Search
None
See application file for complete search history.

(56) References Cited

U.S. PATENT DOCUMENTS

| | | | |
|---|---|---|---|
| 3,974,082 A | 8/1976 | Weyn | |
| 4,444,886 A | 4/1984 | Esders et al. | |
| 4,585,150 A | 4/1986 | Beacham et al. | |
| 5,108,457 A * | 4/1992 | Poulose et al. | 8/111 |
| 5,116,575 A | 5/1992 | Badertscher et al. | |
| 5,281,525 A | 1/1994 | Mitsushima et al. | |
| 5,296,161 A | 3/1994 | Wiersema et al. | |
| 5,338,676 A | 8/1994 | Mitsushima et al. | |
| 5,364,554 A | 11/1994 | Stanislowski et al. | |
| 5,398,846 A | 3/1995 | Corba et al. | |
| 5,528,152 A | 6/1996 | Hinoshita et al. | |
| 5,624,634 A | 4/1997 | Brougham et al. | |
| 5,683,724 A | 11/1997 | Hei et al. | |
| 5,932,532 A | 8/1999 | Ghosh et al. | |
| 6,183,807 B1 | 2/2001 | Gutsmann et al. | |
| 6,210,639 B1 | 4/2001 | Vlass et al. | |
| 6,319,888 B2 | 11/2001 | Wei et al. | |
| 6,391,840 B1 | 5/2002 | Thompson et al. | |
| 6,465,233 B1 | 10/2002 | Knauseder et al. | |
| 6,518,307 B2 | 2/2003 | McKenzie et al. | |
| 6,545,047 B2 | 4/2003 | Gutsmann et al. | |
| 6,645,233 B1 | 11/2003 | Ayers et al. | |
| 6,995,125 B2 | 2/2006 | Dasque et al. | |
| 7,384,787 B2 * | 6/2008 | Kazlauskas et al. | 435/440 |
| 2003/0026846 A1 | 2/2003 | Hei et al. | |
| 2005/0008526 A1 | 1/2005 | Bianchetti et al. | |
| 2005/0139608 A1 | 6/2005 | Muehlhausen et al. | |

FOREIGN PATENT DOCUMENTS

| | | |
|---|---|---|
| EP | 0807156 B1 | 3/2001 |
| WO | WO 99/03984 A2 | 1/1999 |
| WO | WO 00/11713 A1 | 3/2000 |
| WO | WO 2004/058961 A1 | 7/2004 |
| WO | WO2007/070609 A2 | 6/2007 |
| WO | WO2008/073139 A1 | 6/2008 |

OTHER PUBLICATIONS

Chica et al. (Curr Opin Biotechnol. Aug. 2005;16(4):378-84.*
Witkowski et al. (Biochemistry. Sep. 7, 1999; 38(36): 11643-50.*
Seffernick et al. (J Bacteriol. Apr. 2001; 183 (8): 2405-10.*
Vincent et al. J. Mol. Biol. 2003, 330, pp. 593-606.*
Mitsushima et al UniportKB accession No. Q59233, Nov. 1, 1996.*
Guo et al., PNAS, 2004, vol. 101 (25): 9205-9210.*
Copeland A. et al., "Thermotoga Lettingae Acetyl Xylan Esterase", A8F440_THELT, XP002501372, Nov. 13, 2007.
Corresponding PCT/US2008/067712 International Search Report and Written Opinion dated Jan. 16, 2009.
Vincent et al, J. Mol. Biol. 330:593-606 (2003).
U.S. Appl. No. 11/413,246, filed Apr. 28, 2006, Robert DiCosimo et al.
U.S. Appl. No. 11/588,523, filed Oct. 27, 2006, Robert DiCosimo et al.
Daneil Swerm, Organic Peroxides, vol. 1:313-516, John Wiley & Sons Inc. (Book Not Included), 1989.
O. Kirk et. al., Enzyme Catalyzed Degradation and Formation of Peroxycarboxlic Acids, Biocatalysis, 1994, vol. 11:65-77.
Lennon et. al., The I.M.A.G.E. Consortium; An Intergrated Molecular Analysis of Genomes and Their Expression, Genomics, 1996, vol. 33:151-152.
Mitsushima et. al., Gene Cloning, Nucleotide Sequence, and Expression of a Cephalosporin-C Deacetylase From *Bacillus subtilis*, Appl. Environ. Microbiol., 1995, vol. 61:2224-2229.
Vincent et. al., Multifunctional Xylooligosaccharide/Cephalosporin C Deacetylase revealed by the Hexameric Structure of the *Bacillus subtilis* Enzyme at 1.9 A Resolution, J. Mol. Biol., 2003, vol. 330:593-606.
Gordon F. Bickerstaff, Immobilization of Enzymes and Cells, 1997 (Book not included).
National Center for Biotechnology Information General Identifier No. 550075, Feb. 3, 1999, K. Mitsushima et. al., Gene Cloning, Nucleotide Seuqnce, and Expression of a Cephalosporin-C Deacetylase From *Bacillus* Subtiles, Accession No. BAA01729, 1999.

(Continued)

*Primary Examiner* — Tekchand Saidha
*Assistant Examiner* — Md. Younus Meah

(57) ABSTRACT

A process is provided for producing peroxycarboxylic acids from carboxylic acid esters. More specifically, carboxylic acid esters are reacted with an inorganic peroxide, such as hydrogen peroxide, in the presence of an enzyme catalyst having perhydrolysis activity. The present perhydrolase catalysts are classified as members of the carbohydrate esterase family 7 (CE-7) based on the conserved structural features. Further, disinfectant formulations comprising the peracids produced by the processes described herein are provided.

6 Claims, 3 Drawing Sheets

(56) References Cited

OTHER PUBLICATIONS

Payne et. al., Use of Alkaline Phosphatase Fusions to Study Protein Secretion in *Bacillus subtilis*, J. Bacteriol., 1991, vol. 173:2278-2282.

Sambrook et. al., Molecular Cloning: A Laboratory Manual, 2001, Third Edition, Cold Spring Harbor Laboratory Press (Book Not Included).

A. M. Lesk, Computational Molecular Biology, 1988, Oxford University Press (Book Not Included).

D. W. Smith, Biocomputing: Informatics and Genome Projects, 1993, Academic Press (Book Not Included).

Griffin et. al., Computer Analysis of Sequence Data, Part 1, 1994, Human Press (Book Not Included).

G. Von Heinje, Sequence Analysis in Molecular Biology, 1987, Academic Press (Book Not Included).

M. Gribskov et. al., Sequence Analysis Primer, 1991, Stockton Press (Book Not Included).

Higgins et. al., Fast and Sensitive Multiple Sequence Alignments on a Microcomputer, Cabios, 1989, vol. 5:151-153.

Altschul et. al., Basic Local Aliignment Search Tool, J. Mol. Biol., 1990, vol. 215:403-410.

Pearson, Searching Protein Sequence Databases Is Optimal Best?, Comput. Methods Genome Res., 1994, Meeting Date 1992, pp. 111-120.

Bickerstaff, Immobilization of Enzymes and Cells, 1997, Human Press (Book Not Included).

Karst et. al., Simultaneous HPLC Determination of Peroxyacetic Acid and Hydrogen Peroxide, Anal. Chem., 1997, vol. 69:3623-3627.

Minning et. al., Determination of Peracid and Putative Enzymatic Peracid Formation by an Easy Colorimetric Assay,Analytica Chimica Acta, 1999, vol. 378:293-298.

Gabrielson et. al., Evaluation of Redox Indicators and the Use of Digital Scanners and Spectrophotometer for Quantification of Microbial Growth in Microplates, J. Microbial. Methods, 2002, vol. 50:63-73.

Brock, Disinfection, Sterilization, and Preservation, 2001, 5$^{th}$ Edition, Lippincott Williams & Wilkins (Book Not Included).

Abbott et. al., Physical Properties and Kinetic Behavior of a Cephalosporin Acetylesterase Produced by *Bacillus* Subtiles, Appl. Microbiol., 1975, vol. 30:413-419.

Politino et. al., Purification and Characterization of a Cephalosporin Esterase From Rhodospridium Toruloides, Appl. Environ. Microbiol., 1997, vol. 63:4807-4811.

Sakai et. al., Purification and Properties of Cephalosporin-C Deacetylase From the Yeast, Rhodotorula Glutinis 38B1, Useful for Bioconversion of 7-Aminocephalosporanic Acid Derivatives, Ferment Bioeng., 1998, vol. 85:53-57.

Lorenz et. al., Isolation, Analysis, and Expression of Two Genes From *Thermoanaerobacterium* Sp. Strain JW/SL YS485: A B-Xylosidase and a Novel Acetyl Xylan Esterase With Cephalosporin C Deacetylase Activity, J. Bacteriol., 1997, vol. 179:5436-5441.

Cardoza et. al., A Cephalosporin C Acetlhydrolase Is Present in the Cultures of *Nocardia* Lactamdurans, Appl. Microbiol. Biotechnol., 2000, vol. 54:406-412.

Takami et. al., Complete Genome Sequence of the Alkaliphilic Bacterium *Bacillus* Halodurans and Genomic Sequence Comparison With *Bacillus* Subtiles, NAR, 2000, vol. 28:4317-4331.

Rey et. al., Complete Genome Sequence of the Industrial Bacterium *Bacillus licheniformis* and Comparisons With Closely Related *Bacillus* Species, Genome Biol., 2004, vol. 5: Article 77, pp. 1-12.

Degrassi et. al., The Acetyl Xylan Esterase of *Bacillus pumilus* Belongs to a Family of Esterases With Broad Substrate Specificity, Microbiology, 2000, vol. 146:1585-1591.

Brock, Biotechnology: A Tectbook of Industiral Microbiology, 1989, 2nd Edition (Book Not Included).

Deshpande et. al., Ethanol Production From Cellulose by Coupled Saccharification/Fermentation Using Saccharomyces Cerevisiae and Cellulase Complex From *Sclerotium rolfsii* UV-8, Mutant, Appl. Biochem. Biotechnol., 1992, vol. 36:227-234.

Sulter et. al., Proliferation and Metabolic Significance of Peroxisomes in *Candida boidinii* During Growth on D-Alanine or Oleic Acid as the Sole Carbon Source, Arch. Microbiol., 1990, vol. 153:485-489.

National Center for Biotechnology Information General Identifier No. 2429094, Sep. 23, 2002, D.A. Yernool et. al., Molecular and Functional Characterization of a Xylan Catabolic Cluster and Associated ABC Transporter System From the Hypothermophile Thermotoga Neapolitana, Accession No. AAB70869.

National Center for Biotechnology Information General Identifier No. 58632, Apr. 18, 2005, M. Tavazza et. al., Nucleotide Sequence, Genomic Organization and Synthesis of Infectious Transcripts From a Full-Length Clone of Artichoke Mottle Crinkle Virus, Accession No. CAA44355.

National Center for Biotechnology Information General Identifier No. 58219088, G. Degrassi et. al., The Acetyl Xylan Esterase of *Bacillus pumilus* Belongs to a Family of Esterases With Broad Substrate Specificity, Accession No. AJ249957, 2000.

Rice et. al., Emboss: The European Molecular Biology Open Software Suite, Trends in Genetics, 2000, vol. 16:276-277.

Chenna et. al., Multiple Sequence Alignment With the Clustal Series of Programs, Nucleic Acids Res., Nucleic Acids Res., 2003, vol. 31:3497-3500.

Needleman et. al., A General Method Applicable to the Search for Similarities in the Amino Acid Sequence of Two Proteins, J. Mol. Biol., 1970, vol. 48:443-453.

Smith-Waterman, Identification of Common Molecular Subsequences, J. Mol. Biol., 1981, vol. 147:195-197.

Thompson et. al., Clustal W: Improving the Sensitivity of Progressive Multiple Sequence Alignment Through Sequence Weighting, Position-Specific Gap Penalties and Weight Matrix Choice, Nucleic Acids Research, 1994, vol. 22:4673-4680.

Datsenko et. al., One-Step Inactivation of Chromosomal Genes in *Escherichia coli* K-12 Using PCR Products, PNAS, 2000, vol. 97:6640-6645.

* cited by examiner

| | |
|---|---|
| SEQ ID NO:2  | -MQLFDLPLDQLQTYKPEKTAPKDFSEFWKLSLEELAKVQAEPDLQPVDYPADGVKVYRL |
| SEQ ID NO:6  | -MQLFDLPLDQLQTYKPEKTAPKDFSEFWKLSLEELAKVQAEPDLQPVDYPADGVKVYRL |
| SEQ ID NO:8  | -MQLFDLPLDQLQTYKPEKTTPNDFSEFWKSSLDELAKVKAAPDLQLVDYPADGVKVYRL |
| SEQ ID NO:10 | MQQPYDMPLEQLYQYKPERTAPADFKEFWKGSLEELANEKAGPQLEPHEYPADGVKVYWL |
| SEQ ID NO:12 | -MQLFDLSLEELKKYKPKKTARPDFSDFWKKSLEELRQVEAEPTLESYDPVKGVKVYRL |
| SEQ ID NO:14 | MAQLYDMPLEELKKYKPALTKQKDFDEFWEKSLKELAETIPLKYQLIPYDFPARRVKVFRV |
| SEQ ID NO:16 | -MAFFDMPLEELKKYRPERYEEKDFDEFWRETLKESEGFPLDPVFEKVDFHLKTVETYDV |
| SEQ ID NO:18 | -MAFFDLPLEELKKYRPERYEEKDFDEFWEETLAESEKFPLDPVFERMESHLKTVEAYDV |
| SEQ ID NO:26 | -MPLVDMPLRELLAYEGINPKPADFDQYWNRAKTEIEAIDPEVTLVESSFQCSFANCYHF |
| SEQ ID NO:32 | -MQLFDLPLDQLQTYKPEKTAPKDFSEFWKLSIEELAKVQAEPDLQPVDYPADGVKVYRL |
| SEQ ID NO:70 | -MGLFDMPLQKLREYTGTNPCPEDFDEYWDRALDEMRSVDPKIKMKKSSFQVPFAECYDL |
| | * :*  * :* .   .   *       :    :        .      :: . |

| | |
|---|---|
| SEQ ID NO:2  | TYKSFGNARITGWYAVPDK-QGPHPAIVKYHGYNASYDGEIHEMVNWALHGYAAFGMLVR |
| SEQ ID NO:6  | TYKSFGNARITGWYAVPDK-EGPHPAIVKYHGYNASYDGEIHEMVNWALHGYATFGMLVR |
| SEQ ID NO:8  | TYKSFGNARITGWYAVPDK-EGPHPAIVKYHGYNASYDGEIHEMVNWALHGYAAFGMLVR |
| SEQ ID NO:10 | TYRSIGGARIKGWYAVPDR-QGPHPAIVKYHGYNASYDGEIHEMVNWALHGYAAFGMLVR |
| SEQ ID NO:12 | TYQSFGHSKIEGFYAVPDQ-TGPHPALVRFHGYNASYDGGIHDIVNWALHGYATFGMLVR |
| SEQ ID NO:14 | EYLGFKGANIEGWLAVPEG-EGLYPGLVQFHGYNWAMDGCVPDVVNWALNGYAAFLMLVR |
| SEQ ID NO:16 | TFSGYRGQRIKGWLLVPKLAEEEKLPCVVQYIGYNGGR-GFPHDWLFWPSMGYICFVMDTR |
| SEQ ID NO:18 | TFSGYRGQRIKGWLLVPKLEEEKLPCVVQYIGYNGGR-GFPHDWLFWPSMGYICFVMDTR |
| SEQ ID NO:26 | YYRSAGNAKIHAKYVQPKA-GEKTPAVFMFHGYGGRS-AEWSSLLNYVAAGFSVFYMDVR |
| SEQ ID NO:32 | TYKSFGNARITGWYAVPDK-QGPHPAIVKYHGYNASYDGEIHEMVNWALHGYAAFGMLVR |
| SEQ ID NO:70 | YFTGVRGARIHAKYIRPKT-EGKHPALIREHGYSSNS-GDWNDKLNYVAAGFTVVAMDAR |
| | * * *  :. *  :*   * :: * .    :* . *.: |

FIGURE 1A

```
SEQ ID NO:2    GQQS----SEDTSISLHG-----HALGWMTKGILD-KDTYYYRGVYLDAVRALEVISSFDEV
SEQ ID NO:6    GQQS----SEDTSISPHG-----HALGWMTKGILD-KDTYYYRGVYLDAVRALEVISSFDEV
SEQ ID NO:8    GQQS----SEDTSISPHG-----HALGWMTKGILD-KDTYYYRGVYLDAVRALEVISSFDEV
SEQ ID NO:10   GQNS----SEDTEISHHG-----HVPGWMTKGILD-PKTYYYRGVYLDAVRAVEVVSGFAEV
SEQ ID NO:12   GQGG----SEDTSVTPGG-----HALGWMTKGILS-KDTYYYRGVYLDAVRALEVIQSFPEV
SEQ ID NO:14   GQQGR---SVDNIVPGSG-----HALGWMSKGILS--PEEYYYRGVYMDAVRAVEILASLPCV
SEQ ID NO:16   GQGSGWMKGDTPDYPEGPVDPQYPGFMTRGILD--PGTYYYRRVFVDAVRAVEAAISFPRV
SEQ ID NO:18   GQGSGWLKGDTPDYPEGPVDPQYPGFMTRGILD--PRTYYYRRVFTDAVRAVEAAASFPQV
SEQ ID NO:26   GQGGT---SEDPGGVRGN-----TYRGHIIRGLDAGPDALFYRSVFLDTVQLVRAAKTLPHI
SEQ ID NO:32   GQQS----SEDTSISPHG-----HALGWMTKGILD-KDTYYYRGVYLDAVRALEVISSFDEV
SEQ ID NO:70   GQGGQ---SQDVGGVNGN-----TLNGHIIRGLDDDADNMLFRHIFLDTAQLAGIVMNMPEI
                **        *  .      .           *     :  :  *:  :.  :. . :

SEQ ID NO:2    DETRIGVTGGSQGGGLTIAAAALSDIPKAAVADYPYLSNFERAIDVALEQ-PYLEINSFF
SEQ ID NO:6    DETRIGVTGGSQGGGLTIAAAALSDIPKAAVADYPYLSNFERAIDVALEQ-PYLEINSFF
SEQ ID NO:8    DETRIGVTGGSQGGGLTIAAAALSDIPKAAVADYPYLSNFERAIDVALEQ-PYLEINSFF
SEQ ID NO:10   DEKRIGVIGASQGGGLAVAVSALSDIPKAAVSEYPYLSNFQRAIDTAIDQ-PYLEINSFF
SEQ ID NO:12   DEHRIGVIGGSQGGALAIAAAALSDIPKVVVADYPYLSNFERAVDVALEQ-PYLEINSYF
SEQ ID NO:14   DESRIGVTGGSQGGGLALAVAALSGIPKVAAVHYPFLAHFERAIDVAPDG-PYLEINEYL
SEQ ID NO:16   DSRKVVVAGGSQGGGIALAVSALSNRVKALLCDVPFLCHFRRAVQLVDTH-PYVEITNFL
SEQ ID NO:18   DQERIVIAGGSQGGGIALAVSALSKKAKALLCDVPFLCHFRRAVQLVDTH-PYAEITNFL
SEQ ID NO:26   DKTRLMATGWSQGGALTLACAALVPEIKRLAPVYPFLSDYKRVWQMDLAVRSYKELADYF
SEQ ID NO:32   DETRIGVTGGSQGGGLTIAAAALSDIPKAAVADYPYLSNFERAIDVALEQ-PYLEINSFF
SEQ ID NO:70   DEDRVAVMGPSQGGGLSLACAALEPKIRKVVSEYPFLSDYKRVWDLDLAKNAYQEITDYF
                  *  .  ****..:::.*     .  :   *:*::* :     .     :

Figure 1B
```

```
SEQIDNO2    R-RNGSPETEVQAMKTLSYFDIMNLADRVKVPVLMSIGLIDKVTPPSTVFAAYNHLETEK
SEQIDNO6    R-RNGSPETEVQAMKTLSYFDIMNLADRVKVPVLMSIGLIDKVTPPSTVFAAYNHLETKK
SEQIDNO8    R-RNGSPETEEKAMKTLSYFDIMNLADRVKVPVLMSIGLIDKVTPPSTVFAAYNHLETEK
SEQIDNO10   R-RNTSPDIEQAAMHTLSYFDVMNLAQLVKATVLMSIGLVDTITPPSTVFAAYNHLETDK
SEQIDNO12   R-RNSDPKVEEKAFETLSYFDLINLAGWVKQPTLMAIGLIDKITPPSTVFAAYNHLETDK
SEQIDNO14   R-RNSGEEIERQVKKTLSYFDIMNLAPRIKCRTWICTGLVDEITPPSTVFAVYNHLKCPK
SEQIDNO16   K-THR--DKEEIVFRTLSYFDGVNFAARAKVPALFSVGLMDTICPPSTVFAAYNHYAGPK
SEQIDNO18   K-THR--DKEEIVFRTLSYFDGVNFAARAKIPALFSVGLMDNICPPSTVFAAYNYYAGPK
SEQIDNO26   RSYDPQHKRHGEIFERLGYIDVQHLADRIQGDVLMGVGLMDTECPPSTQFAAYNKIKAKK
SEQIDNO32   R-RNGSPETEVQAMKTLSYFDIMNLADRVKVPVLMSIGLIDKVTPPSTVFAAYNHLETEK
SEQIDNO70   RLFDPRHERENEVFTKLGYIDVKNLAKRIKGDVLMCVGLMDQVCPPSTVFAAYNIQSKK
              .         *  :*    .     .         .         ****  **.**    *

SEQIDNO2    ELKVYRYFGHEYIPAFQTEKLAFFKQHLKG---
SEQIDNO6    ELKVYRYFGHEYIPAFQTEKLAFFKQHLKG---
SEQIDNO8    ELKVYRYFGHEYIPAFQTEKLAFFKQHLKG---
SEQIDNO10   EIKVYRYFGHEYIPPFQTEKLAFLRKHLK----
SEQIDNO12   DLKVYRYFGHEFIPAFQTEKLSFLQKHLLLST
SEQIDNO14   EISVFRYFGHEHMPGSVEIKLRILMDELNP--
SEQIDNO16   EIRIYPYNNHEGGGSFQAIEQVKFLKRLFEEG
SEQIDNO18   EIRIYPYNNHEGGGSFQAVEQVKFLKKLFEKG
SEQIDNO26   SYELYPDFGHEHLPGMNDHIFRFFTS------
SEQIDNO32   ELKVYRYFGHEYIPAFQTEKLAFFKQHLKG---
SEQIDNO70   DIKVYPDYGHEPMRGFGDLAMQFMLELYS---
             .  :     ** .        . :
```

Figure 1C

PRODUCTION OF PERACIDS USING AN ENZYME HAVING PERHYDROLYSIS ACTIVITY

This application is a continuation in part of U.S. patent application Ser. No. 12/743,354, filed May 2, 2007, now U.S. Pat. No. 7,951,566, which is a continuation-in-part of U.S. patent application Ser. No. 11/638,635, filed Dec. 12, 2006, now U.S. Pat. No. 7,964,378 which claims the benefit of U.S. Provisional Application No. 60/750,092, filed Dec. 13, 2005, and U.S. Provisional Application No. 60/853,065, filed Oct. 20, 2006.

FIELD OF THE INVENTION

This invention relates to the field of peracid biosynthesis and in situ enzyme catalysis. Specifically, a process is provided to produce peracids using the perhydrolysis activity of enzymes identified structurally as belonging to the CE-7 family of carbohydrate esterases, including cephalosporin acetyl hydrolases (CAHs; E.C. 3.1.1.41) and acetyl xylan esterases (AXEs; E.C. 3.1.1.72). The enzymatic process produces percarboxylic acids from carboxylic acid ester substrates. Further, disinfectant formulations comprising the peracids produced by the processes described herein are provided.

BACKGROUND OF THE INVENTION

Peracid compositions have been reported to be effective antimicrobial agents. Methods to clean, disinfect, and/or sanitize hard surfaces, meat products, living plant tissues, and medical devices against undesirable microbial growth have been described (U.S. Pat. No. 6,545,047; U.S. Pat. No. 6,183,807; U.S. Pat. No. 6,518,307; U.S. patent application publication 20030026846; and U.S. Pat. No. 5,683,724). Peracids have also been reported to be useful in preparing bleaching compositions for laundry detergent applications (U.S. Pat. No. 3,974,082; U.S. Pat. No. 5,296,161; and U.S. Pat. No. 5,364,554).

Peracids can be prepared by the chemical reaction of a carboxylic acid and hydrogen peroxide (see Organic Peroxides, Daniel Swern, ed., Vol. 1, pp 313-516; Wiley Interscience, New York, 1971). The reaction is usually catalyzed by a strong inorganic acid, such as concentrated sulfuric acid. The reaction of hydrogen peroxide with a carboxylic acid is an equilibrium reaction, and the production of peracid is favored by the use of an excess concentration of peroxide and/or carboxylic acid, or by the removal of water. There are several disadvantages to the chemical reaction for peracid production: a) the high concentration of carboxylic acid used to favor production of peracid can result in an undesirable odor when using the peracid-containing solution, 2) the peracid is oftentimes unstable in solution over time, and the concentration of peracid in the solution decreases during storage prior to use, and 3) the formulation is often strongly acidic due to the use of a concentrated sulfuric acid as catalyst.

One way to overcome the disadvantages of the chemical production of peracids is to employ an enzyme catalyst in place of a strong acid catalyst. The use of an enzyme catalyst allows for the rapid production of peracid at the time of use and/or application, avoiding problems associated with storage of peracid solutions and variations in peracid concentrations over time. The high concentrations of carboxylic acids typically used to produce peracid via the direct chemical reaction with hydrogen peroxide are not required for enzymatic production of peracid, where the enzyme-catalyzed reaction can use a carboxylic acid ester as substrate at a much lower concentration than is typically used in the chemical reaction. The enzyme reaction can be performed across a broad range of pH, dependent on enzyme activity and stability at a given pH, and on the substrate specificity for perhydrolysis at a given pH.

Esterases, lipases, and some proteases have the ability catalyze the hydrolysis of alkyl esters to produce the corresponding carboxylic acids (Formula 1).

Lipase, Esterase, or Protease

$R_1COOR_2 + H_2O \rightarrow R_1COOH + HOR_2$    Formula 1

Some esterases, lipases, and proteases also exhibit perhydrolysis activity, catalyzing the synthesis of peracids from alkyl esters (Formula 2).

Lipase, Esterase, or Protease

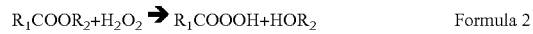

$R_1COOR_2 + H_2O_2 \rightarrow R_1COOOH + HOR_2$    Formula 2

O. Kirk et al. (Biocatalysis, 11:65-77 (1994)) investigated the ability of hydrolases (lipases, esterases, and proteases) to catalyze perhydrolysis of acyl substrates with hydrogen peroxide to form peroxycarboxylic acids, and reported that perhydrolysis proceeds with a very low efficiency in aqueous systems. Furthermore, they found that lipases and esterases degraded percarboxylic acid to the corresponding carboxylic acid and hydrogen peroxide. They also found that proteases neither degraded nor catalyzed perhydrolysis of carboxylic acid esters in water. The authors concluded that esterases, lipases and proteases are, in general, not suitable for catalyzing perhydrolysis of simple esters, such as methyl octanoate and trioctanoin, in an aqueous environment.

U.S. Pat. No. 3,974,082 describes the production of bleaching compositions for laundry detergent applications by contacting the material to be bleached with an aqueous solution containing an oxygen-releasing inorganic peroxygen compound, an acyl alkyl ester, and an esterase or lipase capable of hydrolyzing the ester.

U.S. Pat. No. 5,364,554 describes an activated oxidant system for in situ generation of peracid in aqueous solution using a protease enzyme, a source of hydrogen peroxide, and an ester substrate that is preferably chemically non-perhydrolyzable. A method of bleaching and a method of forming peracid are also disclosed.

U.S. Pat. No. 5,296,161 describes production of peracid in an aqueous solution comprising one or more specific esterases and lipases, a source of hydrogen peroxide, and a functionalized ester substrate suitable for use in a bleaching composition. However, the concentration of peracid produced was generally insufficient for use in many commercial disinfectant applications.

Most known methods for preparing peracids from the corresponding carboxylic acid esters using enzyme catalysts do not produce and accumulate a peracid at a sufficiently-high concentration to be efficacious for disinfection in a variety of applications. Several protease and lipase combinations have recently been reported to generate peracids (e.g., peracetic acid) in situ at concentrations suitable for use as a disinfectant and/or commercial bleaching agent (see co-owned U.S. patent application Ser. Nos. 11/413,246 and 11/588,523; herein incorporated by reference). However, there remains a need to identify additional perhydrolase catalysts capable of producing peracids in situ.

U.S. Pat. No. 4,444,886 describes a strain of Bacillus subtilis (ATCC 31954™) having ester hydrolase activity (described as a "diacetinase") that has high specificity for hydrolyzing glycerol esters having acyl groups having 2 to 8 carbon atoms. U.S. Pat. No. 4,444,886 does not describe, discuss or predict that the ester hydrolase activity of this strain has perhydrolase activity towards carboxylic acid esters, including glycerol esters.

The problem to be solved is to provide a process to enzymatically produce peracids in situ at concentrations suitable for use in a variety of disinfectant applications and/or bleaching applications. Preferably, the substrates used to produce the peracid compositions should be relatively non-toxic and inexpensive, such as carboxylic acid esters, especially mono-, di-, and triacylglycerols, wherein the acyl group has 1-8 carbon atoms, as well as acetylated sugars and C1 to C6 polyol esters.

SUMMARY OF THE INVENTION

The stated problems have been solved by the discovery that enzymes belonging to the structural family of CE-7 esterases (e.g., cephalosporin C deacetylases [CAHs] and acetyl xylan esterases [AXEs]) exhibit significant perhydrolysis activity for converting the present carboxylic acid esters (in the presence of an inorganic source of peroxygen such as hydrogen peroxide) into peracids at concentrations sufficient for use as a disinfectant and/or bleaching agent. The system achieves efficiency by producing the peracid in high concentrations without requiring a high concentration of peroxygen.

Specific examples of perhydrolases are exemplified from *Bacillus subtilis* (ATCC 31954™), *B. subtilis* BE1010 (Payne and Jackson, *J. Bacteriol.* 173:2278-2282 (1991)), *B. subtilis* ATCC 6633™ (U.S. Pat. No. 6,465,233), *B. subtilis* ATCC 29233™; *B. licheniformis* ATCC 14580™ (Rey et al., *Genome Biol.*, 5(10):article 77 (2004)), *Clostridium thermocellum* ATCC 27405™ (Copeland et al., GENBANK® ZP_00504991, *B. pumilus* PS213 (Degrassi et al., *Microbiology*, 146:1585-1591 (2000)), *Thermotoga neapolitana* (GENBANK® AAB70869.1), *Bacillus clausii* KSM-K16 (GENBANK® YP_175265), *Thermotoga maritima* MSB8 (GENBANK® NP_227893.1), and *Thermoanaerobacterium saccharolyticum* (GENBANK® S41858).

Each of the present perhydrolases described herein share conserved structural features (i.e. a conserved signature motif) as well as superior perhydrolysis activity when compared to other α/β-hydrolases, (such as commercially available lipases; see comparative Examples 26 and 28), making this unique family of enzymes particularly suitable for generating peracids in situ at concentrations sufficient for use as a disinfectant and/or bleaching agent. Suitable perhydrolases useful in the present process can be identified by a conserved signature motif found within the CE-7 family of carbohydrate esterases.

In one aspect of the invention, a process is provided for producing a peroxycarboxylic acid from a carboxylic acid ester comprising a) providing a set of reaction components comprising:
1) at least one substrate selected from the group consisting of:
  i) esters having the structure

[X]$_m$R$_5$ wherein X=an ester group of the formula R$_6$—C(O)O
  R$_6$=C1 to C7 linear, branched or cyclic hydrocarbyl moiety, optionally substituted with hydroxyl groups or C1 to C4 alkoxy groups, wherein R$_6$ optionally comprises one or more ether linkages for R$_6$=C2 to C7;

R$_5$=a C1 to C6 linear, branched, or cyclic hydrocarbyl moiety optionally substituted with hydroxyl groups; wherein each carbon atom in R$_5$ individually comprises no more than one hydroxyl group or no more than one ester group; wherein R$_5$ optionally comprises one or more ether linkages;
  m=1 to the number of carbon atoms in R$_5$; and
  wherein said esters have a solubility in water of at least 5 ppm at 25° C.;
  ii) glycerides having the structure

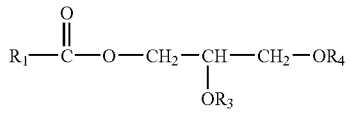

wherein R$_1$=C1 to C7 straight chain or branched chain alkyl optionally substituted with an hydroxyl or a C1 to C4 alkoxy group and R$_3$ and R$_4$ are individually H or R$_1$C(O); and
  iii) acetylated saccharides selected from the group consisting of acetylated monosaccharides, acetylated disaccharides, and acetylated polysaccharides;
2) a source of peroxygen; and
3) an enzyme catalyst having perhydrolysis activity, wherein said enzyme catalyst comprises an enzyme having a CE-7 signature motif that aligns with a reference sequence SEQ ID NO: 2 using CLUSTALW, said signature motif comprising:
  i) an RGQ motif at amino acid positions 118-120 of SEQ ID NO:2;
  ii) a GXSQG motif at amino acid positions 179-183 of SEQ ID NO:2; and
  iii) an HE motif at amino acid positions 298-299 of SEQ ID NO:2; and
  wherein said enzyme comprises at least 30% amino acid identity to SEQ ID NO: 2; and
b) combining said reaction components under suitable aqueous reaction conditions whereby a peroxycarboxylic acid is produced.

In another embodiment, suitable substrates also include esters of the formula:

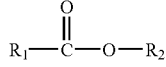

wherein R$_1$=C1 to C7 straight chain or branched chain alkyl optionally substituted with an hydroxyl or a C1 to C4 alkoxy group and R$_2$=C1 to C10 straight chain or branched chain alkyl, alkenyl, alkynyl, aryl, alkylaryl, alkylheteroaryl, heteroaryl, (CH$_2$CH$_2$—O)$_n$H or (CH$_2$CH(CH$_3$)—O)$_n$H and n=1 to 10.

In another aspect of the invention, a process to disinfect a surface or inanimate object is provided, said process comprising in addition to the above process the step of:

c) contacting a surface or inanimate object with the peroxycarboxylic acid produced in step (b) whereby said surface or said inanimate object is disinfected.

In a further embodiment, the above process comprises an enzyme catalyst comprising an amino acid sequence selected from the group consisting of SEQ ID NO: 18, SEQ ID NO: 26, and SEQ ID NO: 70 or a substantially similar enzyme having perhydrolase activity derived by substituting, deleting or adding one or more amino acids to said amino acid sequence.

In a further embodiment, the substantially similar enzyme having perhydrolase activity is at least 95% identical to one or more amino acid sequences selected from the group consisting of SEQ ID NO: 18, SEQ ID NO: 26, and SEQ ID NO: 70.

In a preferred embodiment, the substrate is selected from the group consisting of: monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol; and mixtures thereof.

BRIEF DESCRIPTION OF THE FIGURE

FIG. 1 (panels a-c) is a CLUSTALW alignment of perhydrolases of the present invention. Each of the perhydrolases are structurally classified members of the carbohydrate esterase family 7 (CE-7) and share certain conserved domains. Several conserved motifs (underlined) have been identified that together form the signature motif for CE-7 carbohydrate esterases. An additional motif (LXD; amino acid residues 267-269 of SEQ ID NO: 2) is also underlined and may be used to further characterize the signature motif.

BRIEF DESCRIPTION OF THE BIOLOGICAL SEQUENCES

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO: 1 is the nucleic acid sequence of the cephalosporin C deacetylase (cah) coding region from *Bacillus subtilis* ATCC 31954™.

SEQ ID NO: 2 is the deduced amino acid sequence of the cephalosporin C deacetylase from *Bacillus subtilis* ATCC 31954™.

SEQ ID NOs: 3 and 4 are primers used to PCR amplify perhydrolase genes from *Bacillus subtilis* species for construction of pSW186, pSW187, pSW188, and pSW190.

SEQ ID NO: 5 is the nucleic acid sequence of the cephalosporin C deacetylase coding region from *B. subtilis* subsp. *subtilis* str. 168.

SEQ ID NO: 6 is the deduced amino acid sequence of the cephalosporin C deacetylase from *B. subtilis* subsp. *subtilis* str. 168, and is identical to the deduced amino acid sequence of the cephalosporin C deacetylase from *B. subtilis* BE1010.

SEQ ID NO: 7 is the nucleic acid sequence of the cephalosporin acetylesterase coding region from *B. subtilis* ATCC 6633™.

SEQ ID NO: 8 is the deduced amino acid sequence of the cephalosporin acetylesterase from *B. subtilis* ATCC 6633™.

SEQ ID NO: 9 is the nucleic acid sequence of the cephalosporin C deacetylase coding region from *B. licheniformis* ATCC 14580™.

SEQ ID NO: 10 is the deduced amino acid sequence of the cephalosporin C deacetylase from *B. licheniformis* ATCC 14580™.

SEQ ID NO: 11 is the nucleic acid sequence of the acetyl xylan esterase coding region from *B. pumilus* PS213.

SEQ ID NO: 12 is the deduced amino acid sequence of the acetyl xylan esterase from *B. pumilus* PS213.

SEQ ID NO: 13 is the nucleic acid sequence of the acetyl xylan esterase coding region from *Clostridium thermocellum* ATCC 27405™.

SEQ ID NO: 14 is the deduced amino acid sequence of the acetyl xylan esterase from *Clostridium thermocellum* ATCC 27405™.

SEQ ID NO: 15 is the nucleic acid sequence of the acetyl xylan esterase coding region from *Thermotoga neapolitana*.

SEQ ID NO: 16 is the deduced amino acid sequence of the acetyl xylan esterase from *Thermotoga neapolitana*.

SEQ ID NO: 17 is the nucleic acid sequence of the acetyl xylan esterase coding region from *Thermotoga maritima* MSB8.

SEQ ID NO: 18 is the deduced amino acid sequence of the acetyl xylan esterase from *Thermotoga maritima* MSB8.

SEQ ID NO: 19 is the nucleic acid sequence of the acetyl xylan esterase coding region from *Thermoanaerobacterium* sp. JW/SL YS485.

SEQ ID NO: 20 is the deduced amino acid sequence of the acetyl xylan esterase from *Thermoanaerobacterium* sp. JW/SL YS485.

SEQ ID NO: 21 is the nucleic acid sequence of the cephalosporin C deacetylase coding region from *Bacillus* sp. NRRL B-14911.

SEQ ID NO: 22 is the deduced amino acid sequence of the cephalosporin C deacetylase from *Bacillus* sp. NRRL B-14911.

SEQ ID NO: 23 is the nucleic acid sequence of the cephalosporin C deacetylase coding region from *Bacillus halodurans* C-125.

SEQ ID NO: 24 is the deduced amino acid sequence of the cephalosporin C deacetylase from *Bacillus halodurans* C-125.

SEQ ID NO: 25 is the nucleic acid sequence of the cephalosporin C deacetylase coding region from *Bacillus clausii* KSM-K16.

SEQ ID NO: 26 is the deduced amino acid sequence of the cephalosporin C deacetylase from *Bacillus clausii* KSM-K16.

SEQ ID NOs: 27 and 28 are primers used to PCR amplify perhydrolase genes from *Bacillus subtilis* species for construction of pSW194 and pSW189.

SEQ ID NO: 29 is the nucleic acid sequence of the PCR product cloned into pSW194.

SEQ ID NO: 30 is the nucleic acid sequence of the PCR product cloned into pSW189.

SEQ ID NO: 31 is the nucleic acid sequence of the *Bacillus subtilis* ATCC 29233™ cephalosporin C deacetylase (cah) gene cloned into pSW190.

SEQ ID NO: 32 is the deduced amino acid sequence of the *Bacillus subtilis* ATCC 29233™ cephalosporin C deacetylase (CAH).

SEQ ID NOs: 33 and 34 are primers used to PCR amplify the *Bacillus licheniformis* ATCC 14580™ cephalosporin C deacetylase gene for construction of pSW191.

SEQ ID NOs: 35 and 36 are primers used to PCR amplify the *Clostridium thermocellum* ATCC 27405™ acetyl xylan esterase gene for construction of pSW193.

SEQ ID NOs: 37 and 38 are primers used to PCR amplify the *Bacillus pumilus* PS213 acetyl xylan esterase coding sequence (GENBANK® AJ249957) for construction of pSW195.

SEQ ID NOs: 39 and 40 are primers used to PCR amplify the *Thermotoga neapolitana* acetyl xylan esterase gene (GENBANK® 58632) for construction of pSW196.

SEQ ID NO: 41 is the nucleic acid sequence of the codon-optimized version of the *Thermotoga neapolitana* acetyl xylan esterase gene in plasmid pSW196.

SEQ ID NO: 42 is the nucleic acid sequence of the kanamycin resistance gene.

SEQ ID NO: 43 is the nucleic acid sequence of plasmid pKD13.

SEQ ID NOs: 44 and 45 are primers used to generate a PCR product encoding the kanamycin gene flanked by regions having homology to the katG catalase gene in *E. coli* MG1655. The product was used to disrupt the endogenous katG gene.

SEQ ID NO: 46 is the nucleic acid sequence of the PCR product encoding the kanamycin resistance gene flanked by regions having homology to the katG catalase gene in *E. coli* MG1655. The product was used to disrupt the endogenous katG gene.

SEQ ID NO: 47 is the nucleic acid sequence of the katG catalase gene in *E. coli* MG1655.

SEQ ID NO: 48 is the deduced amino acid sequence of the KatG catalase in *E. coli* MG1655.

SEQ ID NO: 49 is the nucleic acid sequence of plasmid pKD46.

SEQ ID NOs: 50 and 51 are primers used to confirm the disruption of the katG gene.

SEQ ID NO: 52 is the nucleic acid sequence of plasmid pCP20.

SEQ ID NO: 53 and 54 are primers used to generate a PCR product encoding the kanamycin gene flanked by regions having homology to the katE catalase gene in *E. coli* MG1655. The product was used to disrupt the endogenous katE gene.

SEQ ID NO: 55 is the nucleic acid sequence of the PCR product encoding the kanamycin resistance gene flanked by regions having homology to the katE catalase gene in *E. coli* MG1655. The product was used to disrupt the endogenous katE gene.

SEQ ID NO: 56 is the nucleic acid sequence of the katE catalase gene in *E. coli* MG1655.

SEQ ID NO: 57 is the deduced amino acid sequence of the KatE catalase in *E. coli* MG1655.

SEQ ID NOs: 58 and 59 are primers used to confirm disruption of the katE gene in the single knockout strain *E. coli* MG1655 ΔkatE, and in the double-knockout strain *E. coli* MG1655 ΔkatG ΔkatE, herein referred to as *E. coli* KLP18.

SEQ ID NO: 60 is the nucleic acid sequence of the codon optimized version of the *Bacillus pumilus* PS213 encoding the amino acid sequence SEQ ID NO: 12.

SEQ ID NO: 61 is the amino acid sequence of the region encompassing amino acids residues 118 through 299 of SEQ ID NO: 2.

SEQ ID NOs: 62 and 63 are the nucleic acid sequences of the primers used to PCR amplify a codon-optimized version of the *Bacillus clausii* KSM-K16 cephalosporin-C deacetylase.

SEQ ID NO: 64 is the nucleic acid sequence of the PCR product encoding the codon-optimized version of the *Bacillus clausii* KSM-K16 cephalosporin-C deacetylase coding sequence.

SEQ ID NO: 65 is the nucleic acid sequence of the codon-optimized *Bacillus clausii* KSM-K16 cephalosporin-C deacetylase coding sequence.

SEQ ID NOs: 66 and 67 are the nucleic acid sequences of the primers used to PCR amplify a codon-optimized version of the *Thermoanaerobacterium saccharolyticum* acetyl xylan esterase coding region (GENBANK® Accession No. S41858).

SEQ ID NO: 68 is the nucleic acid sequence of the PCR product encoding the codon-optimized version of the *Thermoanaerobacterium saccharolyticum* acetyl xylan esterase coding sequence.

SEQ ID NO: 69 is the nucleic acid sequence of the codon-optimized version of the *Thermoanaerobacterium saccharolyticum* acetyl xylan esterase coding sequence.

SEQ ID NO: 70 is the deduced amino acid sequence of the acetyl xylan esterase from *Thermoanaerobacterium saccharolyticum* (GENBANK® Accession No. S41858).

SEQ ID NOs: 71 and 72 are the nucleic acid sequences of the primers used to PCR amplify a codon-optimized version of the *Thermotoga maritima* MSB8 (GENBANK® Accession No. NP_227893.1) acetyl xylan esterase coding sequence.

SEQ ID NO: 73 is the nucleic acid sequence of the PCR product encoding the codon-optimized version of the *Thermotoga maritima* MSB8 acetyl xylan esterase coding sequence.

SEQ ID NO: 74 is the nucleic acid sequence of the codon-optimized version of the *Thermotoga maritima* MSB8 acetyl xylan esterase coding sequence.

DETAILED DESCRIPTION OF THE INVENTION

The stated problems have been solved by the discovery that enzymes belonging to the CE-7 carbohydrate esterase family exhibit significant perhydrolysis activity for converting carboxylic acid ester substrates to peracids. This family of structurally related enzymes can be used to generate concentrations of peracids with high efficiency for disinfection and/or bleaching applications.

In this disclosure, a number of terms and abbreviations are used. The following definitions apply unless specifically stated otherwise.

As used herein, the term "comprising" means the presence of the stated features, integers, steps, or components as referred to in the claims, but that it does not preclude the presence or addition of one or more other features, integers, steps, components or groups thereof.

As used herein, the term "about" modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the term "peracid" is synonymous with peroxyacid, peroxycarboxylic acid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane, 1,2,3-propanetriol triacetate and all other synonyms of CAS Registry Number 102-76-1.

As used herein, the term "monobutyrin" is synonymous with glycerol monobutyrate, glycerin monobutyrate, and glyceryl monobutyrate.

As used herein, the term "dibutyrin" is synonymous with glycerol dibutyrate and glyceryl dibutyrate.

As used herein, the term "tributyrin" is synonymous with glycerol tributyrate, 1,2,3-tributyrylglycerol, and all other synonyms of CAS Registry Number 60-01-5.

As used herein, the term "monopropionin" is synonymous with glycerol monopropionate, glycerin monopropionate, and glyceryl monopropionate.

As used herein, the term "dipropionin" is synonymous with glycerol dipropionate and glyceryl dipropionate.

As used herein, the term "tripropionin" is synonymous with glyceryl tripropionate, glycerol tripropionate, 1,2,3-tripropionylglycerol, and all other synonyms of CAS Registry Number 139-45-7.

As used herein, the term "ethyl acetate" is synonymous with acetic ether, acetoxyethane, ethyl ethanoate, acetic acid ethyl ester, ethanoic acid ethyl ester, ethyl acetic ester and all other synonyms of CAS Registry Number 141-78-6.

As used herein, the term "ethyl lactate" is synonymous with lactic acid ethyl ester and all other synonyms of CAS Registry Number 97-64-3.

As used herein, the terms "acetylated sugar" and "acetylated saccharide" refer to mono-, di- and polysaccharides comprising at least one acetyl group. Examples include, but are not limited to glucose pentaacetate, xylose tetraacetate, acetylated xylan, acetylated xylan fragments, β-D-ribofuranose-1,2,3,5-tetraacetate, tri-O-acetyl-D-galactal, and tri-O-acetyl-glucal.

As used herein, the terms "hydrocarbyl", "hydrocarbyl group", and "hydrocarbyl moiety" is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In a preferred embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the terms "monoesters" and "diesters" of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol, refer to said compounds comprising at least one ester group of the formula RC(O)O, wherein R is a C1 to C7 linear hydrocarbyl moiety.

As used herein, the terms "suitable enzymatic reaction mixture", "components suitable for in situ generation of a peracid", "suitable reaction components", and "suitable aqueous reaction mixture" refer to the materials and water in which the reactants and enzyme catalyst come into contact. The components of the suitable aqueous reaction mixture are provided herein and those skilled in the art appreciate the range of component variations suitable for this process. In one embodiment, the suitable enzymatic reaction mixture produces peracid in situ upon combining the reaction components. As such, the reaction components may be provided as a multicomponent system wherein one or more of the reaction components remains separated until use. The design of systems and means for separating and combining multiple active components are known in the art and generally will depend upon the physical form of the individual reaction components. For example, multiple active fluids (liquid-liquid) systems typically use multichamber dispenser bottles or two-phase systems (U.S. Patent Application Pub. No. 2005/0139608; U.S. Pat. No. 5,398,846; U.S. Pat. No. 5,624,634; U.S. Pat. No. 6,391,840; E.P. Patent 0807156B1; U.S. Patent Appln. Pub. No. 2005/0008526; and PCT Publication No. WO 00/11713A1) such as found in some bleaching applications wherein the desired bleaching agent is produced upon mixing the reactive fluids. Other forms of multicomponent systems used to generate peracid may include, but are not limited to those designed for one or more solid components or combinations of solid-liquid components, such as powders (e.g., many commercially available bleaching composition, U.S. Pat. No. 5,116,575), multi-layered tablets (U.S. Pat. No. 6,210,639), water dissolvable packets having multiple compartments (U.S. Pat. No. 6,995,125) and solid agglomerates that react upon the addition of water (U.S. Pat. No. 6,319,888).

In one embodiment, a formulation is provided as two individual mixtures whereby a peroxycarboxylic acid disinfectant is generated upon combining the two mixtures.

In another embodiment, a formulation is provided comprising:
a) a first mixture comprising:
  i) an enzyme catalyst having perhydrolase activity, said enzyme catalyst comprising an enzyme having a CE-7 signature motif; and
  ii) a carboxylic acid ester substrate, said first mixture optionally comprising a component selected from the group consisting of an inorganic or organic buffer, a corrosion inhibitor, a wetting agent, and combinations thereof; and
b) a second mixture comprising a source of peroxygen and water, said second mixture optionally comprising a chelating agent.

In a further related embodiment, the carboxylic acid ester substrate in the first mixture of the formulation is selected from the group consisting of:
i) esters having the structure

wherein X=an ester group of the formula $R_6$—C(O)O
$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
$R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;

m=1 to the number of carbon atoms in $R_5$; and wherein said esters have a solubility in water of at least 5 ppm at 25° C.;

ii) glycerides having the structure

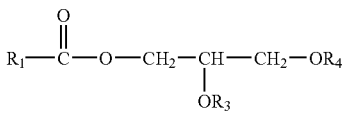

wherein $R_1$=C1 to C7 straight chain or branched chain alkyl optionally substituted with an hydroxyl or a C1 to C4 alkoxy group and $R_3$ and $R_4$ are individually H or $R_1C(O)$; and iii) acetylated saccharides selected from the group consisting of acetylated monosaccharides, acetylated disaccharides, and acetylated polysaccharides;

In another embodiment, the carboxylic acid ester substrate in the first mixture of the formulation is defined by the following formula:

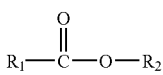

wherein $R_1$=C1 to C7 straight chain or branched chain alkyl optionally substituted with an hydroxyl or a C1 to C4 alkoxy group and $R_2$=C1 to C10 straight chain or branched chain alkyl, alkenyl, alkynyl, aryl, alkylaryl, alkylheteroaryl, heteroaryl, $(CH_2CH_2-O)_nH$ or $(CH_2CH(CH_3)-O)_nH$ and n=1 to 10.

In a preferred embodiment, $R_6$ is C1 to C7 linear hydrocarbyl moiety, optionally substituted with hydroxyl groups or C1 to C4 alkoxy groups, optionally comprising one or more ether linkages. In a further preferred embodiment, $R_6$ is C2 to C7 linear hydrocarbyl moiety, optionally substituted with hydroxyl groups, and/or optionally comprising one or more ether linkages.

In another embodiment, the carboxylic acid ester substrate is selected from the group consisting of: monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol; and mixtures thereof.

In another embodiment, the carboxylic acid ester is selected from the group consisting of monoacetin, diacetin, triacetin, and combinations thereof. In another embodiment, the carboxylic acid ester is an acetylated saccharide. In another embodiment, the substrate is a C1 to C6 polyol comprising one or more ester groups. In a preferred embodiment, one or more of the hydroxyl groups on the C1 to C6 polyol are substituted with one or more acetoxy groups (e.g. 1,3-propanediol diacetate, 1,4-butanediol diacetate, etc.). In another embodiment, the enzyme catalyst is a particulate solid. In another embodiment, the first reaction mixture described above is a solid tablet or powder.

As used herein, the term "perhydrolysis" is defined as the reaction of a selected substrate with peroxide to form a peracid. Typically, inorganic peroxide is reacted with the selected substrate in the presence of a catalyst to produce the peracid. As used herein, the term "chemical perhydrolysis" includes perhydrolysis reactions in which a substrate (a peracid precursor) is combined with a source of hydrogen peroxide wherein peracid is formed in the absence of an enzyme catalyst.

As used herein, the term "perhydrolase activity" refers to the catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 μmol of peracid product per minute at a specified temperature.

As used herein, the terms "enzyme catalyst" and "perhydrolase catalyst" refer to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (e.g., by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. As described herein, all of the present enzymes having perhydrolysis activity are structurally members of the carbohydrate family esterase family 7 (CE-7 family) of enzymes (see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.).

Members of the CE-7 family include cephalosporin C deacetylases (CAHs; E.C. 3.1.1.41) and acetyl xylan esterases (AXEs; E.C. 3.1.1.72). Members of the CE-7 esterase family share a conserved signature motif (Vincent et al., *J. Mol. Biol.*, 330:593-606 (2003)). Perhydrolases comprising the CE-7 signature motif and/or a substantially similar structure are suitable for use in the present invention. Means to identify substantially similar biological molecules are well known in the art (e.g. sequence alignment protocols, nucleic acid hybridizations, presence of a conserved signature motif, etc.). In one aspect, the enzyme catalyst in the present process comprises a substantially similar enzyme having at least 30%, preferably at least 33%, more preferably at least 40%, more preferably at least 50%, even more preferably at least 60%, yet even more preferable at least 70%, yet even more preferably at least 80%, yet even more preferable at least 90% identity, and most preferably at least 95% amino acid identity to the sequences provided herein. The nucleic acid molecules encoding the present CE-7 carbohydrate esterases are also provided herein. In a further embodiment, the perhydrolase catalyst useful in the present process is encoded by a nucleic acid molecule that hybridizes stringent conditions to one of the present nucleic acid molecules.

As used herein, the terms "cephalosporin C deacetylase" and "cephalosporin C acetyl hydrolase" refers to an enzyme (E.C. 3.1.1.41) that catalyzes the deacetylation of cephalosporins such as cephalosporin C and 7-aminocephalosporanic acid (Mitsushima et al., supra). As described herein, several cephalosporin C deacetylases are provided having significant perhydrolysis activity.

As used herein, "acetyl xylan esterases"" refers to an enzyme (E.C. 3.1.1.72; AXEs) that catalyzes the deacetylation of acetylated xylans and other acetylated saccharides. As illustrated herein, several enzymes classified as acetyl xylan esterases are provided having significant perhydrolase activity.

As used herein, the term "*Bacillus subtilis* (ATCC 31954™)" refers to a bacterial cell deposited to the American Type Culture Collection (ATCC) having international depository accession number ATCC 31954™. *Bacillus subtilis* ATCC 31954™ has been reported to have an ester hydrolase ("diacetinase") activity capable of hydrolyzing glycerol esters having 2-carbon to 8-carbon acyl groups, especially diacetin (U.S. Pat. No. 4,444,886; herein incorporated by reference in its entirety). As described herein, an enzyme having significant perhydrolase activity has been isolated from *B. subtilis* ATCC 31954™ and is provided as SEQ ID NO: 2. The amino acid sequence of the isolated enzyme has 100% amino acid identity to the cephalosporin C deacetylase provided by GENBANK® Accession No. BAA01729.1.

As used herein, the term "*Bacillus subtilis* BE1010" refers to the strain of *Bacillus subtilis* as reported by Payne and Jackson (*J. Bacteriol.* 173:2278-2282 (1991)). *Bacillus subtilis* BE1010 is a derivative *Bacillus subtilis* subsp. *subtilis* strain BR151 (ATCC 33677™) having a chromosomal deletion in the genes encoding subtilisin and neutral protease. As described herein, an enzyme having significant perhydrolase activity has been isolated from *B. subtilis* BE1010 and is provided as SEQ ID NO: 6. The amino acid sequence of the isolated enzyme has 100% amino acid identity to the cephalosporin C deacetylase reported in *Bacillus subtilis* subsp. *subtilis* strain 168 (Kunst et al., supra).

As used herein, the term "*Bacillus subtilis* ATCC 29233™" refers to a strain of *Bacillus subtilis* deposited to the American Type Culture Collection (ATCC) having international depository accession number ATCC 29233™. As described herein, an enzyme having significant perhydrolase activity has been isolated and sequence from *B. subtilis* ATCC 29233™ and is provided as SEQ ID NO: 32.

As used herein, the term "*Clostridium thermocellum* ATCC 27405™" refers to a strain of *Clostridium thermocellum* deposited to the American Type Culture Collection (ATCC) having international depository accession number ATCC 27405™. The amino acid sequence of the enzyme having perhydrolase activity from *C. thermocellum* ATCC 27405™ is provided as SEQ ID NO: 14.

As used herein, the term "*Bacillus subtilis* ATCC 6633™" refers to a bacterial cell deposited to the American Type Culture Collection (ATCC) having international depository accession number ATCC 6633™. *Bacillus subtilis* ATCC 6633™ has been reported to have cephalosporin acetylhydrolase activity (U.S. Pat. No. 6,465,233). The amino acid sequence of the enzyme having perhydrolase activity from *B. subtilis* ATCC 6633™ is provided as SEQ ID NO: 8.

As used herein, the term "*Bacillus licheniformis* ATCC 14580™" refers to a bacterial cell deposited to the American Type Culture Collection (ATCC) having international depository accession number ATCC 14580™. *Bacillus licheniformis* ATCC 14580™ has been reported to have cephalosporin acetylhydrolase activity (GENBANK® YP_077621). The amino acid sequence of the enzyme having perhydrolase activity from *B. licheniformis* ATCC 14580™ is provided as SEQ ID NO: 10.

As used herein, the term "*Bacillus pumilus* PS213" refers to a bacterial cell reported to have acetyl xylan esterase activity (GENBANK® AJ249957). The amino acid sequence of the enzyme having perhydrolase activity from *Bacillus pumilus* PS213 is provided as SEQ ID NO: 12.

As used herein, the term "*Thermotoga neapolitana*" refers to a strain of *Thermotoga neapolitana* reported to have acetyl xylan esterase activity (GENBANK® AAB70869). The amino acid sequence of the enzyme having perhydrolase activity from *Thermotoga neapolitana* is provided as SEQ ID NO: 16.

As used herein, the term "*Thermotoga maritima* MSB8" refers to a bacterial cell reported to have acetyl xylan esterase activity (GENBANK® NP_227893.1). The amino acid sequence of the enzyme having perhydrolase activity from *Thermotoga maritima* MSB8 is provided as SEQ ID NO: 18.

As used herein, the term "*Bacillus clausii* KSM-K16" refers to a bacterial cell reported to have cephalosporin-C deacetylase activity (GENBANK®YP_175265). The amino acid sequence of the enzyme having perhydrolase activity from *Bacillus clausii* KSM-K16 is provided as SEQ ID NO: 26.

As used herein, the term "*Thermoanearobacterium saccharolyticum*" refers to a bacterial strain reported to have acetyl xylan esterase activity (GENBANK™ S41858). The amino acid sequence of the enzyme having perhydrolase activity from *Thermoanearobacterium saccharolyticum* is provided as SEQ ID NO: 70.

As used herein, an "isolated nucleic acid molecule" and "isolated nucleic acid fragment" will be used interchangeably and refers to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid (or as defined herein) | Xaa | X |

As used herein, "substantially similar" refers to nucleic acid molecules wherein changes in one or more nucleotide bases results in the addition, substitution, or deletion of one or more amino acids, but does not affect the functional properties (i.e. perhydrolytic activity) of the protein encoded by the DNA sequence. As used herein, "substantially similar" also refers to an enzyme having an amino acid sequence that is at least 30%, preferably at least 33%, more preferably at least 40%, more preferably at least 50%, even more preferably at least 60%, even more preferably at least 70%, even more preferably at least 80%, yet even more preferably at least 90%, and most preferably at least 95% identical to the sequences reported herein wherein the resulting enzyme retains the present functional properties (i.e., perhydrolytic activity). "Substantially similar" may also refer to an enzyme having perhydrolytic activity encoded by nucleic acid molecules that hybridizes under stringent conditions to the nucleic acid molecules reported herein. It is therefore understood that the invention encompasses more than the specific exemplary sequences.

For example, it is well known in the art that alterations in a gene which result in the production of a chemically equivalent amino acid at a given site, but do not affect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences are encompassed by the present invention. In one embodiment, substantially similar sequences are defined by their ability to hybridize, under stringent conditions (0.1×SSC, 0.1% SDS, 65° C. and washed with 2×SSC, 0.1% SDS followed by 0.1×SSC, 0.1% SDS, 65° C.) with the sequences exemplified herein. In one embodiment, the present invention includes enzymes having perhydrolase activity encoded by isolated nucleic acid molecules that hybridize under stringent conditions to the nucleic acid molecules reported herein. In a preferred embodiment, the present invention includes an enzyme having perhydrolase activity encoded by isolated nucleic acid molecule that hybridize under stringent conditions to a nucleic acid molecule having an nucleic acid sequence selected from the group consisting of SEQ ID NO: 17; SEQ ID NO: 25; SEQ ID NO: 69, and SEQ ID NO: 74.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of stringent hybridization conditions is 0.1×SSC, 0.1% SDS, 65° C. and washed with 2×SSC, 0.1% SDS followed by a final wash of 0.1×SSC, 0.1% SDS, 65° C. with the sequences exemplified herein.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6) pp 276-277 (2000)). Multiple alignment of the sequences can be performed using the Clustal method (i.e. CLUSTALW; for example version 1.83) of alignment (Higgins and Sharp, CABIOS, 5:151-153 (1989); Higgins et al., *Nucleic Acids Res.* 22:4673-4680 (1994); and Chenna et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g. Gonnet250), protein ENDGAP=−1, Protein GAPDIST=4, and KTUPLE=1. In one embodiment, a fast or slow alignment is used with the default settings where a slow alignment is preferred. Alternatively, the parameters using the CLUSTALW method (version 1.83) may be modified to also use KTUPLE=1, GAP PENALTY=10, GAP extension=1, matrix=BLOSUM (e.g. BLOSUM64), WINDOW=5, and TOP DIAGONALS SAVED=5.

In one aspect of the present invention, suitable isolated nucleic acid molecules (isolated polynucleotides of the present invention) encode a polypeptide having an amino acid sequence that is at least about 30%, preferably at least 33%, preferably at least 40%, preferably at least 50%, preferably at least 60%, more preferably at least 70%, more preferably at least 80%, even more preferably at least 85%, even more preferably at least 90%, and most preferably at least 95% identical to the amino acid sequences reported herein. Suitable nucleic acid molecules of the present invention not only have the above homologies, but also typically encode a polypeptide having about 300 to about 340 amino acids, more preferably about 310 to about 330 amino acids, and most preferably about 318 amino acids.

As used herein, the terms "signature motif", "CE-7 signature motif", and "diagnostic motif" refer to conserved structures shared among a family of enzymes having a defined activity. The signature motif can be used to define and/or identify the family of structurally related enzymes having similar enzymatic activity for a defined family of substrates. The signature motif can be a single contiguous amino acid sequence or a collection of discontiguous, conserved motifs that together form the signature motif. Typically, the conserved motif(s) is represented by an amino acid sequence. As described herein, the present perhydrolases belong to the family of CE-7 carbohydrate esterases. This family of enzymes can be defined by the presence of a signature motif (Vincent et al., supra).

As used herein, "codon degeneracy" refers to the nature of the genetic code permitting variation of the nucleotide sequence without affecting the amino acid sequence of an encoded polypeptide. Accordingly, the present invention relates to any nucleic acid molecule that encodes all or a substantial portion of the amino acid sequences encoding the present microbial polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As used herein, "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene at different stages of development, or in response to different environmental or physiological conditions. Promoters that cause a gene to be expressed at most times are commonly referred to as "constitutive promoters". It is further recognized that since in most cases the exact boundaries of regulatory sequences have not been completely defined, DNA fragments of different lengths may have identical promoter activity.

As used herein, the "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts (normally limited to eukaryotes) to the 3' end of the mRNA precursor.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., that the coding sequence is under the transcriptional control of the promoter. Coding sequences can be operably linked to regulatory sequences in sense or antisense orientation.

As used herein, the term "expression" refers to the transcription and stable accumulation of sense (mRNA) or antisense RNA derived from the nucleic acid molecule of the invention. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal (e.g. plasmid) genes. Host organisms containing the transformed nucleic acid molecules are referred to as "transgenic" or "recombinant" or "transformed" organisms.

As used herein, the terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), CLUSTALW (for example, version 1.83; Thompson et al., *Nucleic Acids Research,* 22(22):4673-4680 (1994), and the FASTA program incorporating the Smith-Waterman algorithm (W. R. Pearson, *Comput. Methods Genome Res., [Proc. Int. Symp.] (*1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

As used herein, the term "biological contaminants" refers to one or more unwanted and/or pathogenic biological entities including, but not limited to microorganisms, spores, viruses, prions, and mixtures thereof. The process produces an efficacious concentration of at least one percarboxylic acid useful to reduce and/or eliminate the presence of the viable biological contaminants. In a preferred embodiment, the microbial contaminant is a viable pathogenic microorganism.

As used herein, the term "disinfect" refers to the process of destruction of or prevention of the growth of biological contaminants. As used herein, the term "disinfectant" refers to an agent that disinfects by destroying, neutralizing, or inhibiting the growth of biological contaminants. Typically, disinfectants are used to treat inanimate objects or surfaces. As used herein, the term "antiseptic" refers to a chemical agent that inhibits the growth of disease-carrying microorganisms. In one aspect of the embodiment, the biological contaminants are pathogenic microorganisms.

As used herein, the term "virucide" refers to an agent that inhibits or destroys viruses, and is synonymous with "viricide". An agent that exhibits the ability to inhibit or destroy viruses is described as having "virucidal" activity. Peracids can have virucidal activity. Typical alternative virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peracids can have biocidal activity. Typical alternative biocides known in the art, which may be suitable for use in the present invention include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $\log_{10}$ reduction in viable microorganisms after treatment. In one aspect, the targeted reduction in viable microorganisms after treatment is at least a 3-log reduction, more preferably at least a 4-log reduction, and most preferably at least a 5-log reduction. In another aspect, the minimum biocidal concentration is at least a 6-log reduction in viable microbial cells.

As used herein, the terms "peroxygen source" and "source of peroxygen" refer to compounds capable of providing hydrogen peroxide at a concentration of about 1 mM or more when in an aqueous solution including, but not limited to hydrogen peroxide, hydrogen peroxide adducts (e.g., urea-hydrogen peroxide adduct (carbamide peroxide)), perborates, and percarbonates. As described herein, the concentration of the hydrogen peroxide provided by the peroxygen compound in the aqueous reaction mixture is initially at least 1 mM or more upon combining the reaction components. In one embodiment, the hydrogen peroxide concentration in the aqueous reaction mixture is at least 10 mM. In another embodiment, the hydrogen peroxide concentration in the aqueous reaction mixture is at least 100 mM. In another embodiment, the hydrogen peroxide concentration in the aqueous reaction mixture is at least 200 mM. In another embodiment, the hydrogen peroxide concentration in the aqueous reaction mixture is 500 mM or more. In yet another embodiment, the hydrogen peroxide concentration in the aqueous reaction mixture is 1000 mM or more. The molar ratio of the hydrogen peroxide to enzyme substrate, e.g. triglyceride, ($H_2O_2$:substrate) in the aqueous reaction mixture may be from about 0.002 to 20, preferably about 0.1 to 10, and most preferably about 0.5 to 5.

Suitable Reaction Conditions for the Enzyme-Catalyzed Preparation of Peracids from Carboxylic Acid Esters and Hydrogen Peroxide In one aspect of the invention, a process is provided to produce an aqueous mixture comprising a peracid by reacting carboxylic acid esters and an inorganic peroxide, not limited to hydrogen peroxide, sodium perborate or sodium percarbonate, in the presence of an enzyme catalyst having perhydrolysis activity. In one embodiment, the enzyme catalyst comprises a perhydrolase having a structure belonging to the CE-7 carbohydrate esterase family. In another embodiment, the perhydrolase catalyst is structurally classified as a cephalosporin C deacetylase. In another embodiment, the perhydrolase catalyst is structurally classified as an acetyl xylan esterase.

In one embodiment, the perhydrolase catalyst comprises an enzyme having a CE-7 signature motif that aligns with a reference sequence SEQ ID NO: 2 using CLUSTALW, said signature motif comprising:

i) an RGQ motif at amino acid positions 118-120 of SEQ ID NO:2;

ii) a GXSQG motif at amino acid positions 179-183 of SEQ ID NO:2; and iii) an HE motif at amino acid positions 298-299 of SEQ ID NO:2;

wherein said enzyme also comprises at least 30% amino acid identity to SEQ ID NO: 2.

In a further embodiment, the signature motif additional comprises a forth conserved motif defined as an LXD motif at amino acid residues 267-269 when aligned to reference sequence SEQ ID NO: 2 using CLUSTALW.

In another embodiment, the perhydrolase catalyst comprises an enzyme having perhydrolase activity selected from the group consisting of SEQ ID NO: 2, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 26, SEQ ID NO: 32, and SEQ ID NO: 70.

In another embodiment, the enzyme catalyst comprises an amino acid sequence selected from the group consisting of SEQ ID NO: 18, SEQ ID NO: 26, and SEQ ID NO: 70 or a substantially similar enzyme having perhydrolase activity derived by substituting, deleting or adding one or more amino acids to said amino acid sequence.

In another embodiment, substantially similar enzyme having perhydrolase activity is at least 95% identical to one or more amino acid sequences selected from the group consisting of SEQ ID NO: 18, SEQ ID NO: 26, and SEQ ID NO: 70.

In a further embodiment, the enzyme having perhydrolase activity is selected from the group consisting of SEQ ID NO: 18, SEQ ID NO: 26, and SEQ ID NO: 70.

In another embodiment, the perhydrolase catalyst comprises an enzyme having an amino acid sequence encoded by a nucleic acid molecule that hybridizes to a nucleic acid sequence selected from the group consisting of SEQ ID NO: 17; SEQ ID NO: 25; SEQ ID NO: 69; and SEQ ID NO: 74 under stringent hybridization conditions.

In another embodiment, the perhydrolase catalyst comprises an enzyme having at least 30%, preferably at last 36%, amino acid identity to a contiguous signature motif defined as SEQ ID NO: 61 wherein the conserved motifs described above (e.g. RGQ, GXSQG, and HE, and optionally, LXD) are conserved.

In one embodiment, suitable substrates include esters provided by the following formula:

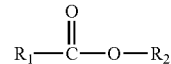

wherein X=an ester group of the formula $R_6C(O)O$ $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;

m=1 to the number of carbon atoms in $R_5$; and wherein said esters have a solubility in water of at least 5 ppm at 25° C.

In another embodiment, suitable substrates also include esters of the formula:

$$R_1-\overset{\displaystyle O}{\underset{\displaystyle \|}{C}}-O-R_2$$

wherein $R_1$=C1 to C7 straight chain or branched chain alkyl optionally substituted with an hydroxyl or a C1 to C4 alkoxy group and $R_2$=C1 to C10 straight chain or branched chain alkyl, alkenyl, alkynyl, aryl, alkylaryl, alkylheteroaryl, heteroaryl, $(CH_2CH_2-O)_nH$ or $(CH_2CH(CH_3)-O)_nH$ and n=1 to 10.

In another embodiment, suitable substrates include glycerides of the formula:

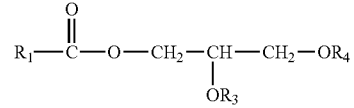

wherein $R_1$=C1 to C7 straight chain or branched chain alkyl optionally substituted with an hydroxyl or a C1 to C4 alkoxy group and $R_3$ and $R_4$ are individually H or $R_1C(O)$.

In another embodiment, $R_6$ is C1 to C7 linear hydrocarbyl moiety, optionally substituted with hydroxyl groups or C1 to C4 alkoxy groups, optionally comprising one or more ether linkages. In a further preferred embodiment, $R_6$ is C2 to C7 linear hydrocarbyl moiety, optionally substituted with hydroxyl groups, and/or optionally comprising one or more ether linkages.

In another embodiment, suitable substrates also include acetylated saccharides selected from the group consisting of acetylated mono-, di-, and polysaccharides. In a preferred embodiment, the acetylated saccharides include acetylated mono-, di-, and polysaccharides. In another embodiment, the acetylated saccharides are selected from the group consisting of acetylated xylan, fragments of acetylated xylan, acetylated xylose (such as xylose tetraacetate), acetylated glucose (such as glucose pentaacetate), β-D-ribofuranose-1,2,3,5-tetraacetate, tri-O-acetyl-D-galactal, and tri-O-acetyl-D-glucal, and acetylated cellulose. In a preferred embodiment, the acetylated saccharide is selected from the group consisting of β-D-ribofuranose-1,2,3,5-tetraacetate, tri-O-acetyl-D-galactal, and tri-O-acetyl-D-glucal, and acetylated cellulose. As such, acetylated carbohydrates may be suitable substrates for generating percarboxylic acids using the present process (i.e., in the presence of a peroxygen source).

In one embodiment, the substrate is selected from the group consisting of: monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol; and mixtures thereof.

In a preferred embodiment, the substrate is selected from the group consisting of ethyl acetate, methyl lactate, ethyl lactate, methyl glycolate, ethyl glycolate, methyl methoxyacetate, ethyl methoxyacetate, methyl 3-hydroxybutyrate, ethyl 3-hydroxybutyrate, triethyl 2-acetyl citrate, glucose pentaacetate, gluconolactone, glycerides (mono-, di-, and triglycerides) such as monoacetin, diacetin, triacetin, monopropionin, dipropionin (glyceryl dipropionate), tripropionin (1,2,3-tripropionylglycerol), monobutyrin, dibutyrin (glyceryl dibutyrate), tributyrin (1,2,3-tributyrylglycerol), acetylated saccharides, and mixtures thereof.

In a further preferred aspect, the carboxylic acid ester substrates are selected from the group consisting of monoacetin, diacetin, triacetin, monopropionin, dipropionin, tripropionin, monobutyrin, dibutyrin, tributyrin, ethyl acetate, and ethyl lactate. In yet another aspect, the carboxylic acid ester substrates are selected from the group consisting of diacetin, triacetin, ethyl acetate, and ethyl lactate. In a preferred aspect, the carboxylic acid ester is a glyceride selected from the group consisting of monoacetin, diacetin, triacetin, and mixtures thereof.

The carboxylic acid ester is present in the reaction mixture at a concentration sufficient to produce the desired concentration of peracid upon enzyme-catalyzed perhydrolysis. The carboxylic acid ester need not be completely soluble in the reaction mixture, but has sufficient solubility to permit conversion of the ester by the perhydrolase catalyst to the corresponding peracid. The carboxylic acid ester is present in the reaction mixture at a concentration of 0.0005 wt % to 40 wt % of the reaction mixture, preferably at a concentration of 0.1 wt % to 20 wt % of the reaction mixture, and more preferably at a concentration of 0.5 wt % to 10 wt % of the reaction mixture. The wt % of carboxylic acid ester may optionally be greater than the solubility limit of the carboxylic acid ester, such that the concentration of the carboxylic acid ester is at least 0.0005 wt % in the reaction mixture that is comprised of water, enzyme catalyst, and source of peroxide, where the remainder of the carboxylic acid ester remains as a second separate phase of a two-phase aqueous/organic reaction mixture. Not all of the added carboxylic acid ester must immediately dissolve in the aqueous reaction mixture, and after an initial mixing of all reaction components, additional continuous or discontinuous mixing is optional.

The peroxygen source may include, but is not limited to, hydrogen peroxide, hydrogen peroxide adducts (e.g., urea-hydrogen peroxide adduct (carbamide peroxide)) perborate salts and percarbonate salts. The concentration of peroxygen compound in the reaction mixture may range from 0.0033 wt % to about 50 wt %, preferably from 0.033 wt % to about 40 wt %, more preferably from 0.33 wt % to about 30 wt %.

Many perhydrolase catalysts (whole cells, permeabilized whole cells, and partially purified whole cell extracts) have been reported to have catalase activity (EC 1.11.1.6). Catalases catalyze the conversion of hydrogen peroxide into oxygen and water. In one aspect, the perhydrolysis catalyst lacks catalase activity. In another aspect, a catalase inhibitor is added to the reaction mixture. Examples of catalase inhibitors include, but are not limited to, sodium azide and hydroxylamine sulfate. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM. In one aspect, sodium azide concentration typically ranges from about 20 mM to about 60 mM while hydroxylamine sulfate is concentration is typically about 0.5 mM to about 30 mM, preferably about 10 mM.

In another embodiment, the enzyme catalyst lacks significant catalase activity or is engineered to decrease or eliminate catalase activity. The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis. In a preferred embodiment, the gene(s) encoding the endogenous catalase activity are down-regulated or disrupted (i.e. knocked-out). As used herein, a "disrupted" gene is one where the activity and/or function of the protein encoded by the modified gene is no longer present. Means to disrupt a gene are well-known in the art and may include, but are not limited to insertions, deletions, or mutations to the gene so long as the activity and/or function of the corresponding protein is no longer present. In a further preferred embodiment, the production host is an E. coli production host comprising a disrupted catalase gene selected from the group consisting of katG (SEQ ID NO: 47) and katE (SEQ ID NO: 56). In another embodiment, the production host is an E. coli strain comprising a down-regulation and/or disruption in both katg1 and a katE catalase genes. An E. coli strain comprising a double-knockout of katG and katE is provided herein (see Example 15; E. coli strain KLP18).

The catalase negative E. coli strain KLP18 (katG and katE double knockout) that was constructed (Example 15) was demonstrated to be a superior host for large scale (10-L and greater) production of perhydrolase enzymes compared to the catalase negative strain UM2 (E. coli Genetic Stock Center #7156, Yale University, New Haven Conn.), as determined by growth under fermenter conditions (Examples 17-19). Although both KLP18 and UM2 are catalase-negative strains, UM2 is known to have numerous nutritional auxotrophies, and therefore requires media that is enriched with yeast extract and peptone. Even when employing enriched media for fermentation, UM2 grew poorly and to a limited maximum cell density (OD). In contrast, KLP18 had no special nutritional requirements and grew to high cell densities on mineral media alone or with additional yeast extract (Example 20).

The concentration of the catalyst in the aqueous reaction mixture depends on the specific catalytic activity of the catalyst, and is chosen to obtain the desired rate of reaction. The weight of catalyst in perhydrolysis reactions typically ranges from 0.0005 mg to 10 mg per mL of total reaction volume, preferably from 0.010 mg to 2.0 mg per mL. The catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, and mixtures thereof.

In one aspect, the concentration of peracid generated by the combination of chemical perhydrolysis and enzymatic perhydrolysis of the carboxylic acid ester is sufficient to provide an effective concentration of peracid for bleaching or disinfection at a desired pH. In another aspect, the present methods provide combinations of enzymes and enzyme substrates to produce the desired effective concentration of peracid, where, in the absence of added enzyme, there is a significantly lower concentration of peracid produced. Although there may in some cases be substantial chemical perhydrolysis of the enzyme substrate by direct chemical reaction of inorganic peroxide with the enzyme substrate, there may not be a sufficient concentration of peracid generated to provide an effective concentration of peracid in the desired applications, and a significant increase in total peracid concentration is achieved by the addition of an appropriate perhydrolase catalyst to the reaction mixture.

The concentration of peracid generated (e.g. peracetic acid) by the perhydrolysis of at least one carboxylic acid ester is at least about 2 ppm, preferably at least 20 ppm, preferably at least 100 ppm, more preferably at least about 200 ppm peracid, more preferably at least 300 ppm, more preferably at least 500 ppm, more preferably at least 700 ppm, more preferably at least about 1000 ppm peracid, most preferably at least 2000 ppm peracid within 10 minutes, preferably within 5 minutes, and most preferably within 1 minute of initiating the perhydrolysis reaction. The product mixture comprising the peracid may be optionally diluted with water, or a solution predominantly comprised of water, to produce a mixture with the desired lower concentration of peracid. In one aspect, the reaction time required to produce the desired concentration of peracid is not greater than about two hours, preferably not greater than about 30 minutes, more preferably not greater than about 10 minutes, even more preferably not greater than about 50 minutes, and most preferably in about 1 minute or less. In other aspects, a hard surface or inanimate object contaminated with a concentration of a microbial population is contacted with the peracid formed in accordance with the processes described herein within about 1 minute to about 168 hours of combining said reaction components, or within about 1 minute to about 48 hours, or within about 1 minute to 2 hours of combining said reaction components, or any such time interval therein.

The temperature of the reaction is chosen to control both the reaction rate and the stability of the enzyme catalyst activity. The temperature of the reaction may range from just above the freezing point of the reaction mixture (approximately 0° C.) to about 75° C., with a preferred range of reaction temperature of from about 5° C. to about 55° C.

The pH of the final reaction mixture containing peracid is from about 2 to about 9, preferably from about 3 to about 8, more preferably from about 5 to about 8, even more preferably about 6 to about 8, and yet even more preferably about 6.5 to about 7.5. In another embodiment, the pH of the reaction mixture is acidic (pH<7). The pH of the reaction, and of the final reaction mixture, may optionally be controlled by the addition of a suitable buffer, including, but not limited to phosphate, pyrophosphate, bicarbonate, acetate, or citrate. The concentration of buffer, when employed, is typically from 0.1 mM to 1.0 M, preferably from 1 mM to 300 mM, most preferably from 10 mM to 100 mM.

In another aspect, the enzymatic perhydrolysis reaction mixture may contain an organic solvent that acts as a dispersant to enhance the rate of dissolution of the carboxylic acid ester in the reaction mixture. Such solvents include, but are not limited to, propylene glycol methyl ether, acetone, cyclohexanone, diethylene glycol butyl ether, tripropylene glycol methyl ether, diethylene glycol methyl ether, propylene glycol butyl ether, dipropylene glycol methyl ether, cyclohexanol, benzyl alcohol, isopropanol, ethanol, propylene glycol, and mixtures thereof.

In another aspect, the enzymatic perhydrolysis product may contain additional components that provide desirable functionality. These additional components include, but are not limited to buffers, detergent builders, thickening agents, emulsifiers, surfactants, wetting agents, corrosion inhibitors (e.g., benzotriazole), enzyme stabilizers, and peroxide stabilizers (e.g., metal ion chelating agents). Many of the additional components are well known in the detergent industry (see for example U.S. Pat. No. 5,932,532; hereby incorporated by reference). Examples of emulsifiers include, but are not limited to polyvinyl alcohol or polyvinylpyrrolidone. Examples of thickening agents include, but are not limited to LAPONITE® RD, corn starch, PVP, CARBOWAX®, CARBOPOL®, CABOSIL®, polysorbate 20, PVA, and lecithin. Examples of buffering systems include, but are not limited to sodium phosphate monobasic/sodium phosphate dibasic; sulfamic acid/triethanolamine; citric acid/triethanolamine; tartaric acid/triethanolamine; succinic acid/triethanolamine; and acetic acid/triethanolamine. Examples of surfactants include, but are not limited to a) non-ionic surfactants such as block copolymers of ethylene oxide or propylene oxide, ethoxylated or propoxylated linear and branched primary and secondary alcohols, and aliphatic phosphine oxides b) cationic surfactants such as quaternary ammonium compounds, particularly quaternary ammonium compounds having a C8-C20 alkyl group bound to a nitrogen atom additionally bound to three C1-C2 alkyl groups, c) anionic surfactants such as alkane carboxylic acids (e.g., C8-C20 fatty acids), alkyl phosphonates, alkane sulfonates (e.g., sodium dodecylsulphate "SDS") or linear or branched alkyl benzene sulfonates, alkene sulfonates and d) amphoteric and zwitterionic surfactants such as aminocarboxylic acids, aminodicarboxylic acids, alkybetaines, and mixtures thereof. Additional components may include fragrances, dyes, stabilizers of hydrogen peroxide (e.g., metal chelators such as 1-hydroxyethylidene-1,1-diphosphonic acid (DEQUEST® 2010, Solutia Inc., St. Louis, Mo. and ethylenediaminetetraacetic acid (EDTA)), TURPINAL® SL, DEQUEST® 0520, DEQUEST® 0531, stabilizers of enzyme activity (e.g., polyethyleneglycol (PEG)), and detergent builders.

In another aspect, the enzymatic perhydrolysis product may be pre-mixed to generate the desired concentration of peroxycarboxylic acid prior to contacting the surface or inanimate object to be disinfected.

In another aspect, the enzymatic perhydrolysis product is not pre-mixed to generate the desired concentration of peroxycarboxylic acid prior to contacting the surface or inanimate object to be disinfected, but instead, the components of the reaction mixture that generate the desired concentration of percarboxylic acid are contacted with the surface or inanimate object to be disinfected, generating the desired concentration of peroxycarboxylic acid.

In Situ Production of Peracids using a Perhydrolase Catalyst

Cephalosporin C deacetylases (E.C. 3.1.1.41; systematic name cephalosporin C acetylhydrolases; CAHs) are enzymes having the ability to hydrolyze the acetyl ester bond on cephalosporins such as cephalosporin C, 7-aminocephalosporanic acid, and 7-(thiophene-2-acetamido)cephalosporanic acid (Abbott, B. and Fukuda, D., *Appl. Microbiol.* 30(3):413-419 (1975)). CAHs belong to a larger family of structurally related enzymes referred to as the carbohydrate esterase family seven (CE-7; see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.)

The CE-7 family includes both CAHs and acetyl xylan esterases (AXEs; E.C. 3.1.1.72). CE-7 family members share a common structural motif and are quite unusual in that they typically exhibit ester hydrolysis activity for both acetylated xylooliogsaccharides and cephalosporin C, suggesting that the CE-7 family represents a single class of proteins with a multifunctional deacetylase activity against a range of small substrates (Vincent et al., *J. Mol. Biol.*, 330:593-606 (2003)). Vincent et al. describes the structural similarity among the members of this family and defines a signature sequence motif characteristic of the CE-7 family.

Members of the CE-7 family are found in plants, fungi (e.g., *Cephalosporidium acremonium*), yeasts (e.g., *Rhodosporidium toruloides, Rhodotorula glutinis*), and bacteria such as *Thermoanaerobacterium* sp.; *Norcardia lactamdurans*, and various members of the genus *Bacillus* (Politino et al., *Appl. Environ. Microbiol.*, 63(12):4807-4811 (1997); Sakai et al., *J. Ferment. Bioeng.* 85:53-57 (1998); Lorenz, W. and Wiegel, J., *J. Bacteriol* 179:5436-5441 (1997); Cardoza et al., *Appl. Microbiol. Biotechnol.*, 54(3):406-412 (2000); Mitshushima et al., supra, Abbott, B. and Fukuda, D., *Appl. Microbiol.* 30(3):413-419 (1975); Vincent et al., supra, Takami et al., *NAR*, 28(21):4317-4331 (2000); Rey et al., *Genome Biol.*, 5(10): article 77 (2004); Degrassi et al., *Microbiology.*, 146:1585-1591 (2000); U.S. Pat. No. 6,645,233; U.S. Pat. No. 5,281,525; U.S. Pat. No. 5,338,676; and WO 99/03984. A non-comprehensive list of CE-7 carbohydrate esterase family members having significant homology to SEQ ID NO: 2 are provided in Table 1.

TABLE 1

Example of CE-7 Enzymes Having Significant Homology to SEQ ID NO: 2.

| Source Organism (GENBANK® Accession No. of the CE-7 enzyme) | Nucleotide Sequence (SEQ ID NO:) | Amino Acid Sequence (SEQ ID NO:) | % Amino Acid Identity to SEQ ID NO: 2. | Reference |
|---|---|---|---|---|
| *B. subtilis* ATCC 31954™ | 1 | 2 | 100 | *B. subtilis* SHS 0133 Mitshushima et al. supra |
| *B. subtilis* subsp. *subtilis* str. 168 (NP_388200) *B. subtilis* BE1010 | 5 | 6 | 98 | Kunst et al., supra. WO99/03984 Payne and Jackson, *J. Bacteriol.* 173: 2278-2282 (1991)) |
| *B. subtilis* ATCC 6633 (YP_077621.1) | 7 | 8 | 96 | U.S. Pat. No. 6,465,233 |
| *B. subtilis* ATCC 29233 | 31 | 32 | 96 | Abbott and Fukuda, supra |
| *B. licheniformis* ATCC 14580 (YP_077621.1) | 9 | 10 | 77 | Rey et al., supra |
| *B. pumilus* PS213 (CAB76451.2) | 11, 60 | 12 | 76 | Degrassi et al., supra |
| *Clostridium thermocellum* ATCC 27405 (ZP_00504991) | 13 | 14 | 57 | Copeland et al. US Dept. of Energy Joint Genome Institute (JGI-PGF) Direct Submission GENBANK® ZP_00504991 |
| *Thermotoga neapolitana* (AAB70869.1) | 15, 41 | 16 | 42 | See GENBANK® AAB70869.1 |
| *Thermotoga maritima* MSB8 (NP_227893.1) | 17, 74 | 18 | 42 | Nelson et al., *Nature* 399 (6734): 323-329 (1999) |
| *Bacillus* sp. NRRL B-14911 (ZP_01168674) | 21 | 22 | 40 | Siefert et al. J. Craig Venter Institute. Direct Submission Under GENBANK® ZP_01168674 |

TABLE 1-continued

Example of CE-7 Enzymes Having Significant Homology to SEQ ID NO: 2.

| Source Organism (GENBANK® Accession No. of the CE-7 enzyme) | Nucleotide Sequence (SEQ ID NO:) | Amino Acid Sequence (SEQ ID NO:) | % Amino Acid Identity to SEQ ID NO: 2. | Reference |
|---|---|---|---|---|
| Thermoanaerobacterium sp. (AAB68821.1) | 19 | 20 | 37 | Lorenz and Wiegel, supra |
| Bacillus halodurans C-125 (NP_244192) | 23 | 24 | 36 | Takami et al., supra |
| Thermoanearobacterium saccharolyticum (S41858) | 69 | 70 | 35 | Lee, Y. E. and Zeikus, J. G., J Gen Microbiol. (1993), 139 Pt 6: 1235-1243 |
| Bacillus clausii KSM-K16 (YP_175265) | 25, 65 | 26 | 33 | Kobayashi et al., Appl. Microbiol. Biotechnol. 43 (3), 473-481 (1995) |

The present perhydrolases are all members of the CE-7 carbohydrate esterase family. As described by Vincent et al. (supra), members of the family share a common signature motif that is characteristic of this family. A CLUSTALW alignment of the present perhydrolases illustrates that all of the members belong to the CE-7 carbohydrate esterase family (FIG. 1, panels A-C). A comparison of the overall percent amino acid identity amount the present perhydrolases is provided in Table 2.

TABLE 2

Percent Amino Acid Identity Between Perhydrolases[1]

| | B. subtilis ATCC 31954 | B. subtilis BE1010 | B. subtilis ATCC 29233 | B. subtilis ATCC 6633 | B. Licheniformis ATCC 14580 | B. pumilus PS213 | C. Thermocellum ATCC 27405 | Thermotoga Neapolitana | Bacillus clausii KSM-K16 | Thermoanaerobacterium saccharolyticum | Thermotoga maritima MSB8 |
|---|---|---|---|---|---|---|---|---|---|---|---|
| B. subtilis ATCC 31954 (SEQ ID NO: 2) | 100 | 98 | 99 | 96 | 77 | 76 | 57 | 42 | 33 | 35 | 42 |
| B. subtilis BE1010 (SEQ ID NO: 6) | 98 | 100 | 99 | 96 | 76 | 77 | 57 | 43 | 33 | 36 | 43 |
| B. subtilis ATCC 29233 (SEQ ID NO: 32) | 99 | 99 | 100 | 96 | 77 | 76 | 57 | 43 | 33 | 35 | 42 |
| B. subtilis ATCC 6633 (SEQ ID NO: 8) | 96 | 96 | 96 | 100 | 76 | 76 | 56 | 43 | 33 | 36 | 42 |
| B. licheniformis ATCC 14580 (SEQ ID NO: 10) | 77 | 76 | 77 | 76 | 100 | 69 | 56 | 45 | 33 | 35 | 45 |
| B. pumilus PS213 (SEQ ID NO: 12) | 76 | 77 | 76 | 76 | 69 | 100 | 57 | 42 | 34 | 36 | 42 |
| Clostridium Thermocellum ATCC 27405 (SEQ ID NO: 14) | 57 | 57 | 57 | 56 | 56 | 57 | 100 | 45 | 34 | 34 | 44 |
| Thermotoga neapolitana (SEQ ID NO: 16) | 42 | 43 | 43 | 43 | 45 | 42 | 45 | 100 | 32 | 34 | 90 |

TABLE 2-continued

Percent Amino Acid Identity Between Perhydrolases[1]

| | B. subtilis ATCC 31954 | B. subtilis BE1010 | B. subtilis ATCC 29233 | B. subtilis ATCC 6633 | B. Licheniformis ATCC 14580 | B. pumilus PS213 | C. Thermocellum ATCC 27405 | Thermotoga Neapolitana | Bacillus clausii KSM-K16 | Thermoanaerobacterium saccharolyticum | Thermotoga maritima MSB8 |
|---|---|---|---|---|---|---|---|---|---|---|---|
| Bacillus clausii KSM-K16 (SEQ ID NO: 26) | 33 | 33 | 33 | 33 | 33 | 34 | 34 | 32 | 100 | 55 | 32 |
| Thermoanaerobacterium saccharolyticum (SEQ ID NO: 70) | 35 | 36 | 35 | 36 | 35 | 36 | 34 | 34 | 55 | 100 | 34 |
| Thermotoga maritima MSB8 (SEQ ID NO: 18) | 42 | 43 | 42 | 42 | 45 | 42 | 44 | 90 | 32 | 34 | 100 |

[1]= Percent identity determined using blast2seq algorithm using BLOSUM62, gap open = 11, gap extension = 1, x_drop = 0, expect = 10, and wordsize = 3. Tatiana A. Tatusova, Thomas L. Madden (1999), "Blast 2 sequences - a new tool for comparing protein and nucleotide sequences", FEMS Microbiol Lett. 174: 247-250

Although variation is observed in terms of overall percent amino acid identity (i.e. the *Clostridium thermocellum* ATCC 27405™ perhydrolase; SEQ ID NO: 14 shares only 57% amino acid identity with the *Bacillus subtilis* ATCC 31954™ perhydrolase; SEQ ID NO: 2, while the *Bacillus clausii* perhydrolase (SEQ ID NO: 26) shares only 33% identity with SEQ ID NO: 2), each of the present perhydrolase enzymes share the CE-7 signature motif. Accordingly, the perhydrolase catalyst of the present invention is an enzyme structurally classified as belonging to the CE-7 carbohydrate esterase family. Each of the present perhydrolase enzymes comprises the CE-7 signature (diagnostic) motif.

Vincent et al. (supra) analyzed the structure CE-7 esterases and has identified several highly conserved motifs that are diagnostic for the family. As shown in FIG. 1, the highly conserved motifs (underlined in FIG. 1; position numbering relative to SEQ ID NO: 2) include the Arg118-Gly119-Gln120 (RGQ), Gly179-Xaa180-Ser181-Gln182-Gly183 (GXSQG), and His298-Glu299 (HE). In addition, FIG. 1 illustrates an additional highly conserved Lys267-Xaa268-Asp269 (LXD) motif that may be used to further characterize the signature motif. All of the numbering is relative to the numbering of a reference sequence (*B. subtilis* ATCC 31954™ perhydrolase; SEQ ID NO: 2).

In one embodiment, suitable perhydrolytic enzymes can be identified by the presence of the CE-7 signature motif (Vincent et al., supra). In a preferred embodiment, perhydrolases comprising the CE-7 signature motif are identified using a CLUSTALW alignment against the *Bacillus subtilis* ATCC 31954 ™ perhydrolase (SEQ ID NO: 2; i.e. the reference sequence used for relative amino acid position numbering). As per the amino acid residue numbering of SEQ ID NO: 2, the CE-7 signature motif comprises 3 conserved motifs defined as:

a) Arg118-Gly119-Gln120;
b) Gly179-Xaa180-Ser181-Gln182-Gly183; and
c) His298-Glu299.

Typically, the Xaa at amino acid residue position 180 is glycine, alanine, proline, or tryptophan. Two of the three amino acid residues belonging to the catalytic triad are in bold. In one embodiment, the Xaa at amino acid residue position 180 is selected from the group consisting of glycine, alanine, proline, and tryptophan.

Further analysis of the conserved motifs within the CE-7 carbohydrate esterase family indicates the presence of an additional conserved motif (LXD at amino acid positions 267-269 of SEQ ID NO: 2) that may be to further define a perhydrolase belonging to the CE-7 carbohydrate esterase family (FIGS. 1a-c). In a further embodiment, the signature motif defined above includes a forth conserved motif defined as:

Leu267-Xaa268-Asp269.

The Xaa at amino acid residue position 268 is typically isoleucine, valine, or methionine. The forth motif includes the aspartic acid residue (bold) that is the third member of the catalytic triad (Ser181-Asp269-His298).

Any number of well-known global alignment algorithms (i.e. sequence analysis software) may be used to align two or more amino acid sequences (representing enzymes having perhydrolase activity) to determine the existence of the present signature motif (for example, CLUSTALW or Needleman and Wunsch (*J. Mol. Biol.*, 48:443-453 (1970)). The aligned sequence(s) is compared to the reference sequence (SEQ ID NO: 2). In one embodiment, a CLUSTAL alignment (CLUSTALW) using a reference amino acid sequence (as used herein the CAH sequence (SEQ ID NO: 2) from the *Bacillus subtilis* ATCC 31954 ™) is used to identify perhydrolases belonging to the CE-7 esterase family. The relative numbering of the conserved amino acid residues is based on the residue numbering of the reference amino acid sequence to account for small insertions or deletions (5 amino acids or less) within the aligned sequence.

A comparison of the overall percent identity among perhydrolases exemplified herein indicates that enzymes having as little as 33% identity to SEQ ID NO: 2 (while retaining the signature motif) exhibit significant perhydrolase activity and are structurally classified as CE-7 carbohydrate esterases. In one embodiment, the present perhydrolases include enzymes comprising the present signature motif and at least 30%, preferably at least 33%, more preferably at least 40%, even more preferably at least 42%, even more preferably at least 50%, even more preferably at least 60%, even more preferably at least 70%, even more preferably at least 80%, even more preferably at least 90%, and most preferably at least 95% amino acid identity to SEQ ID NO: 2.

All of the present perhydrolases are comprised of the above signature motif as shown in Table 3.

TABLE 3

Conserved motifs found within the present enzymes having perhydrolase activity.

| Perhydrolase Sequence | RGQ motif[a] (Residue #s) | GXSQG motif[a] (Residue #s) | LXD motif[b] Residue #s) | HE motif[a] (Residue #s) |
|---|---|---|---|---|
| SEQ ID NO: 2 | 118-120 | 179-183 | 267-269 | 298-299 |
| SEQ ID NO: 6 | 118-120 | 179-183 | 267-269 | 298-299 |
| SEQ ID NO: 8 | 118-120 | 179-183 | 267-269 | 298-299 |
| SEQ ID NO: 10 | 119-121 | 180-184 | 268-270 | 299-300 |
| SEQ ID NO: 12 | 118-120 | 179-183 | 267-269 | 298-299 |
| SEQ ID NO: 14 | 119-121 | 181-185 | 269-271 | 300-301 |
| SEQ ID NO: 16 | 118-120 | 186-190 | 272-274 | 303-304 |
| SEQ ID NO: 18 | 118-120 | 186-190 | 272-274 | 303-304 |
| SEQ ID NO: 26 | 117-119 | 180-184 | 270-272 | 301-302 |
| SEQ ID NO: 32 | 118-120 | 179-183 | 267-269 | 298-299 |
| SEQ ID NO: 70 | 117-119 | 180-184 | 270-272 | 301-302 |

[a] = Conserved motifs defined by Vincent et al., supra used to define the signature motif.
[b] = an additional motif identified herein useful in further defining the signature motif defined by Vincent et al., supra.

Alternatively, a contiguous signature motif (SEQ ID NO: 61) comprising the 4 conserved motifs (RGQ, GXSQG, LXD, and HE; Amino acids residues 118-299 of SEQ ID NO: 2) may also be used as a contiguous signature motif to identify CE-7 carbohydrate esterases (FIG. 1, panels A-C). As such, suitable enzymes expected to have perhydrolase activity may also be identified as having at least 30% amino acid identify, preferably at least 36%, more preferably at least 40%, even more preferably at least 50%, yet more preferably at least 60%, yet even more preferably at least 70%, yet even more preferably at least 80%, yet even more preferably at least 90%, and most preferably at least 95% amino acid identity to SEQ ID NO: 61 (the 4 conserved motifs found in CE-7 carbohydrate esterases are underlined).

(SEQ ID NO: 61)
RGQQSSEDTSISLHGHALGWMTKGILDKDTYYYRGVYLDAVRALEVISSF

DEVDETRIGVTGGSQGGGLTIAAAALSDIPKAAVADYPYLSNFERAIDVA

LEQPYLEINSFFRRNGSPETEVQAMKTLSYFDIMNLADRVKVPVLMSIGL

IDKVTPPSTVFAAYNHLETEKELKVYRYFGHE.

A comparison using the contiguous signature sequence against the present CE-7 esterases having perhydrolase activity is provided in Table 4. BLASTP using default parameters was used.

TABLE 4

Percent Amino Acid Identity of Various CE-7 Carbohydrate Esterases having Perhydrolysis Activity Versus the Contiguous Signature Sequence (SEQ ID NO: 61).

| Perhydrolase Sequence | % Identity using BLASTP | E-score (expected) |
|---|---|---|
| SEQ ID NO: 2 | 100 | 3e−92 |
| SEQ ID NO: 6 | 98 | 6e−91 |
| SEQ ID NO: 8 | 98 | 4e−98 |
| SEQ ID NO: 10 | 78 | 1e−78 |
| SEQ ID NO: 12 | 80 | 3e−76 |
| SEQ ID NO: 14 | 63 | 2e−56 |
| SEQ ID NO: 16 | 51 | 1e−41 |
| SEQ ID NO: 18 | 50 | 6e−35 |

TABLE 4-continued

Percent Amino Acid Identity of Various CE-7 Carbohydrate Esterases having Perhydrolysis Activity Versus the Contiguous Signature Sequence (SEQ ID NO: 61).

| Perhydrolase Sequence | % Identity using BLASTP | E-score (expected) |
|---|---|---|
| SEQ ID NO: 26 | 36 | 7e−21 |
| SEQ ID NO: 32 | 99 | 2e−90 |
| SEQ ID NO: 70 | 40 | 2e−26 |

Alternatively, the percent amino acid identity to the complete length of one or more of the present perhydrolases may also be used. Accordingly, suitable enzymes having perhydrolase activity have at least 30%, preferably at least 33%, preferably at least 40%, preferably at least 40%, more preferably at least 50%, more preferably at least 60%, more preferably at least 70%, even more preferably at least 80%, yet even more preferably at least 90%, and most preferably at least 95% amino acid identity to SEQ ID NO: 2. In a further embodiment, suitable perhydrolase catalysts comprise an amino acid sequence selected from the group consisting of SEQ ID NO: 2, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 26, SEQ ID NO: 32, and SEQ ID NO: 70.

Suitable perhydrolase enzymes may also include enzymes having one or more deletions, substitutions, and/or insertions to one of the present perhydrolase enzymes (e.g. SEQ ID NOs 2, 6, 8, 10, 12, 14, 16, 18, 26, 32, and 70). As shown in Table 2, CE-7 carbohydrates esterases having perhydrolase activity share as little as 32% overall amino acid identity. Based on the data provided in the present examples, additional enzymes having perhydrolase activity belonging to the CE-7 carbohydrate esterase family may have even lower percent identity, so long as the enzyme retains the conserved signature motif. As such, the numbers of deletions, substitutions, and/or insertions may vary so long as the conserved signature motifs (see Table 3) are found in their relative positions within the enzyme.

Additionally, it is well within one of skill in the art to identity suitable enzymes according to the structural similarity found within the corresponding nucleic acid sequence. Hybridization techniques can be used to identity similar gene sequences. Accordingly, suitable perhydrolase catalysts of the present invention comprise an amino acid sequence encoded by a nucleic acid molecule that hybridizes under stringent conditions to a nucleic acid molecule having a nucleic acid sequence selected from the group consisting of SEQ ID NO: 1, SEQ ID NO: 5, SEQ ID NO: 7, SEQ ID NO: 9, SEQ ID NO: 11, SEQ ID NO: 13, SEQ ID NO: 15, SEQ ID NO: 17; SEQ ID NO: 25; SEQ ID NO: 31, SEQ ID NO: 41, SEQ ID NO: 60, SEQ ID NO: 65, SEQ ID NO: 69, and SEQ ID NO: 74.

The present method produces industrially-useful, efficacious concentrations of peracids in situ under aqueous reaction conditions using the perhydrolase activity of an enzyme belonging to the CE-7 family of carbohydrate esterases. In one embodiment, the enzyme having perhydrolase activity is also classified structurally and functionally as a cephalosporin C deacetylase (CAH). In another embodiment, the enzyme having perhydrolase activity is classified structurally and functionally as an acetyl xylan esterase (AXE).

The peracids produced are quite reactive and may decrease in concentration over extended periods of time, depending on variables that include, but are not limited to, temperature and pH. As such, it may be desirable to keep the various reaction components separated, especially for liquid formulations. In one aspect, the hydrogen peroxide source is separate from either the substrate or the perhydrolase catalyst, preferably from both. This can be accomplished using a variety of techniques including, but not limited to the use of multicompartment chambered dispensers (U.S. Pat. No. 4,585,150) and at the time of use physically combining the perhydrolase catalyst with an inorganic peroxide and the present substrates to initiate the aqueous enzymatic perhydrolysis reaction. The perhydrolase catalyst may optionally be immobilized within the body of reaction chamber or separated (e.g. filtered, etc.) from the reaction product comprising the peracid prior to contacting the surface and/or object targeted for treatment. The perhydrolase catalyst may be in a liquid matrix or in a solid form (i.e. powdered, tablet) or embedded within a solid matrix that is subsequently mixed with the substrates to initiate the enzymatic perhydrolysis reaction. In a further aspect, the perhydrolase catalyst may be contained within a dissolvable or porous pouch that may be added to the aqueous substrate matrix to initiate enzymatic perhydrolysis. In an additional further aspect, a powder comprising the enzyme catalyst is suspended in the substrate (e.g., triacetin), and at time of use is mixed with a source of peroxygen in water.

HPLC Assay Method for Determining the Concentration of Peracid and Hydrogen Peroxide.

A variety of analytical methods can be used in the present method to analyze the reactants and products including, but not limited to titration, high performance liquid chromatography (HPLC), gas chromatography (GC), mass spectroscopy (MS), capillary electrophoresis (CE), the analytical procedure described by U. Karst et al., (*Anal. Chem.,* 69(17): 3623-3627 (1997)), and the 2,2'-azino-bis(3-ethylbenzothazoline)-6-sulfonate (ABTS) assay (S. Minning, et al., *Analytica Chimica Acta* 378:293-298 (1999) and WO 2004/058961 A1) as described in the present examples.

Determination of Minimum Biocidal Concentration of Peracids

The method described by J. Gabrielson, et al. (*J. Microbiol. Methods* 50: 63-73 (2002)) can be employed for determination of the Minimum Biocidal Concentration (MBC) of peracids, or of hydrogen peroxide and enzyme substrates. The assay method is based on XTT reduction inhibition, where XTT ((2,3-bis[2-methoxy-4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to viable plate counts, direct microscopic counts, dry weight, turbidity measurements, absorbance, and bioluminescence (see, for example Brock, Semour S., *Disinfection, Sterilization, and Preservation,* 5$^{th}$ edition, Lippincott Williams & Wilkins, Philadelphia, Pa., USA; 2001).

Uses of Enzymatically-Prepared Peracid Compositions

The enzyme catalyst-generated peracid produced according to the present methods can be used in a variety of hard surface/inanimate object applications for reduction of concentrations of microbial, fungal, prion-related, and viral contamination, such as decontamination of medical instruments (e.g., endoscopes), textiles (e.g., garments, carpets), food preparation surfaces, food storage and food-packaging equipment, materials used for the packaging of food products, chicken hatcheries and grow-out facilities, animal enclosures, and spent process waters that have microbial and/or virucidal activity. The enzyme-generated peracids may be used in formulations designed to inactivate prions (e.g. certain proteases) to additionally provide biocidal activity. In a preferred aspect, the present peracid compositions are particularly useful as a disinfecting agent for non-autoclavable medical instruments and food packaging equipment. As the peracid-containing formulation may be prepared using GRAS or food-grade components (enzyme, enzyme substrate, hydrogen peroxide, and buffer), the enzyme-generated peracid may also be used for decontamination of animal carcasses, meat, fruits and vegetables, or for decontamination of prepared foods. The enzyme-generated peracid may be incorporated into a product whose final form is a powder, liquid, gel, film, solid or aerosol. The enzyme-generated peracid may be diluted to a concentration that still provides an efficacious decontamination.

The compositions comprising an efficacious concentration of peracid can be used to disinfect surfaces and/or objects contaminated (or suspected of being contaminated) with viable pathogenic microbial contaminants by contacting the surface or object with the products produced by the present processes. As used herein, "contacting" refers to placing a disinfecting composition comprising an effective concentration of peracid in contact with the surface or inanimate object suspected of contamination with a disease-causing entity for a period of time sufficient to clean and disinfect. Contacting includes spraying, treating, immersing, flushing, pouring on or in, mixing, combining, painting, coating, applying, affixing to and otherwise communicating a peracid solution or composition comprising an efficacious concentration of peracid, or a solution or composition that forms an efficacious concentration of peracid, with the surface or inanimate object suspected of being contaminated with a concentration of a microbial population. The disinfectant compositions may be combined with a cleaning composition to provide both cleaning and disinfection. Alternatively, a cleaning agent (e.g., a surfactant or detergent) may be incorporated into the formulation to provide both cleaning and disinfection in a single composition.

The compositions comprising an efficacious concentration of peracid can also contain at least one additional antimicrobial agent, combinations of prion-degrading proteases, a virucide, a sporicide, or a biocide. Combinations of these agents with the peracid produced by the claimed processes can provide for increased and/or synergistic effects when used to clean and disinfect surfaces and/or objects contaminated (or suspected of being contaminated) with pathogenic microorganisms, spores, viruses, fungi, and/or prions. Suitable antimicrobial agents include carboxylic esters (e.g., p-hydroxy alkyl benzoates and alkyl cinnamates), sulfonic acids (e.g., dodecylbenzene sulfonic acid), iodo-compounds or active halogen compounds (e.g., elemental halogens, halogen oxides (e.g., NaOCl, HOCl, HOBr, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$-$C_6$ alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection. Effective amounts of antimicrobial agents include about 0.001 wt % to about 60 wt % antimicrobial agent, about 0.01 wt % to about 15 wt % antimicrobial agent, or about 0.08 wt % to about 2.5 wt % antimicrobial agent.

In one aspect, the peracids formed by the present process can be used to reduce the concentration of viable microbial contaminants (e.g. a viable microbial population) when applied on and/or at a locus. As used herein, a "locus" of the invention comprises part or all of a target surface suitable for disinfecting or bleaching. Target surfaces include all surfaces that can potentially be contaminated with microorganisms, viruses, spores, fungi, prions or combinations thereof. Non-limiting examples include equipment surfaces found in the food or beverage industry (such as tanks, conveyors, floors, drains, coolers, freezers, equipment surfaces, walls, valves, belts, pipes, drains, joints, crevasses, combinations thereof, and the like); building surfaces (such as walls, floors and windows); non-food-industry related pipes and drains, including water treatment facilities, pools and spas, and fermentation tanks; hospital or veterinary surfaces (such as walls, floors, beds, equipment, (such as endoscopes) clothing worn in hospital/veterinary or other healthcare settings, including clothing, scrubs, shoes, and other hospital or veterinary surfaces); restaurant surfaces; bathroom surfaces; toilets; clothes and shoes; surfaces of barns or stables for livestock, such as poultry, cattle, dairy cows, goats, horses and pigs; hatcheries for poultry or for shrimp; and pharmaceutical or biopharmaceutical surfaces (e.g., pharmaceutical or biopharmaceutical manufacturing equipment, pharmaceutical or biopharmaceutical ingredients, pharmaceutical or biopharmaceutical excipients). Additional hard surfaces also include food products, such as beef, poultry, pork, vegetables, fruits, seafood, combinations thereof, and the like. The locus can also include water absorbent materials such as infected linens or other textiles. The locus also includes harvested plants or plant products including seeds, corms, tubers, fruit, and vegetables, growing plants, and especially crop growing plants, including cereals, leaf vegetables and salad crops, root vegetables, legumes, berried fruits, citrus fruits and hard fruits.

Non-limiting examples of hard surface materials are metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth)acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon). Additional surfaces include brick, tile, ceramic, porcelain, wood, vinyl, linoleum, and carpet.

Recombinant Microbial Expression

The genes and gene products of the instant sequences may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The perhydrolase may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to bacterial, fungal or yeast species such as *Aspergillus*, *Trichoderma*, *Saccharomyces*, *Pichia*, *Phaffia*, *Candida*, *Hansenula*, *Yarrowia*, *Salmonella*, *Bacillus*, *Acinetobacter*, *Zymomonas*, *Agrobacterium*, *Erythrobacter*, *Chlorobium*, *Chromatium*, *Flavobacterium*, *Cytophaga*, *Rhodobacter*, *Rhodococcus*, *Streptomyces*, *Brevibacterium*, *Corynebacteria*, *Mycobacterium*, *Deinococcus*, *Escherichia*, *Erwinia*, *Pantoea*, *Pseudomonas*, *Sphingomonas*, *Methylomonas*, *Methylobacter*, *Methylococcus*, *Methylosinus*, *Methylomicrobium*, *Methylocystis*, *Alcaligenes*, *Synechocystis*, *Synechococcus*, *Anabaena*, *Thiobacillus*, *Methanobacterium*, *Klebsiella*, and *Myxococcus*. In one embodiment, bacterial host strains include *Escherichia*, *Bacillus*, and *Pseudomonas*. In a preferred embodiment, the bacterial host cell is *Escherichia coli*.

Large-scale microbial growth and functional gene expression may use a wide range of simple or complex carbohydrates, organic acids and alcohols or saturated hydrocarbons, such as methane or carbon dioxide in the case of photosynthetic or chemoautotrophic hosts, the form and amount of nitrogen, phosphorous, sulfur, oxygen, carbon or any trace micronutrient including small inorganic ions. The regulation of growth rate may be affected by the addition, or not, of specific regulatory molecules to the culture and which are not typically considered nutrient or energy sources.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell and/or native to the production host, although such control regions need not be so derived.

Initiation control regions or promoters, which are useful to drive expression of the present cephalosporin C deacetylase coding region in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred host cell. In one embodiment, the inclusion of a termination control region is optional. In another embodiment, the chimeric gene includes a termination control region derived the preferred host cell.

Industrial Production

A variety of culture methodologies may be applied to produce the present perhydrolase catalysts. For example, large-scale production of a specific gene product overexpressed from a recombinant microbial host may be produced by both batch and continuous culture methodologies.

A classical batch culturing method is a closed system where the composition of the media is set at the beginning of the culture and not subject to artificial alterations during the culturing process. Thus, at the beginning of the culturing process, the media is inoculated with the desired organism or organisms and growth or metabolic activity may occur without adding anything further to the system. Typically, however, a "batch" culture is batch with respect to the addition of carbon source and attempts are often made to control factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the fed-batch system. Fed-batch culture processes are also suitable in the present invention and comprise a typical batch system except that the substrate is added in increments as the culture progresses. Fed-batch systems are useful when catabolite repression is apt to inhibit the metabolism of the cells and where it is desirable to have limited amounts of substrate in the media. Measurement of the actual substrate concentration in fed-batch systems is difficult and is estimated on the basis of the changes of measurable factors such as pH, dissolved oxygen and the partial pressure of waste gases such as $CO_2$. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem. Biotechnol.*, 36:227 (1992).

Commercial production of the desired perhydrolase catalysts may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, disaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as carbon dioxide, methane or methanol (for example, when the host cell is a methylotrophic microorganism). Similarly, various species of *Candida* will metabolize alanine or oleic acid (Sulter et al., *Arch. Microbiol.*, 153:485-489 (1990)). Hence, it is contemplated that the source of carbon utilized in the present invention may encompass a wide variety of carbon-containing substrates and will only be limited by the choice of organism.

Recovery of the desired perhydrolase catalysts from a batch or fed batch fermentation, or continuos culture, may be accomplished by any of the methods that are known to those skilled in the art. For example, when the perhydrolase catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired perhydrolase catalyst. The cell extract may optionally be filtered through an appropriate filter aid such as celite or silica to remove cell debris prior to a heat-treatment step to precipitate undesired protein from the perhydrolase catalyst solution. The solution containing the desired perhydrolase catalyst may then be separated from the precipitated cell debris and protein by membrane filtration or centrifugation, and the resulting partially-purified perhydrolase catalyst solution concentrated by additional membrane filtration, then optionally mixed with an appropriate carrier (for example, maltodextrin, phosphate buffer, citrate buffer, or mixtures thereof) and spray-dried to produce a solid powder comprising the desired perhydrolase catalyst.

Applicants specifically incorporate the entire contents of all cited references in this disclosure. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

General Methods

The following examples are provided to demonstrate preferred aspects of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma/Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "µL" means microliters, "mL" means milliliters, "L" means liters, "mM" means millimolar, "M" means molar, "mmol" means millimole(s), "ppm" means parts per million, "wt" means weight, "wt %" means weight percent, "g" means grams, "µg" means micrograms, "g" means gravity, "HPLC" means high performance liquid chromatography, "dd $H_2O$" means distilled and deionized water, "dcw" means dry cell weight, "ATCC" or "ATCC®" means the American Type Culture Collection (Manassas, Va.), "U" means units of perhydrolase activity, "rpm" means revolutions per minute, and "EDTA" means ethylenediaminetetraacetic acid.

Example 1

Growth of Bacillus subtilis ATCC 31954™ and Preparation of Cell Extract

A culture of Bacillus subtilis (ATCC 31954™) was revived following suspension of the dried culture in 5 mL of nutrient broth (DIFCO; 0003-01-6) and incubation for 3 days at 30° C. Following the third day of incubation, an aliquot of the culture was streaked onto a trypticase soy agar culture plate (Becton, Dickinson, and Company; Franklin Lakes, N.J.) and incubated at 35° C. for 24 h. Several single colonies were scraped onto a 1 microliter inoculation loop (Becton Dickinson; catalog #220215) and transferred into 50 mL of Lactobacillus MRS broth (Hardy Diagnostics, Santa Maria, Calif.; catalog #C5931). The culture was then grown at 30° C. and a 200-rpm agitation rate for 12 h. After 12 h of growth, 2 mL of the culture was transferred into an unbaffled 500-mL shake flask containing 100 mL of MRS broth for growth at 30° C. and 200-rpm agitation for 12-14 h. The cells were subsequently harvested by centrifugation at 15,000×g for 25 min at 5° C. and the resulting cell paste stored at −80° C.

For cell extract preparation, 0.9 g of cell paste was suspended at 25 wt % (wet cell weight) in 0.05 M potassium phosphate buffer (pH 7.0) containing dithiothreitol (1 mM) and EDTA (1 mM). The cell suspension was passed twice through a French press having a working pressure of 16,000 psi. The crude extract was then centrifuged at 20,000×g to remove cellular debris, producing a clear cell extract that was assayed for total soluble protein (Bicinchoninic Acid Kit for Protein Determination, Sigma Aldrich, Sigma catalog #BCA1-KT), then frozen and stored at −80° C.

Example 2

Determination of Perhydrolysis Activity of Bacillus subtilis ATCC 31954™ Semi-Purified Cell Extract A 1.0-mL aliquot of Bacillus subtilis (ATCC 31954™) cell extract (10 mg total protein/mL, prepared as described in Example 1) was diluted with an equal volume of 50 mM phosphate buffer (pH 7.0) and filtered through a 100,000 Molecular Weight Cutoff (MWCO) Centricon membrane unit (Millipore Corp, Bedford, Mass.). The resulting filtrate (semi-purified cell extract) contained 1.5 mg total protein/mL assayed for total soluble protein (Bicinchoninic Acid Kit for Protein Determination, Sigma catalog #BCA1-KT), and an assay of this filtrate indicated no measurable catalase activity.

A 1-mL reaction mixture containing triacetin (250 mM), hydrogen peroxide (2.5 M) and 0.100 mL of semi-purified cell extract (0.15 mg extract total protein) in 50 mM phosphate buffer (pH 6.5) was mixed at 25° C. A control reaction was run by substituting 50 mM phosphate buffer (pH 6.5) for semi-purified cell extract to determine the concentration of peracetic acid produced by chemical perhydrolysis of triacetin by hydrogen peroxide in the absence of added semi-purified cell extract.

Determination of the concentration of peracetic acid in the reaction mixture was performed according to the method described by Karst et al. Aliquots (0.250 mL) of the reaction mixture were removed at 10 min and 30 min and filtered using an Ultrafree® MC-filter unit (30,000 Normal Molecular Weight Limit (NMWL), Millipore cat #UFC3LKT 00) by centrifugation for 2 min at 12,000 rpm; removal of the protein component of the aliquot by filtration terminated the reaction. An aliquot (0.100 mL) of the resulting filtrate was transferred to 1.5-mL screw cap HPLC vial (Agilent Technologies, Palo Alto, Calif.; #5182-0715) containing 0.300 mL of deionized water, then 0.100 mL of 20 mM MTS (methyl-p-tolyl-sulfide) in acetonitrile was added, the vials capped, and the contents briefly mixed prior to a 10 min incubation at ca. 25° C. in the absence of light. To each vial was then added 0.400 mL of acetonitrile and 0.100 mL of a solution of triphenylphosphine (TPP, 40 mM) in acetonitrile, the vials re-capped, and the resulting solution mixed and incubated at ca. 25° C. for 30 min in the absence of light. To each vial was then added 0.100 mL of 10 mM N,N-diethyl-m-toluamide (DEET; HPLC external standard) and the resulting solution analyzed by HPLC as described below. The peracetic acid concentrations produced in 10 min and 30 min are listed in Table 5.

HPLC Method:

Supelco Discovery C8 column (10-cm×4.0-mm, 5 µm) (cat. #569422-U) w/precolumn Supelco Supelguard Discovery C8 (Sigma-Aldrich; cat #59590-U); 10 microliter injection volume; gradient method with $CH_3CN$ (Sigma-Aldrich; #270717) and deionized $H_2O$ at 1.0 mL/min and ambient temperature:

| Time (min:sec) | (% $CH_3CN$) |
|---|---|
| 0:00 | 40 |
| 3:00 | 40 |
| 3:10 | 100 |
| 4:00 | 100 |

-continued

| Time (min:sec) | (% CH$_3$CN) |
|---|---|
| 4:10 | 40 |
| 7:00 (stop) | 40 |

TABLE 5

Peracetic acid (PAA) produced by reaction of triacetin (250 mM) and hydrogen peroxide (2.5M) at pH 6.5 in the presence or absence of *B. subtilis* (ATCC 31954 ™) semi-purified cell extract.

| *B. subtilis* (ATCC 31954 ™) semi-purified cell extract (mg total protein/mL) | peracetic acid (ppm) in 10 min | peracetic acid (ppm) in 30 min |
|---|---|---|
| 0 | 641 | 1343 |
| 0.15 | 3492 | 3032 |

Example 3

Perhydrolysis Activity of Semi-Purified Enzyme from *Bacillus subtilis* ATCC 31954™ Cell Extract

*Bacillus subtilis* ATCC 31954™ growth and extract preparation was performed as described in Example 1, except that the crude extract was not centrifuged. The crude extract was fractionated with cold n-propanol (−20° C.). A flask containing the cell-free extract was stirred in an ice bath for 15 min, then the n-propanol (−20° C.) was added drop-wise (to prevent freezing of the extract) to a concentration of 40% (v/v). The resulting extract/propanol mixture was stirred in the ice bath for 30 min, then centrifuged at 12,000×g for 10 min at 5° C., and the supernatant returned to the flask and placed into the ice bath. Additional n-propanol (−20° C.) was slowly added to the supernatant with stirring to a concentration of 60% (v/v), and the resulting mixture stirred for 30 min in the ice bath and then centrifuged as before. The pellet from this second fraction was saved on ice and the supernatant returned to the flask and placed into the ice bath. Cold n-propanol was slowly added to the supernatant with stirring to a concentration of 80% (v/v), the mixture stirred for 30 min and centrifuged as before. The pellet from the 60-80% fraction was saved on ice. The pellets from the 40-60% (v/v) n-propanol fractions and the 60-80% (v/v) n-propanol fractions were dissolved in a minimum amount of 0.05 M phosphate buffer (pH 6.5) and the resulting solutions assayed for total soluble protein (Bicinchoninic Acid Kit for Protein Determination, catalog #BCA1-KT), then frozen and stored at −80° C.

A 1-mL reaction mixture containing triacetin (250 mM), hydrogen peroxide (1.0 M) and 0.10 mg/mL of total soluble protein from either the 40-60% (v/v) or 60-80% (v/v) n-propanol fractions of the cell extract (prepared as described above) in 50 mM phosphate buffer (pH 6.5) was mixed at 25° C. A control reaction was run by substituting 50 mM phosphate buffer (pH 6.5) for the n-propanol fractions of the cell extract containing semi-purified enzyme to determine the concentration of peracetic acid produced by chemical perhydrolysis of triacetin by hydrogen peroxide in the absence of added semi-purified enzyme. The reaction mixture was assayed for peracetic acid at 5 min and 30 min using the procedure described in Example 2, and the concentrations of peracetic acid produced by added enzyme are listed in Table 6.

TABLE 6

Peracetic acid (PAA) produced by reaction of triacetin (250 mM) and hydrogen peroxide (1.0M) at pH 6.5 in the presence or absence of *B. subtilis* (ATCC 31954 ™) semi-purified cell extracts.

| n-propanol fraction of cell extract | total protein (mg/mL reaction) | peracetic acid (ppm) in 5 min | peracetic acid (ppm) in 30 min |
|---|---|---|---|
| no extract | 0 | 221 | 803 |
| 40-60% | 0.1 | 2829 | 4727 |
| 60-80% | 0.1 | 1832 | 3777 |

Example 4

Identification of a Cephalosporin C Deacetylase Having Perhydrolysis Activity from *Bacillus subtilis* ATCC 31954™ Cell Extract A 0.1 mL sample (500 μg total protein) of the 40-60% n-propanol fraction described in Example 3 was mixed at room temperature with an equal volume of 2× non-denaturing (native) sample buffer (Invitrogen) and loaded into the preparative sample well of a 1.5 mm 8-16% Tris-Glycine polyacrylamide mini-gel (2D gels; Invitrogen). The native gel electrophoresis was operated at 125 V for 90 min using Tris-Glycine running buffer (Invitrogen). Following electrophoresis, the gel was prepared for an in situ esterase activity assay using the pH indicator, bromothymol blue.

The gel was washed for 10 min×2 with deionized water and slow mechanical mixing. The gel was then washed for 10 min using 10 mM phosphate buffer. Following the removal of the phosphate buffer, 50 mL of 10 mM phosphate buffer containing 665 μL of saturated bromothymol blue (in water) was incubated with the gel for 10 min followed by the addition of 1 mL of neat triacetin (Sigma Aldrich). Within 10 min of incubation one yellow band at 146 kDa appeared on the gel indicating esterase activity.

The esterase-positive band was excised from the gel and transferred into a 50 mL polypropylene conical tube (Falcon). The yellow bromothymol blue stain was removed from the gel slice following two 5-mL deionized water washes with gentle mixing. The gel slice was then treated for 30 min with 0.9 mL of 2× Novex Tris-Glycine SDS sample buffer plus 100 μL of 10× NuPAGE reducing agent (Invitrogen) with gentle mixing. Following the sample treatment, the gel slice and sample buffer were incubated at 85° C. for 5 min using a hot water bath. The gel slice was then removed from the incubation tube and carefully placed in the single preparative well of a 1.5 mm 8-16% Tris-Gly mini-gel. Care was taken to exclude air bubbles and to have direct contact with the stacking gel. The gel slice was then immobilized in place following the addition of 250-300 μL of a warm 0.5% agarose solution prepared in deionized water into the preparative well. The single molecular marker lane was loaded with 15 μL of See-Blue® Plus2 pre-stained MW marker (Invitrogen).

The electrophoresis of the gel slice was operated at 30 V for 30 min for electro-elution of the protein from the gel slice into the slab gel. The voltage was then ramped up from 30 V to 125 V over 10 min followed by 90 min operation at 125 V. Following electrophoresis, the resolved protein bands on the gel were blotted onto a PVDF membrane as described in the XCell II™ blotting manual (Invitrogen) and the blotting buffer was 10 mM CAPS, pH 11.0. The electro-blotting procedure was operated at 25 V for 2 hr at room temperature with ice water in the jacket of the transfer apparatus.

Following the transfer, the PVDF membrane was stained with ProBlot staining solution (Applied Biosystems, Foster City, Calif.) for 1 min followed by de-staining with methanol:water (50:50). Six protein bands were identified and each was N-terminal sequenced. Following a Blast search of the GenBank® amino acid sequence database, the only band having esterase-related sequence homology was identified as Band 1 and the 17 N-terminal amino acid calls had 100% amino acid identity to a *Bacillus subtilis* cephalosporin C deacetylase (GENBANK® BAA01729; Mitsushima et al., supra; U.S. Pat. No. 5,528,152; and U.S. Pat. No. 5,338,676).

Example 5

Cloning and Expression of Perhydrolase from *Bacillus subtilis* ATCC 31954™

Genomic DNA was isolated from *Bacillus subtilis* ATCC 31954 ™ using the PUREGENE® DNA purification system (Gentra Systems, Minneapolis Minn.). The perhydrolase gene was amplified from the genomic DNA by PCR (0.5 min at 94° C., 0.5 min at 55° C., 1 min at 70° C., 30 cycles) using primers identified as SEQ ID NO: 3 and SEQ ID NO: 4. The resulting nucleic acid product (SEQ ID NO: 1) was subcloned into pTrcHis2-TOPO® (Invitrogen, Carlsbad Calif.) to generate the plasmid identified as pSW186. The perhydrolase gene was also amplified from the genomic DNA by PCR (0.5 min at 94° C., 0.5 min at 55° C., 1 min at 70° C., 30 cycles) using primers identified as SEQ ID NO: 27 and SEQ ID NO: 28. The resulting nucleic acid product (SEQ ID NO: 29) was cut with restriction enzymes PstI and XbaI and subcloned between the PstI and XbaI sites in pUC19 to generate the plasmid identified as pSW194. The plasmids pSW186 and pSW194 were used to transform *E. coli* TOP10 (Invitrogen, Carlsbad Calif.), *E. coli* MG1655 (ATCC 47076™), *E. coli* UM2 (*E. coli* Genetic Stock Center #7156, Yale University, New Haven Conn.) and *E. coli* KLP18 (see EXAMPLE 15) to generate the strains identified as TOP10/pSW186, MG1655/pSW186, UM2/pSW186, KLP18/pSW186, TOP10/pSW194, MG1655/pSW194, UM2/pSW194 and KLP18/pSW194, respectively. TOP10/pSW186, MG1655/pSW186, UM2/pSW186, KLP18/pSW186, TOP10/pSW194, MG1655/pSW194, UM2/pSW194 and KLP18/pSW194 were gown in LB media at 37° C. with shaking up to $OD_{600\,nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 6

Cloning and Expression of Perhydrolase from *Bacillus subtilis* BE1010

Genomic DNA was isolated from *Bacillus subtilis* BE1010 (Payne and Jackson 1991 *J. Bacteriol.* 173:2278-2282) using the PUREGENE® DNA purification system (Gentra Systems). The perhydrolase gene was amplified from the genomic DNA by PCR (0.5 min at 94° C., 0.5 min at 55° C., 1 min at 70° C., 30 cycles) using primers identified as SEQ ID NO: 3 and SEQ ID NO: 4. The resulting nucleic acid product (SEQ ID NO: 5) was subcloned into pTrcHis2-TOPO® (Invitrogen) to generate the plasmid identified as pSW187. The perhydrolase gene was also amplified from the genomic DNA by PCR (0.5 min at 94° C., 0.5 min at 55° C., 1 min at 70° C., 30 cycles) using primers identified as SEQ ID NO: 27 and SEQ ID NO: 28. The resulting nucleic acid product (SEQ ID NO: 30) was cut with restriction enzymes PstI and XbaI and subcloned between the PstI and XbaI sites in pUC1 g to generate the plasmid identified as pSW189. The plasmids pSW187 and pSW189 were used to transform *E. coli* TOP10 (Invitrogen), *E. coli* MG1655 (ATCC 47076™), *E. coli* UM2 (*E. coli* Genetic Stock Center #7156, Yale University, New Haven Conn.) and *E. coli* KLP18 (see EXAMPLE 15) to generate the strains identified as TOP10/pSW187, MG1655/pSW187, UM2/pSW187, KLP18/pSW187, TOP10/pSW189, MG1655/pSW189, UM2/pSW189 and KLP18/pSW19, respectively. TOP10/pSW187, MG1655/pSW187, UM2/pSW187, KLP18/pSW187, TOP10/pSW189, MG1655/pSW189, UM2/pSW189 and KLP18/pSW189 were gown in LB media at 37° C. with shaking up to $OD_{600\,nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 7

Cloning and Expression of Perhydrolase from *Bacillus subtilis* ATCC 6633™

Genomic DNA was isolated from *Bacillus subtilis* ATCC 6633™ using the PUREGENE® DNA purification system. The perhydrolase gene was amplified from the genomic DNA by PCR (0.5 min at 94° C., 0.5 min at 55° C., 1 min at 70° C., 30 cycles) using primers identified as SEQ ID NO: 3 and SEQ ID NO: 4. The resulting nucleic acid product (SEQ ID NO: 7) was subcloned into pTrcHis2-TOPO® to generate the plasmid identified as pSW188. The plasmid pSW188 was used to transform *E. coli* MG1655 (ATCC 47076™) and *E. coli* UM2 (*E. coli* Genetic Stock Center #7156, Yale University, New Haven Conn.) to generate the strains identified as MG1655/pSW188 and UM2/pSW188, respectively. MG1655/pSW188 and UM2/pSW188 were gown in LB media at 37° C. with shaking up to $OD_{600\,nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 8

Cloning and Expression of Perhydrolase from *Bacillus subtilis* ATCC 29233™

Genomic DNA was isolated from *Bacillus subtilis* ATCC 29233™ using the PUREGENE® DNA purification system. The perhydrolase gene was amplified from the genomic DNA by PCR (0.5 min at 94° C., 0.5 min at 55° C., 1 min at 70° C., 30 cycles) using primers identified as SEQ ID NO: 3 and SEQ ID NO: 4. The resulting nucleic acid product (SEQ ID NO: 31) was subcloned into pTrcHis2-TOPO® to generate the plasmid identified as pSW190. The plasmid pSW190 was used to transform *E. coli* MG1655 (ATCC 47076™), *E. coli* UM2 (*E. coli* Genetic Stock Center #7156, Yale University, New Haven Conn.) and *E. coli* KLP18 (see EXAMPLE 15) to generate the strains identified as MG1655/pSW190, UM2/pSW190 and KLP18/pSW190, respectively. MG1655/pSW190, UM2/pSW190 and KLP18/pSW190 were gown in LB media at 37° C. with shaking up to $OD_{600\,nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 9

Cloning and Expression of Perhydrolase from *Bacillus licheniformis* ATCC 14580™

Genomic DNA was isolated from *Bacillus licheniformis* ATCC 14580™ using the PUREGENE® DNA purification system. The perhydrolase gene was amplified from the genomic DNA by PCR (0.5 min at 94° C., 0.5 min at 55° C., 1 min at 70° C., 30 cycles) using primers identified as SEQ ID NO: 33 and SEQ ID NO: 34. The resulting nucleic acid product (SEQ ID NO: 9) was subcloned into pTrcHis2-TOPO® to generate the plasmid identified as pSW191. The plasmid pSW191 was used to transform *E. coli* MG1655 (ATCC 47076™), *E. coli* UM2 (*E. coli* Genetic Stock Center #7156, Yale University, New Haven Conn.), *E. coli* PIR1 (Invitrogen, Carlsbad Calif.) and *E. coli* KLP18 (see EXAMPLE 15) to generate the strains identified as MG1655/pSW191, UM2/pSW191, PIR1/pSW191 and KLP18/pSW191, respectively. MG1655/pSW191, UM2/pSW191, PIR1/pSW191 and KLP18/pSW191 were gown in LB media at 37° C. with shaking up to $OD_{600\ nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 10

Cloning and Expression of Perhydrolase from *Clostridia thermocellum* ATCC 27405™

Genomic DNA was isolated from *Clostridia thermocellum* ATCC 27405™ using the PUREGENE® DNA purification system. The perhydrolase gene was amplified from the genomic DNA by PCR (0.5 min at 94° C., 0.5 min at 55° C., 1 min at 70° C., 30 cycles) using primers identified as SEQ ID NO: 35 and SEQ ID NO: 36. The resulting nucleic acid product (SEQ ID NO: 13) was subcloned into pTrcHis2-TOPO® to generate the plasmid identified as pSW193. The plasmid pSW193 was used to transform *E. coli* MG1655 (ATCC 47076™), *E. coli* UM2 (*E. coli* Genetic Stock Center #7156, Yale University, New Haven Conn.) and *E. coli* KLP18 (see EXAMPLE 15) to generate the strains identified as MG1655/pSW193, UM2/pSW193 and KLP18/pSW193, respectively. MG1655/pSW193, UM2/pSW193 and KLP18/pSW193 were gown in LB media at 37° C. with shaking up to $OD_{600\ nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 11

Cloning and Expression of Perhydrolase from *Bacillus pumilus* PS213

The gene encoding acetyl xylan esterase (axe1) from *B. pumilus* PS213 as reported in GENBANK® (accession #AJ249957) was synthesized using codons optimized for expression in *E. coli* (DNA 2.0, Menlo Park, Calif.). The gene was subsequently amplified by PCR (0.5 min at 94° C., 0.5 min at 55° C., 1 min at 70° C., 30 cycles) using primers identified as SEQ ID NO: 37 and SEQ ID NO: 38. The resulting nucleic acid product (SEQ ID NO: 60) was subcloned into pTrcHis2-TOPO® (Invitrogen, Carlsbad Calif.) to generate the plasmid identified as pSW195. The plasmid pSW195 was used to transform *E. coli* MG1655 (ATCC 47076™), *E. coli* UM2 (*E. coli* Genetic Stock Center #7156, Yale University, New Haven Conn.) and *E. coli* KLP18 (see EXAMPLE 15) to generate the strains identified as MG1655/pSW195, UM2/pSW195 and KLP18/pSW195, respectively. MG1655/pSW195, UM2/pSW195 and KLP18/pSW195 were gown in LB media at 37° C. with shaking up to OD600 nm=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 12

Cloning and Expression of Perhydrolase from *Thermotoga neapolitana*

The gene encoding acetyl xylan esterase from *Thermotoga neapolitana* as reported in GENBANK® (accession #58632) was synthesized using codons optimized for expression in *E. coli* (DNA 2.0, Menlo Park, Calif.). The gene was subsequently amplified by PCR (0.5 min at 94° C., 0.5 min at 55° C., 1 min at 70° C., 30 cycles) using primers identified as SEQ ID NO: 39 and SEQ ID NO: 40. The resulting nucleic acid product (SEQ ID NO: 41) was subcloned into pTrcHis2-TOPO® to generate the plasmid identified as pSW196. The plasmid pSW196 was used to transform *E. coli* MG1655 (ATCC 47076™), *E. coli* UM2 (*E. coli* Genetic Stock Center #7156, Yale University, New Haven Conn.) and *E. coli* KLP18 (see EXAMPLE 15) to generate the strains identified as MG1655/pSW196, UM2/pSW196 and KLP18/pSW196, respectively. MG1655/pSW196, UM2/pSW196 And KLP18/pSW196 were gown in LB media at 37° C. with shaking up to OD600 nm=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

Example 13

Construction of a katG Catalase Disrupted *E. coli* Strain

The kanamycin resistance gene (kan; SEQ ID NO: 42) was amplified from the plasmid pKD13 (SEQ ID NO: 43) by PCR (0.5 min at 94° C., 0.5 min at 55° C., 1 min at 70° C., 30 cycles) using primers identified as SEQ ID NO: 44 and SEQ ID NO: 45 to generate the PCR product identified as SEQ ID NO: 46. The katG nucleic acid sequence is provided as SEQ ID NO: 47 and the corresponding amino acid sequence is SEQ ID NO: 48. *E. coli* MG1655 (ATCC 47076™) was transformed with the temperature-sensitive plasmid pKD46 (SEQ ID NO: 49), which contains the λ-Red recombinase genes (Datsenko and Wanner, 2000, *PNAS USA* 97:6640-6645), and selected on LB-amp plates for 24 h at 30° C. MG1655/pKD46 was transformed with 50-500 ng of the PCR product by electroporation (BioRad Gene Pulser, 0.2 cm cuvette, 2.5 kV, 200 W, 25 uF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system, and checked by PCR to confirm disruption of the katG gene using primers identified as SEQ ID NO: 50 and SEQ ID NO: 51. Several katG-disrupted strains were transformed with the temperature-sensitive plasmid pCP20 (SEQ ID NO: 52), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatG1 and MG1655 KatG2.

Example 14

Construction of a katE Catalase Disrupted *E. coli* Strain

The kanamycin resistance gene (SEQ ID NO: 42) was amplified from the plasmid pKD13 (SEQ ID NO: 43) by PCR (0.5 min at 94° C., 0.5 min at 55° C., 1 min at 70° C., 30 cycles) using primers identified as SEQ ID NO: 53 and SEQ ID NO: 54 to generate the PCR product identified as SEQ ID NO: 55. The katE nucleic acid sequence is provided as SEQ ID NO: 56 and the corresponding amino acid sequence is SEQ ID NO: 57. *E. coli* MG1655 (ATCC 47076™) was transformed with the temperature-sensitive plasmid pKD46 (SEQ ID NO: 49), which contains the λ-Red recombinase genes, and selected on LB-amp plates for 24 h at 30° C. MG1655/pKD46 was transformed with 50-500 ng of the PCR product by electroporation (BioRad Gene Pulser, 0.2 cm cuvette, 2.5 kV, 200 W, 25 uF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE DNA purification system, and checked by PCR to confirm disruption of the katE gene using primers identified as SEQ ID NO: 58 and SEQ ID NO: 59. Several katE-disrupted strains were transformed with the temperature-sensitive plasmid pCP20 (SEQ ID NO: 52), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatE1 and MG1655 KatE2

Example 15

Construction of a katG Catalase and katE Catalase Disrupted *E. coli* Strain (KLP18)

The kanamycin resistance gene (SEQ ID NO: 42) was amplified from the plasmid pKD13 (SEQ ID NO: 43) by PCR (0.5 min at 94° C., 0.5 min at 55° C., 1 min at 70° C., 30 cycles) using primers identified as SEQ ID NO: 53 and SEQ ID NO: 54 to generate the PCR product identified as SEQ ID NO: 55. *E. coli* MG1655 KatG1 (EXAMPLE 13) was transformed with the temperature-sensitive plasmid pKD46 (SEQ ID NO: 49), which contains the λ-Red recombinase genes, and selected on LB-amp plates for 24 h at 30° C. MG1655 KatG1/pKD46 was transformed with 50-500 ng of the PCR product by electroporation (BioRad Gene Pulser, 0.2 cm cuvette, 2.5 kV, 200 W, 25 uF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system, and checked by PCR to confirm disruption of the katE gene using primers identified as SEQ ID NO: 58 and SEQ ID NO: 59. Several katE-disrupted strains (Δ katE) were transformed with the temperature-sensitive plasmid pCP20 (SEQ ID NO: 52), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatG1 KatE18.1 and MG1655 KatG1 KatE23. MG1655 KatG1 KatE18.1 is designated *E. coli* KLP18.

Example 16

Estimation of Perhydrolase Molecular Mass

Cell pellets obtained from shake flask growths of *E. coli* KLP18, a catalase double knockout of *E. coli* MG1655, expressing perhydrolase genes from *Bacillus subtilis*, *Bacillus licheniformis* and *Clostridium thermocellum*, were suspended in 2.2 mL of 0.05 M potassium phosphate buffer (pH 7.0) containing dithiothreitol (1 mM). Each cell suspension was passed twice through a French press having a working pressure of 16,000 psi (~110.3 MPa). The crude extracts were centrifuged at 20,000×g to remove cellular debris, producing clear crude extracts that were assayed for total soluble protein (Bicinchoninic Acid Kit [BCA] for Protein Determination, Sigma Aldrich, BCA1-KT).

Clarified crude extracts (5 μL) containing 20 μg total protein were mixed at room temperature with an equal volume of 2× non-denaturing (native) sample buffer (Invitrogen) and loaded into sample wells of a 1.5 mm×10 well 4-12% Tris-Glycine polyacrylamide mini-gel (Invitrogen), and 7.5 μL of NATIVEMARK™ Unstained Protein Standard (Invitrogen) was loaded into two separate wells. Native gel electrophoresis was performed at 125 V for 105 min using Tris-Glycine running buffer (Invitrogen). Following electrophoresis, the gel was prepared for an in situ esterase activity assay using the pH indicator bromothymol blue.

The gel was washed for 10 min×2 with deionized water and slow mechanical mixing. The gel was then washed for 10 min using 10 mM pH 7.0 phosphate buffer and slow mechanical mixing. Following the removal of the phosphate buffer, 30 mL of 10 mM pH 7.0 phosphate buffer containing 400 μL of saturated bromothymol blue in water was incubated with the gel for 10 min followed by the addition of 1 mL of neat triacetin (Tessenderlo Fine Chemicals; Staffordshire, UK). Within 2 minutes of incubation yellow bands developed at the active perhydrolase enzyme sites. All *B. subtilis* species and *B. licheniformis* had intense bands around a molecular mass of 216 kDa. The *C. thermocellum* displayed an intense major primary band around 432 kDa and a minor secondary band around 576 kDa, indicating esterase activity. All bands were marked by punching a small hole in the gel adjacent to the bands. The gel was washed for 10 min×2 with deionized water and slow mechanical mixing to remove the esterase activity stain. The gel was then washed for 10 min using 10 mM phosphate buffer with slow mechanical mixing to prepare for protein staining. Coomassie blue stain was added to cover the gel. After 5 minutes of slow mechanical mixing, the Coomassie blue was decanted and replaced with 40 mL destain (10% acetic acid, 30% methanol, 60% de-ionized water). After de-staining, the molecular masses of the active areas were estimated. The results are summarized in Table 7.

TABLE 7

Estimation of Perhydrolase Molecular Mass.

| Transformant Strain | Perhydrolase source | Primary native gel activity stain, estimated molecular mass (kDa) | Secondary native gel activity stain, estimated molecular mass (kDa) | Calculated sub-unit molecular mass (kDa) |
|---|---|---|---|---|
| KLP18 | none | none | none | — |
| KLP18/pSW186 | B. subtilis ATCC 31954™ | 216 | none detected | 35.8 |
| KLP18/pSW189 | B. subtilis BE1010 | 216 | none detected | 35.9 |
| KLP18/pSW190 | B. subtilis ATCC 29233™ | 216 | none detected | 35.8 |
| KLP18/pSW191 | B. licheniformis ATCC14580™ | 216 | none detected | 35.8 |
| KLP18/pSW193 | C. thermocellum ATCC 27405™ | 432 | 648 | 36.0 |

Example 17

Fermentation of E. coli UM2/ISW187 Expressing B. subtilis BE1010 Perhydrolase

A fermenter seed culture was prepared by charging a 2-L shake flask with 0.5 L seed medium containing LB Miller medium (DIFCO). The pH of the medium was adjusted to 6.8 and sterilized in the flask. Post-sterilization, 1 mL of ampicillin stock solution (25 mg/mL) was added. The seed medium was inoculated with a 1-mL culture of E. Coli UM2/pSW187 in 20% glycerol, and cultivated at 36° C. and 300 rpm. The seed culture was transferred at ca. 1-2 $OD_{550}$ to a 14 L fermentor (Braun) with 8 L of medium at 35° C. containing $KH_2PO_4$ (3.50 g/L), $FeSO_4$ heptahydrate (0.05 g/L), $MgSO_4$ heptahydrate (2.0 g/L), sodium citrate dihydrate (1.90 g/L), yeast extract (Ambrex 695, 5.0 g/L), Biospumex153K antifoam (0.25 mL/L, Cognis Corporation), NaCl (1.0 g/L), $CaCl_2$ dihydrate (10 g/L), and NIT trace elements solution (10 mL/L). The trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post sterilization addition included 60 g fed batch solution (see below) and 16.0 mL ampicillin stock solution (25 mg/mL). A fed-batch solution contained 2.4 kg of 60% w/w glucose, 0.6 L of 25 g/L yeast extract and 50 g/L Bacto peptone (DIFCO). Glucose feed was initiated when the glucose concentration decreased below 0.5 g/L, starting at 0.3 g/min, and increased progressively each hour to 0.35, 0.40, 0.47, and 0.53 g/min, respectively; the rate remained constant afterwards. Glucose concentration in the medium was monitored and if the concentration exceeded 0.1 g/L the addition rate was decreased or stopped temporarily. Induction was initiated at $OD_{550}$=7 with the addition of 16 mL IPTG (0.5 M). The temperature was controlled at 36° C., the aeration was fixed at 2 slpm (standard liters per minute) with agitation at 400 rpm. The pH was controlled at 6.8; $NH_4OH$ (29% w/w) and $H_2SO_4$ (20% w/v) were used for pH control. The head pressure was 0.5 bar. The cells were harvested by centrifugation at 8 h post IPTG addition.

Example 18

Fermentation of E. coli UM2/ISW186 Expressing B. subtilis ATCC 31954™ Perhydrolase or E. coli UM2/ISW191 Expressing B. licheniformis ATCC 14580™ Perhydrolase The seed culture was prepared as described in Example 17 using E. coli UM2/pSW186 expressing B. subtilis ATCC 31954™ perhydrolase or E. coli UM2/pSW191 expressing B. licheniformis ATCC 14580™ perhydrolase. The fermentation medium was LB Miller (25 g/L, DIFCO). Post sterilization additions included 50 g glucose solution (50% w/w) and 16.0 mL ampicillin stock solution (25 mg/mL). Glucose (50% w/w) was used for fed batch fermentation. Glucose feed was initiated when the glucose concentration decreased below 0.5 g/L, at a constant rate of 0.3 g/min. Glucose concentration in the medium was monitored and if the concentration exceeded 0.1 g/L the addition rate was decreased or stopped temporarily. Induction was initiated at $OD_{550}$=2 with addition of 16 mL IPTG (0.5 M). The temperature was controlled at 36° C., the aeration was fixed at 2 slpm with agitation at 400 rpm. The pH was controlled at 6.8; $NH_4OH$ (29% w/w) and $H_2SO_4$ (20% w/v) were used for pH control. The head pressure was 0.5 bar. The cells were harvested by centrifugation at 8 h post IPTG addition.

Example 19

Fermentation of E. coli KLP18/PSW189 Expressing B. subtilis BE1010 Perhydrolase or E. coli KLP18/PSW191 Expressing B. licheniformis ATCC 14580™ Perhydrolase A fermentor seed culture was prepared by charging a 2-L shake flask with 0.5 L seed medium containing yeast extract (Amberx 695, 5.0 g/L), $K_2HPO_4$ (10.0 g/L), $KH_2PO_4$ (7.0 g/L), sodium citrate dihydrate (1.0 g/L), $(NH_4)_2SO_4$ (4.0 g/L), $MgSO_4$ heptahydrate (1.0 g/L) and ferric ammonium citrate (0.10 g/L). The pH of the medium was adjusted to 6.8 and the medium was sterilized in the flask. Post sterilization additions included glucose (50 wt %, 10.0 mL) and 1 mL ampicillin (25 mg/mL) stock solution. The seed medium was inoculated with a 1-mL culture of E. coli KLP18/PSW189 or KLP18/PSW191 in 20% glycerol, and cultivated at 35° C. and 300 rpm. The seed culture was transferred at ca. 1-2 $OD_{550}$ to a 14 L fermentor (Braun) with 8 L of medium at 35° C. containing $KH_2PO_4$ (3.50 g/L), $FeSO_4$ heptahydrate (0.05 g/L), $MgSO_4$ heptahydrate (2.0 g/L), sodium citrate dihydrate (1.90 g/L), yeast extract (Ambrex 695, 5.0 g/L), Biospumex153K antifoam (0.25 mL/L, Cognis Corporation), NaCl (1.0 g/L), $CaCl_2$ dihydrate (10 g/L), and NIT trace elements solution (10 mL/L). The trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post sterilization additions included glucose solution (50% w/w, 80.0 g) and ampicillin (25 mg/mL) stock solution (16.00 mL). Glucose solution (50% w/w) was used for fed batch. Glucose feed was initiated when glucose concentration decreased to 0.5 g/L, starting at 0.31 g feed/min and increasing progressively each hour to 0.36, 0.42, 0.49, 0.57, 0.66, 0.77, 0.90, 1.04, 1.21, 1.41 1.63 g/min respectively; the rate remained constant afterwards. Glucose concentration in the medium was monitored and if the concentration exceeded 0.1 g/L the feed rate was decreased or stopped temporarily. For E. coli KLP18/

PSW191, the induction was initiated at $OD_{550}$=80 with addition of 16 mL IPTG (0.5 M), for E. coli KLP18/PSW189 the growth was slower and induction was initiated at $OD_{550}$=56. The dissolved oxygen (DO) concentration was controlled at 25% of air saturation. The DO was controlled first by impeller agitation rate (400 to 1400 rpm) and later by aeration rate (2 to 10 slpm). The pH was controlled at 6.8. $NH_4OH$ (29% w/w) and $H_2SO_4$ (20% w/v) were used for pH control. The head pressure was 0.5 bars. The cells were harvested by centrifugation 16 h post IPTG addition.

Example 20

E. coli KLP18 Versus E. coli UM2 as Fermentation Host for Perhydrolase Production E. coli KLP18 (EXAMPLE 15) was used to produce transformants (EXAMPLES 5, 8, 9 and 10) that were grown in multiple 10-L fermentations following the method described in EXAMPLE 19. The final OD for these runs is compared to fermentations that produced E. coli UM2 transformants (EXAMPLES 5, 8, 9 and 10) expressing these same perhydrolases that were run following the fermentation methods described in EXAMPLES 17 and 18. Table 8 summarizes 10-L fermentation runs with both UM2 and KLP18 as host, and demonstrates the superior performance of KLP18 compared to UM2.

TABLE 8

| run ID | Host | plasmid | perhydrolase | run time, (h) | final $OD_{550}$ |
|---|---|---|---|---|---|
| PAA25 | UM2 | pSW186 | SEQ ID NO: 2 | 21.6 | 11.9 |
| PAA26 | UM2 | pSW186 | SEQ ID NO: 2 | 7.4 | 11.9 |
| PAA42 | UM2 | pSW186 | SEQ ID NO: 2 | 12.4 | 5.5 |
| PAA43 | UM2 | pSW186 | SEQ ID NO: 2 | 12.4 | 5.5 |
| PAA48 | KLP18 | pSW186 | SEQ ID NO: 2 | 33.1 | 181.0 |
| PAA30 | UM2 | pSW190 | SEQ ID NO: 32 | 12.1 | 6.2 |
| PAA31 | UM2 | pSW190 | SEQ ID NO: 32 | 12.3 | 8.8 |
| PAA40 | UM2 | pSW190 | SEQ ID NO: 32 | 12.7 | 4.6 |
| PAA41 | UM2 | pSW190 | SEQ ID NO: 32 | 12.6 | 5.3 |
| PAA49 | KLP18 | pSW190 | SEQ ID NO: 32 | 33.6 | 128.0 |
| PAA39 | UM2 | pSW191 | SEQ ID NO: 10 | 10.6 | 6.5 |
| PAA46 | KLP18 | pSW191 | SEQ ID NO: 10 | 33.6 | 140.0 |
| PAA50 | KLP18 | pSW191 | SEQ ID NO: 10 | 36.2 | 155.0 |
| PAA45 | UM2 | pSW193 | SEQ ID NO: 14 | 12.4 | 5.7 |
| PAA51 | KLP18 | pSW193 | SEQ ID NO: 14 | 35.7 | 147.0 |

Example 21

Evaluation of Bacillus subtilis ATCC 31954™ Perhydrolase Expressed in E. coli Transformants The three transformants E. coli TOP10/pSW186, E. coli MG1655/pSW186 and E. coli UM2/pSW186 described in Example 5 were grown in unbaffled shake flasks containing Miller's LB broth (50 mL; Mediatech, Inc, Herndon, Va.) with ampicillin (100 μg/mL) for 14-16 h at 35-37° C. with 200 rpm agitation. Following the overnight growth of the three transformants, each culture was sub-cultured by preparing a 1:100 dilution of each culture into fresh Miller's LB broth containing ampicillin (100 μg/mL). Following a 3 h growth at 35-37° C. with 200 rpm agitation, each culture was induced by the addition of IPTG to a final concentration of 1 mM. After an additional 3 h growth under the same conditions, the cell paste from each culture was harvested by centrifugation at 26,000×g for 20 min at 5° C. Cell extracts of each of the transformants were prepared according to the procedure described in Example 1, except that the extraction buffer used to prepare the 25 wt % wet cell suspension was composed of 0.05 M potassium phosphate (pH 7.0) and 1 mM dithiothreitol.

Separate 1-mL reactions containing triacetin (250 mM), hydrogen peroxide (1.0 M) and 50 μg of extract total protein from one of the three cell extracts (prepared as described above) in 50 mM phosphate buffer (pH 6.5) were run at 25° C. A control reaction was run by substituting 50 mM phosphate buffer (pH 6.5) for the extract total protein solution to determine the concentration of peracetic acid produced by chemical perhydrolysis of triacetin by hydrogen peroxide in the absence of added extract protein. A second set of control reactions was run using 50 μg of extract total protein prepared from extracts of untransformed E. coli TOP10, E. coli MG1655 and E. coli UM2 to determine the background level of peracid produced by each strain in the absence of expressed perhydrolase. The concentration of peracetic acid in the reaction mixtures was determined according to the method of Karst et al. described in Example 2 (Table 9).

TABLE 9

Peracetic acid (PAA) produced by reaction of triacetin (250 mM) and hydrogen peroxide (1.0M) at pH 6.5 in the presence of cell extracts of E. coli TOP10/pSW186, E. coli MG1655/pSW186 and E. coli UM2/pSW186.

| total protein extract source | total protein (μg/mL reaction) | peracetic acid (ppm) in 5 min | peracetic acid (ppm) in 30 min |
|---|---|---|---|
| no extract | 0 | 188 | 598 |
| TOP10 | 50 | 181 | 654 |
| TOP10/pSW186 | 50 | 2684 | 5363 |
| MG1655 | 50 | 173 | 638 |
| MG1655/pSW186 | 50 | 1354 | 4333 |
| UM2 | 50 | 175 | 655 |
| UM2/pSW186 | 50 | 3002 | 6529 |

Example 22

Perhydrolytic Activity of E. coli TOP10/SW186 Extract Expressing Bacillus subtilis ATCC 31954™ Perhydrolase Separate 1.0 mL triacetin perhydrolysis reactions were run as described in Example 21 using the E. coli TOP10/pSW186 transformant extract to provide one of the following total protein concentrations in the reaction: 196 μg/mL, 98 μg/mL, 49 μg/mL, 25 μg/mL, 12.5 μg/mL, 6.25 μg/mL, 3.0 μg/mL, or 1.5 μg/mL total protein concentration in each reaction (Table 10).

TABLE 10

Dependence of peracetic acid (PAA) concentration on total protein concentration derived from E. coli TOP10/pSW186 transformant extract in reactions containing triacetin (250 mM) and hydrogen peroxide (1.0M) at pH 6.5.

| total protein extract source | total protein (μg/mL reaction) | peracetic acid (ppm) in 5 min | peracetic acid (ppm) in 30 min |
|---|---|---|---|
| no extract | 0 | 193 | 854 |
| TOP10 | 50 | 181 | 654 |
| TOP10/pSW186 | 1.5 | 580 | 1710 |
| TOP10/pSW186 | 3.0 | 824 | 2233 |
| TOP10/pSW186 | 6.3 | 1371 | 3029 |
| TOP10/pSW186 | 12.5 | 2052 | 4587 |
| TOP10/pSW186 | 25 | 2849 | 4957 |
| TOP10/pSW186 | 49 | 4294 | |

TABLE 10-continued

Dependence of peracetic acid (PAA) concentration on total protein concentration derived from E. coli TOP10/pSW186 transformant extract in reactions containing triacetin (250 mM) and hydrogen peroxide (1.0M) at pH 6.5.

| total protein extract source | total protein (µg/mL reaction) | peracetic acid (ppm) in 5 min | peracetic acid (ppm) in 30 min |
|---|---|---|---|
| TOP10/pSW186 | 98 | 4244 | |
| TOP10/pSW186 | 196 | 4294 | |

Example 23

Perhydrolytic Activity of E. coli UM2/ISW186 Extract Expressing Bacillus subtilis ATCC 31954™ Perhydrolase An extract of E. Coli UM2/pSW186 transformant (20 mg total protein/mL extract, prepared as described in Example 21) was employed in 1.0 mL perhydrolysis reactions (run as described in Example 21) containing triacetin (40 mM or 100 mM), hydrogen peroxide (40 mM or 100 mM) and extract total protein (0.1 mg/mL or 1.0 mg/mL) in phosphate buffer (Pi, 100 mM, 200 mM or 300 mM) at pH 6.5 or 7.5 at 25° C. each reaction (Table 11).

TABLE 11

Dependence of peracetic acid (PAA) concentration on triacetin and hydrogen peroxide concentrations using perhydrolase derived from E. coli UM2/pSW186 transformant extract at pH 6.5 or 7.5.

| total protein (mg/mL) | $H_2O_2$ (mM) | triacetin (mM) | Pi (mM) | pH | PAA (ppm) in 5 min | PAA (ppm) in 30 min |
|---|---|---|---|---|---|---|
| 0 | 40 | 40 | 100 | 6.5 | 0 | 0 |
| 0 | 40 | 100 | 100 | 6.5 | 0 | 0 |
| 0.1 | 40 | 40 | 100 | 6.5 | 49 | 0 |
| 1 | 40 | 40 | 100 | 6.5 | 239 | 160 |
| 1 | 40 | 100 | 100 | 6.5 | 439 | 560 |
| 0 | 40 | 100 | 200 | 6.5 | 0 | 0 |
| 0 | 100 | 100 | 200 | 6.5 | 1 | 30 |
| 0 | 100 | 100 | 200 | 7.5 | 14 | 1 |
| 0 | 100 | 100 | 300 | 7.5 | 5 | 4 |
| 1 | 100 | 40 | 200 | 6.5 | 75 | 9 |
| 1 | 100 | 100 | 200 | 6.5 | 1150 | 925 |
| 1 | 40 | 100 | 200 | 7.5 | 290 | 80 |
| 1 | 100 | 100 | 300 | 7.5 | 332 | 58 |

Example 24

Evaluation of Perhydrolase Expressed in E. coli Transformants Derived from Bacillus subtilis BE 010

The E. coli TOP10/pSW187, E. coli MG1655/pSW187 and E. coli UM2/pSW187 transformants described in Example 6 were grown in unbaffled shake flasks containing Miller's LB broth (50 mL; Mediatech, Inc, Herndon, Va.) with ampicillin (100 µg/mL) for 14-16 h at 35-37° C. with 200 rpm agitation. Following the overnight growth of the three transformants, each culture was sub-cultured by preparing a 1:100 dilution of each culture into fresh Miller's LB broth containing ampicillin (100 µg/mL). Following a 3 hour growth at 35-37° C. with 200 rpm agitation, each culture was induced by the addition of IPTG to a final concentration of 1 mM. After an additional 3 hours growth under the same conditions, the cell paste from each culture was harvested by centrifugation at 26,000×g for 20 min at 5° C. For cell extract preparation, the procedure described in Example 1 was repeated except that the extraction buffer used to prepare the 25 wt % wet cell suspension was composed of 0.05 M potassium phosphate (pH 7.0) and 1 mM dithiothreitol.

Separate 1.0 mL reactions containing triacetin (250 mM), hydrogen peroxide (1.0 M) and 50 µg of extract total protein in 50 mM phosphate buffer (pH 6.5) were run at 25° C. with each transformant extract. A control reaction was run substituting 50 mM phosphate buffer (pH 6.5) for the extract total protein solution to determine the concentration of peracetic acid produced by chemical perhydrolysis of triacetin with hydrogen peroxide. A second set of control reactions was run using 50 µg of extract total protein prepared from extracts of untransformed E. coli TOP10, E. coli MG1655 and E. coli UM2 to determine the background level of peracid produced by each strain in the absence of expressed perhydrolase. The concentration of peracetic acid in the reaction mixtures (Table 12) was determined according to the method of Karst et al. as described in Example 2.

TABLE 12

Peracetic acid (PAA) produced by reaction of triacetin (250 mM) and hydrogen peroxide (1.0M) at pH 6.5 in the presence of cell extracts of E. coli TOP10/pSW187, E. coli MG1655/pSW187 and E. coli UM2/pSW187.

| total protein extract source | total protein (µg/mL reaction) | peracetic acid (ppm) in 5 min | peracetic acid (ppm) in 30 min |
|---|---|---|---|
| no extract | 0 | 159 | 626 |
| TOP10 | 50 | 181 | 654 |
| TOP10/pSW187 | 50 | 3192 | 6663 |
| MG1655 | 50 | 173 | 638 |
| MG1655/pSW187 | 50 | 3472 | 7349 |
| UM2 | 50 | 175 | 655 |
| UM2/pSW187 | 50 | 3741 | 7626 |

Example 25

Evaluation of Perhydrolases Expressed in E. coli Transformants

The transformants were prepared as described in Examples 5, 6, 7, 8, 9, 10, 18 and 19. Cell extracts of each of the transformants were prepared according to the procedure described in Example 1, except that the extraction buffer used to prepare the 25 wt % wet cell suspension was composed of 0.05 M potassium phosphate (pH 7.0) and 1 mM dithiothreitol.

Separate 1-mL reactions containing triacetin (250 mM), hydrogen peroxide (1.0 M) and 50 µg of extract total protein from a cell extract (prepared as described above) in 50 mM phosphate buffer (pH 6.5) were run at 25° C. A control reaction was run by substituting 50 mM phosphate buffer (pH 6.5) for the extract total protein solution to determine the concentration of peracetic acid produced by chemical perhydrolysis of triacetin by hydrogen peroxide in the absence of added extract protein. A second set of control reactions was run using 50 µg of extract total protein prepared from extracts of untransformed E. coli TOP10, E. coli MG1655, E. coli UM2 and E. coli KLP18 to determine the background level of peracid produced by each strain in the absence of expressed perhydrolase. The concentration of peracetic acid in the reaction mixtures (Table 13) was determined according to the method of Karst et al. described in Example 2.

TABLE 13

Peracetic acid (PAA) produced by reaction of triacetin (250 mM) and hydrogen peroxide (1.0M) at pH 6.5 in the presence of 50 μg of total extract protein/mL from transformant cell extracts of *E. coli* TOP10, *E. coli* MG1655, *E. coli* UM2, *E. coli* PIR2, and *E. coli* KLP18.

| transformant cell extract | perhydrolase source | PAA (ppm) 5 min | PAA (ppm) 5 min, no extract | PAA (ppm) 30 min | PAA (ppm) 30 min, no extract |
|---|---|---|---|---|---|
| TOP10 | none (control) | 181 | 188 | 654 | 598 |
| MG1655 | none (control) | 173 | 188 | 638 | 598 |
| UM2 | none (control) | 175 | 188 | 655 | 598 |
| PIR2 | none (control) | 144 | 276 | 515 | 677 |
| KLP18 | none (control) | 200 | 100 | 555 | 330 |
| TOP10/pSW186 | *B. subtilis* ATCC 31954 ™ | 2684 | 188 | 5363 | 598 |
| MG1655/pSW186 | *B. subtilis* ATCC 31954 ™ | 1354 | 188 | 4333 | 598 |
| UM2/pSW186 | *B. subtilis* ATCC 31954 ™ | 3002 | 188 | 6529 | 598 |
| KLP18/pSW186 | *B. subtilis* ATCC 31954 ™ | 1033 | 268 | 2641 | 792 |
| TOP10/pSW187 | *B. subtilis* BE1010 | 3192 | 159 | 6663 | 626 |
| MG1655/pSW187 | *B. subtilis* BE1010 | 3472 | 159 | 7349 | 626 |
| UM2/pSW187 | *B. subtilis* BE1010 | 3741 | 159 | 7626 | 626 |
| KLP18/pSW189 | *B. subtilis* BE1010 | 2631 | 146 | 6579 | 625 |
| UM2/pSW188 | *B. subtilis* ATCC 6633 ™ | 4617 | 289 | 8742 | 306 |
| UM2/pSW190 | *B. subtilis* ATCC 29233 ™ | 5314 | 320 | 8845 | 738 |
| UM2/pSW190a | *B. subtilis* ATCC 29233 ™ | 2622 | 234 | 3553 | 642 |
| KLP18/pSW190 | *B. subtilis* ATCC 29233 ™ | 1006 | 146 | 3285 | 625 |
| PIR2/pSW191 | *B. licheniformis* ATCC 14580 ™ | 3125 | 276 | 6338 | 677 |
| UM2/pSW191 | *B. licheniformis* ATCC 14580 ™ | 1632 | 276 | 4640 | 677 |
| KLP18/pSW191 | *B. licheniformis* ATCC 14580 ™ | 3936 | 146 | 8016 | 625 |
| MG1655/pSW193 | *C. thermocellum* ATCC 27405 ™ | 2279 | 349 | 3178 | 645 |
| UM2/pSW193 | *C. thermocellum* ATCC 27405 ™ | 2738 | 349 | 3597 | 645 |
| KLP18/pSW193 | *C. thermocellum* ATCC 27405 ™ | 1687 | 146 | 2407 | 625 |
| UM2/pSW195 | *B. pumilus* PS213 | 2226 | 360 | 6354 | 776 |
| KLP18/pSW195 | *B. pumilus* PS213 | 5023 | 100 | 9642 | 394 |
| UM2/pSW196 | *T. neapolitana* | 1347 | 360 | 2553 | 776 |
| KLP18/pSW196 | *T. neapolitana* | 878 | 100 | 2023 | 394 |

Example 26 (Comparative)

Evaluation of Commercial Lipases for Perhydrolysis

Separate 1-mL reactions containing triacetin (250 mM), hydrogen peroxide (1.0 M) and 50 μg of commercial lipases in 50 mM phosphate buffer (pH 6.5) were run at 25° C. Control reactions were run without commercial lipase to determine the concentration of peracetic acid produced by chemical perhydrolysis of triacetin by hydrogen peroxide in the absence of added lipase. The concentration of peracetic acid in the reaction mixtures (Table 14) was determined according to the method of Karst et al. described in Example 2. The commercial lipases were obtained from Sigma/Aldrich Chemical Company (St. Louis, Mo.), BioCatalytics (Pasadena, Calif.), Meito Sangyo Co. (Nagoya, Japan), Amano Enzymes (Lombard, Ill.), Novozymes (Franklinton, N.C.), Valley Research (South Bend, Ind.), and Enzyme Development Corporation (ENZECO®; New York, N.Y.).

TABLE 14

Peracetic acid (PAA) produced by reaction of triacetin (250 mM) and hydrogen peroxide (1.0M) at pH 6.5 in the presence of 50 μg/mL of commercial lipases.

| commercial lipase | lipase source | PAA (ppm); 5 min | PAA (ppm); 30 min |
|---|---|---|---|
| no enzyme | control | 105 | 105 |
| Meito MY | *Candida rugosa* | 155 | 280 |
| Meito OF | *Candida rugosa* | 120 | 340 |
| Meito AL | *Achromobacter* sp. | 165 | 315 |

TABLE 14-continued

Peracetic acid (PAA) produced by reaction of triacetin (250 mM) and hydrogen peroxide (1.0M) at pH 6.5 in the presence of 50 µg/mL of commercial lipases.

| commercial lipase | lipase source | PAA (ppm); 5 min | PAA (ppm); 30 min |
| --- | --- | --- | --- |
| Meito PL | Alcaligenes sp. | 165 | 430 |
| Meito SL | Pseudomonas cepacia | 210 | 440 |
| Meito TL | Pseudomonas stutzeri | 225 | 500 |
| Meito QLC | Alcaligenes sp. | 195 | 240 |
| Meito QLM | Alcaligenes sp. | 225 | 555 |
| no enzyme | control | 150 | 205 |
| Amano F-DS | Rhizopus oryzae | 180 | 265 |
| Amano R | Penicillium roqueforti | 170 | 160 |
| Amano M 10 | Mucor javanicus | 255 | 425 |
| Amano G 50 | Penicillium cambertii | 40 | 40 |
| Amano F-AP15 | Rhizopus oryzae | 120 | 50 |
| Amano AY 30 | Candida rugosa | 140 | 300 |
| Amano PS | Burkholder cepacia | 150 | 150 |
| Amano DS | Aspergillus niger | 140 | 125 |
| Amano AY | Candida rugosa | 180 | 390 |
| Amano AK-20 | Pseudomonas fluorescens | 215 | 500 |
| Amano LPS | Burkholder cepacia | 315 | 350 |
| Amano A 12 | Aspergillus niger | 245 | 490 |
| no enzyme | control | 30 | 55 |
| BioCatalytics ICR 110 | Candida antarctica B | 145 | 245 |
| Novozymes Lipolase 100 L type EX | Thermomyces lanuginosus | 10 | 0 |
| Novozymes Lipozyme TL 100 L | Thermomyces lanuginosus | 125 | 370 |
| Novozymes Lipozyme CALB L | Candida antarctica | 0 | 180 |
| Novozymes Palatase 20000L | Aspergillus oryzae | 95 | 220 |
| Valley Research CR | Candida rugosa | 70 | 320 |
| Valley Research MJ | Mucor javanicus | 140 | 440 |
| Valley Research AN | Aspergillus niger | 165 | 240 |
| Enzeco LC | Candida rugosa | 105 | 120 |
| Enzeco MLC | Aspergillus niger | 140 | 370 |
| Enzeco RO 20 | Rhizopus oryzae | 55 | 100 |

Example 27

Evaluation of Perhydrolases Expressed in E. coli Transformants

Cell extracts of transformants expressing perhydrolase were prepared according to the procedure described in Example 21. Separate 1-mL reactions containing triacetin (105 mM), hydrogen peroxide (78 mM) and 1 mg or 2 mg of extract total protein from a cell extract (prepared as described above) in 50 mM phosphate buffer (pH 6.5) were run at 25° C. A control reaction was run by substituting 50 mM phosphate buffer (pH 6.5) for the extract total protein solution to determine the concentration of peracetic acid produced by chemical perhydrolysis of triacetin by hydrogen peroxide in the absence of added extract protein. The concentration of peracetic acid in the reaction mixtures (Table 15) was determined according to the method of Karst et al. described in Example 2.

TABLE 15

Peracetic acid (PAA) produced by reaction of triacetin (105 mM) and hydrogen peroxide (78 mM) at pH 6.5 or 7.5 in the presence of 1 mg or 2 mg of total extract protein/mL from transformant cell extracts of E. coli MG1655, E. coli UM2, E. coli PIR2 and E. coli KLP18.

| transformant cell extract | source of perhydrolase | total protein (mg/mL) | pH | PAA (ppm); 5 min | PAA (ppm); 30 min |
| --- | --- | --- | --- | --- | --- |
| no extract | control | 0 | 6.5 | 0 | 0 |
| no extract | control | 0 | 7.5 | 8 | 12 |
| UM2/pSW186 | B. subtilis ATCC 31954 ™ | 1.0 | 6.5 | 945 | 1420 |
| UM2/pSW186 | B. subtilis ATCC 31954 ™ | 2.0 | 6.5 | 1000 | 1250 |
| UM2/pSW186 | B. subtilis ATCC 31954 ™ | 1.0 | 7.5 | 1001 | 1215 |
| UM2/pSW186 | B. subtilis ATCC 31954 ™ | 2.0 | 7.5 | 1036 | 1050 |
| no extract | control | 0 | 6.5 | 0 | 0 |
| no extract | control | 0 | 7.5 | 45 | 0 |
| MG1655/pSW187 | B. subtilis BE1010 | 1.0 | 6.5 | 690 | 265 |
| UM2/pSW187 | B. subtilis BE1010 | 1.0 | 6.5 | 730 | 755 |
| UM2/pSW187 | B. subtilis BE1010 | 2.0 | 6.5 | 1400 | 1990 |
| UM2/pSW187 | B. subtilis BE1010 | 2.0 | 7.5 | 1710 | 2105 |
| KLP18/pSW189 | B. subtilis BE1010 | 1.0 | 6.5 | 885 | 1288 |
| KLP18/pSW189 | B. subtilis BE1010 | 2.0 | 6.5 | 950 | 1263 |
| no extract | control | 0 | 6.5 | 0 | 0 |
| UM2/pSW190 | B. subtilis ATCC 29233 ™ | 1.0 | 6.5 | 940 | 685 |
| no extract | control | 0 | 6.5 | 0 | 0 |
| PIR2/pSW191 | B. lichen. ATCC 14580 ™ | 1.0 | 6.5 | 860 | 1305 |
| UM2/pSW191 | B. lichen. ATCC 14580 ™ | 1.0 | 6.5 | 675 | 1530 |
| no extract | control | 0 | 6.5 | 0 | 0 |
| UM2/pSW195 | B. pumilus PS213 | 1.0 | 6.5 | 400 | 850 |
| UM2/pSW195 | B. pumilus PS213 | 2.0 | 6.5 | 460 | 790 |
| no extract | control | 0 | 6.5 | 0 | 0 |
| UM2/pSW196 | T. neapolitana | 1.0 | 6.5 | 1100 | 1685 |
| UM2/pSW196 | T. neapolitana | 2.0 | 6.5 | 1190 | 1900 |

Example 28 (Comparative)

Evaluation of Commercial Lipases for Perhydrolysis

Separate 1-mL reactions containing triacetin (105 mM), hydrogen peroxide (78 mM) and 1 mg of commercial lipases in 50 mM phosphate buffer (pH 6.5) were run at 25° C. A control reaction was run without commercial lipase to determine the concentration of peracetic acid produced by chemical perhydrolysis of triacetin by hydrogen peroxide in the absence of added lipase. The concentration of peracetic acid in the reaction mixtures (Table 16) was determined according to the method of Karst et al. described in Example 2.

TABLE 16

Peracetic acid (PAA) produced by reaction of triacetin (105 mM) and hydrogen peroxide (78 mM) at pH 6.5 in the presence of 1 mg/mL of commercial lipases.

| commercial lipase | lipase source | PAA (ppm); 5 min | PAA (ppm); 30 min |
|---|---|---|---|
| no enzyme | control | 15 | 20 |
| Meito MY | Candida rugosa | 25 | 45 |
| Meito SL | Pseudomonas cepacia | 0 | 0 |
| Meito QLM | Alcaligenes sp. | 35 | 85 |
| Amano F-DS | Rhizopus oryzae | 20 | 50 |
| Amano M 10 | Mucor javanicus | 20 | 40 |
| Amano A 12 | Aspergillus niger | 70 | 140 |
| BioCatalytics ICR 110 | Candida antarctica B | 55 | 110 |

Example 29

B. subtilis ATCC31954™ Perhydrolase Activity with Wetting Agents

A cell extract of E. coli UM2/pSW186 transformant expressing B. subtilis ATCC 31954™ perhydrolase was prepared according to the procedure described in Example 21. Separate 1-mL reactions containing triacetin (105 mM), hydrogen peroxide (78 mM), wetting agent COLATERIC® MSC-NA (mixed short chain sodium dipropionate; Colonial Chemical Co.), SURFYNOL® 2502 (an ethoxylated/propoxylated acetylenic-based surfactant; Air Products and Chemicals; Utrecht, NL), SURFYNOL® MD-20, SILWET® L7650 (a polyalkyleneoxide modified polydimethylsiloxane; Chemtura Corp, Middlebury, Conn.) or SILWET® L8620; a siloxane-based surfactant), and 1 mg of extract total protein in 50 mM phosphate buffer (pH 7.5) were run at 25° C. A control reaction was run by substituting 50 mM phosphate buffer (pH 6.5) for the extract total protein solution to determine the concentration of peracetic acid produced by chemical perhydrolysis of triacetin by hydrogen peroxide in the absence of added extract protein. The concentration of peracetic acid in the reaction mixtures (Table 17) was determined according to the method of Karst et al. described in Example 2.

TABLE 17

Peracetic acid (PAA) produced by reaction of triacetin (105 mM) and hydrogen peroxide (78 mM) at pH 7.5 in the presence of 1 mg of total extract protein/mL from transformant cell extracts of E. coli UM2/pSW186 expressing B. subtilis ATCC 31954 ™ perhydrolase.

| wetting agent | wetting agent conc. (ppm) | total protein (mg/mL) | PAA (ppm); 5 min | PAA (ppm); 30 min |
|---|---|---|---|---|
| None | 0 | 0 | 130 | 170 |
| COLATERIC MSC-NA | 1000 | 0 | 80 | 70 |
| COLATERIC MSC-NA | 1000 | 1.0 | 745 | 1520 |
| SURFYNOL ® 2502 | 1000 | 0 | 35 | 10 |
| SURFYNOL ® 2502 | 1000 | 1.0. | 650 | 1210 |
| SURFYNOL ® MD-20 | 1000 | 0 | 110 | 150 |
| SURFYNOL ® MD-20 | 1000 | 1.0 | 555 | 1110 |
| SILWET ® L7650 | 1000 | 0 | 50 | 0 |
| SILWET ® L7650 | 1000 | 1.0 | 830 | 1360 |
| SILWET ® L8620 | 1000 | 0 | 60 | 135 |
| SILWET ® L8620 | 1000 | 1.0 | 735 | 1145 |

Example 30

B. subtilis BE1010 Perhydrolase Activity with Wetting Agents

A cell extract of E. coli UM2/pSW187 transformant expressing B. subtilis BE1010 perhydrolase was prepared according to the procedure described in Example 21. Separate 1-mL reactions containing triacetin (105 mM), hydrogen peroxide (78 mM), wetting agent (PLURONIC® 17R4 (a polyoxyalkylene ether surfactant; BASF, Mount Olive, N.J.), PLURONIC® L43 (a difunctional block copolymer surfactant), or SILWET® L7650), and 1 mg of extract total protein in 50 mM phosphate buffer (pH 6.5) were run at 25° C. A control reaction was run by substituting 50 mM phosphate buffer (pH 6.5) for the extract total protein solution to determine the concentration of peracetic acid produced by chemical perhydrolysis of triacetin by hydrogen peroxide in the absence of added extract protein. The concentration of peracetic acid in the reaction mixtures (Table 18) was determined according to the method of Karst et al. described in Example 2.

TABLE 18

Peracetic acid (PAA) produced by reaction of triacetin (105 mM) and hydrogen peroxide (78 mM) at pH 6.5 in the presence of 1 mg of total extract protein/mL from transformant cell extracts of E. coli UM2/pSW187 expressing B. subtilis BE1010 perhydrolase.

| wetting agent | wetting agent conc. (ppm) | total protein (mg/mL) | PAA (ppm); 5 min | PAA (ppm); 30 min |
|---|---|---|---|---|
| None | 0 | 0 | 0 | 0 |
| None | 0 | 1.0 | 975 | 1345 |
| PLURONIC ® 17R4 | 2500 | 0 | 0 | 0 |
| PLURONIC ® 17R4 | 2500 | 1.0 | 860 | 1360 |
| PLURONIC ® L43 | 2500 | 0 | 0 | 0 |
| PLURONIC ® L43 | 2500 | 1.0 | 855 | 1360 |
| SILWET ® L7650 | 2500 | 0 | 0 | 0 |
| SILWET ® L7650 | 2500 | 1.0 | 975 | 1205 |

Example 31

Perhydrolase Activity with Wetting and Chelating Agents

A cell extract of E. coli UM2/pSW187 transformant expressing B. subtilis BE1010 perhydrolase was prepared according to the procedure described in Example 21. Separate 1-mL reactions containing triacetin (105 mM), hydrogen peroxide (78 mM), wetting agent (SILWET® L7650), chelating agent (TURPINAL® SL; etidronic acid; Solutia Inc., St. Louis, Mo.), and 1 mg of extract total protein in 50 mM phosphate buffer (pH 6.5) were run at 25° C. A control reaction was run by substituting 50 mM phosphate buffer (pH 6.5) for the extract total protein solution to determine the concentration of peracetic acid produced by chemical perhydrolysis of triacetin by hydrogen peroxide in the absence of added extract protein. The concentration of peracetic acid in the reaction mixtures (Table 19) was determined according to the method of Karst et al. described in Example 2.

TABLE 19

Peracetic acid (PAA) produced by reaction of triacetin (105 mM) and hydrogen peroxide (78 mM) at pH 6.5 in the presence of 1 mg of total extract protein/mL from transformant cell extracts of E. coli UM2/pSW187 expressing B. subtilis BE1010 perhydrolase.

| SILWET ® L7650 (ppm) | Turpinal ® SL (ppm) | total protein (mg/mL) | PAA (ppm); 5 min | PAA (ppm); 30 min |
|---|---|---|---|---|
| 0 | 0 | 0 | 21 | 50 |
| 1000 | 0 | 0 | 20 | 26 |
| 0 | 500 | 0 | 10 | 45 |

TABLE 19-continued

Peracetic acid (PAA) produced by reaction of triacetin (105 mM) and hydrogen peroxide (78 mM) at pH 6.5 in the presence of 1 mg of total extract protein/mL from transformant cell extracts of *E. coli* UM2/pSW187 expressing *B. subtilis* BE1010 perhydrolase.

| SILWET® L7650 (ppm) | Turpinal® SL (ppm) | total protein (mg/mL) | PAA (ppm); 5 min | PAA (ppm); 30 min |
|---|---|---|---|---|
| 1000 | 500 | 0 | 0 | 100 |
| 0 | 0 | 1.0 | 1600 | 2245 |
| 1000 | 0 | 1.0 | 1550 | 2136 |
| 0 | 500 | 1.0 | 1520 | 2130 |
| 1000 | 500 | 1.0 | 1505 | 2080 |

Example 32

Perhydrolase Activity with Wetting Agent, Chelating Agent and Corrosion Inhibitor A cell extract of *E. coli* UM2/pSW187 transformant expressing *B. subtilis* BE1010 perhydrolase was prepared according to the procedure described in Example 21. Separate 1-mL reactions containing triacetin (105 mM), hydrogen peroxide (78 mM), wetting agent (SILWET® L7650), chelating agent (TURPINAL® SL), corrosion inhibitor (benzotriazole) and 1 mg of extract total protein in 50 mM phosphate buffer (pH 6.5) were run at 25° C. A control reaction was run by substituting 50 mM phosphate buffer (pH 6.5) for the extract total protein solution to determine the concentration of peracetic acid produced by chemical perhydrolysis of triacetin by hydrogen peroxide in the absence of added extract protein. The concentration of peracetic acid in the reaction mixtures (Table 20) was determined according to the method of Karst et al. described in Example 2.

TABLE 20

Peracetic acid (PAA) produced by reaction of triacetin (105 mM) and hydrogen peroxide (78 mM) at pH 6.5 in the presence of 1 mg of total extract protein/mL from transformant cell extracts of *E. coli* UM2/pSW187 expressing *B. subtilis* BE1010 perhydrolase.

| SILWET® L7650 (ppm) | Turpinal® SL (ppm) | benzotriazole (ppm) | total protein (mg/mL) | PAA (ppm); 5 min | PAA (ppm); 30 min |
|---|---|---|---|---|---|
| 0 | 0 | 0 | 0 | 0 | 0 |
| 0 | 0 | 0 | 1.0 | 795 | 1205 |
| 1000 | 500 | 1000 | 0 | 0 | 20 |
| 1000 | 500 | 1000 | 1.0 | 825 | 960 |
| 1000 | 500 | 2500 | 0 | 0 | 24 |
| 1000 | 500 | 2500 | 1.0 | 795 | 960 |
| 1000 | 2000 | 2500 | 0 | 0 | 0 |
| 1000 | 2000 | 2500 | 1.0 | 270 | 450 |

Example 33

Peracetic Acid Production Using Immobilized *B. subtilis* ATCC 31954™ or BE1010 Perhydrolase A suspension of 0.50 g of AMBERZYME® Oxirane enzyme immobilization polymeric support (Rohm and Haas, Philadelphia, Pa.) in 5.0 mL of 0.225 M sodium phosphate buffer (pH 8.0) containing 10 mg/mL of total soluble protein from extracts (prepared as described in Example 21) of either *E. coli* KLP/pSW189 (expressing *B. subtilis* BE1010 perhydrolase) or *E. coli* UM2/pSW186 (expressing *B. subtilis* ATCC 31954™ perhydrolase) was mixed on a rotating platform at room temperature for 24 h. The supernatant was then decanted from the immobilized enzyme, which was washed with four 40-mL volumes of phosphate buffer (50 mM, pH 6.5) and stored at 5° C. in this same buffer. The immobilized enzyme was dried by vacuum filtration prior to use.

Separate 1-mL reactions containing triacetin (250 mM), hydrogen peroxide (1.0 M) and either 1.5 mg/mL or 5.0 mg/ml of immobilized perhydrolase (prepared as described above) in 50 mM phosphate buffer (pH 6.5) were run at 25° C. A control reaction was run to determine the concentration of peracetic acid produced by chemical perhydrolysis of triacetin by hydrogen peroxide in the absence of added immobilized enzyme. The concentration of peracetic acid in the reaction mixtures (Table 21) was determined according to the method of Karst et al. described in Example 2.

TABLE 21

Peracetic acid (PAA) produced by reaction of triacetin (250 mM) and hydrogen peroxide (1.0M) at pH 6.5 in the presence of immobilized *B. subtilis* ATCC 31954 ™ or BE1010 perhydrolase.

| immobilized perhydrolase | catalyst loading (mg immob. enzyme/mL) | PAA (ppm); 5 min | PAA (ppm); 30 min |
|---|---|---|---|
| no enzyme | 0 | 83 | 240 |
| *B. subtilis* ATCC 31954 ™ | 1.5 | 185 | 700 |
| *B. subtilis* BE1010 | 1.5 | 502 | 1715 |
| no enzyme | 0 | 99 | 319 |
| *B. subtilis* ATCC 31954 ™ | 5.0 | 596 | 972 |
| *B. subtilis* BE1010 | 5.0 | 1669 | 2610 |

Example 34

Perhydrolysis of a Mixture of Diacetin, Triacetin, and Monoacetin Using Perhydrolases from *B. subtilis*, *B. licheniformis* and *C. thermocellum*

Separate 1-mL reactions containing a mixture of diacetin (118 mM), triacetin (42 mM) and monoacetin (90 mM), hydrogen peroxide (1.0 M) and 50 µg of extract total protein from an *E. coli* UM2 cell extract (prepared as described Example 21) that contained *B. subtilis* or *B. licheniformis* or *C. thermocellum* perhydrolase in 50 mM phosphate buffer (pH 6.5) were run at 25° C. A control reaction was run by substituting 50 mM phosphate buffer (pH 6.5) for the extract total protein solution to determine the concentration of peracetic acid produced by chemical perhydrolysis of a mixture of diacetin (118 mM), triacetin (42 mM) and monoacetin (90 mM) by hydrogen peroxide in the absence of added extract protein. A second control reaction was run using 50 µg of extract total protein prepared from an extract of untransformed *E. coli* UM2 to determine the background level of peracid produced by the *E. coli* strain in the absence of expressed perhydrolase. The concentration of peracetic acid in the reaction mixtures (Table 22) was determined according to the method of Karst et al. described in Example 2.

TABLE 22

Peracetic acid (PAA) produced by reaction of a mixture of diacetin (118 mM), triacetin (42 mM) and monoacetin (90 mM) with hydrogen peroxide (1.0M) at pH 6.5 in the presence of 50 μg of total extract protein/mL from transformant cell extracts of *E. coli* UM2 expressing perhydrolase.

| transformant cell extract | perhydrolase source | PAA (ppm); 5 min | PAA (ppm); 30 min |
|---|---|---|---|
| no extract | control | 76 | 270 |
| UM2 | none (control) | 110 | 276 |
| UM2/pSW186 | *B. subtilis* ATCC 31954 ™ | 2352 | 4341 |
| UM2/pSW187 | *B. subtilis* BE1010 | 2710 | 4713 |
| UM2/pSW188 | *B. subtilis* ATCC 6633 ™ | 2685 | 4234 |
| UM2/pSW190 | *B. subtilis* ATCC 29233 ™ | 641 | 1889 |
| UM2/pSW191 | *B. licheniformis* ATCC 14580 ™ | 1183 | 2608 |
| UM2/pSW193 | *C. thermocellum* ATCC 27405 ™ | 1498 | 1708 |

Example 35

Perhydrolysis of a Mixture of Diacetin, Triacetin, and Monoacetin Using Perhydrolase from *B. subtilis* BE1010

Separate 1-mL reactions containing a mixture of diacetin (49.6 mM), triacetin (17.6 mM) and monoacetin (37.8 mM), hydrogen peroxide (78 mM) and 1 mg or 2 mg of extract total protein from an *E. coli* KLP18/pSW189 cell extract (prepared as described Example 21) in 50 mM phosphate buffer (pH 6.5) were run at 25° C. A control reaction was run by substituting 50 mM phosphate buffer (pH 6.5) for the extract total protein solution to determine the concentration of peracetic acid produced by chemical perhydrolysis of a mixture of diacetin (49.6 mM), triacetin (17.6 mM) and monoacetin (37.8 mM) by hydrogen peroxide in the absence of added extract protein. The concentration of peracetic acid in the reaction mixtures (Table 23) was determined according to the method of Karst et al. described in Example 2.

TABLE 23

Peracetic acid (PAA) produced by reaction of a mixture of diacetin (49.6 mM), triacetin (17.6 mM) and monoacetin (37.8 mM) and hydrogen peroxide (78 mM) at pH 6.5 in the presence of 1 mg or 2 mg of total extract protein/mL from transformant cell extracts of *E. coli* KLP18/pSW189 expressing *B. subtilis* BE1010 perhydrolase.

| transformant cell extract | source of perhydrolase | total protein (mg/mL) | pH | PAA (ppm); 5 min | PAA (ppm); 30 min |
|---|---|---|---|---|---|
| no extract | control | 0 | 6.5 | 0 | 0 |
| KLP18/pSW189 | *B. subtilis* BE1010 | 1.0 | 6.5 | 475 | 423 |
| KLP18/pSW189 | *B. subtilis* BE1010 | 2.0 | 6.5 | 505 | 463 |

Example 36

Perhydrolysis of Acetylated Sugars by *B. subtilis* ATCC 31954™ Perhydrolase A cell extract of *E. coli* UM2/pSW186 transformant expressing *B. subtilis* ATCC 31954™ perhydrolase was prepared according to the procedure described in Example 21. Separate 1-mL reactions containing 0.1 M acetylated sugar (β-D-ribofuranose-1,2,3,5-tetraacetate, tri-O-acetyl-D-galactal, or tri-O-acetyl-D-glucal (Aldrich)), hydrogen peroxide (100 or 500 mM), 2 mg of extract total protein in 50 mM phosphate buffer (pH 6.5) were run at 25° C. A control reaction was run by substituting 50 mM phosphate buffer (pH 6.5) for the extract total protein solution to determine the concentration of peracetic acid produced by chemical perhydrolysis of 0.1 M acetylated sugar (β-D-ribofuranose-1,2,3,5-tetraacetate, tri-O-acetyl-D-galactal, or tri-O-acetyl-D-glucal by hydrogen peroxide in the absence of added extract protein. The concentration of peracetic acid in the reaction mixtures (Table 24) was determined according to the method of Karst et al. described in Example 2.

TABLE 24

Peracetic acid (PAA) produced by reaction of acetylated sugar (100 mM) and hydrogen peroxide (100 or 500 mM) at pH 6.5 in the presence of 2 mg of total extract protein/mL from transformant cell extracts of *E. coli* UM2/pSW186 expressing *B. subtilis* ATCC 31954 ™ perhydrolase.

| acetylated sugar | hydrogen peroxide (mM) | protein (mg/mL) | PAA (ppm); 5 min | PAA (ppm); 30 min |
|---|---|---|---|---|
| β-D-ribofuranose-1,2,3,5-tetraacetate | 500 | 0 | 550 | 705 |
| β-D-ribofuranose-1,2,3,5-tetraacetate | 500 | 2.0 | 1115 | 1540 |
| tri-O-acetyl-D-galactal | 500 | 0 | 220 | 225 |
| tri-O-acetyl-D-galactal | 500 | 2.0 | 885 | 815 |
| tri-O-acetyl-D-glucal | 500 | 0 | 20 | 25 |
| tri-O-acetyl-D-glucal | 500 | 2.0 | 420 | 275 |
| β-D-ribofuranose-1,2,3,5-tetraacetate | 100 | 0 | 52 | 37 |
| β-D-ribofuranose-1,2,3,5-tetraacetate | 100 | 2.0 | 289 | 354 |
| tri-O-acetyl-D-galactal | 100 | 0 | 5 | 95 |
| tri-O-acetyl-D-galactal | 100 | 2.0 | 185 | 175 |
| tri-O-acetyl-D-glucal | 100 | 0 | 65 | 0 |
| tri-O-acetyl-D-glucal | 100 | 2.0 | 102 | 60 |

Example 37

Perhydrolysis of Acetylated Sugars by *B. subtilis* BE1010 Perhydrolase

A cell extract of *E. coli* KLP18/pSW189 transformant expressing *B. subtilis* BE1010 perhydrolase was prepared according to the procedure described in Example 21. Separate 1-mL reactions containing 0.1 M acetylated sugar (β-D-ribofuranose-1,2,3,5-tetraacetate, tri-O-acetyl-D-galactal, or tri-O-acetyl-D-glucal (Aldrich)), hydrogen peroxide (100 or 500 mM), 2 mg of extract total protein in 50 mM phosphate buffer (pH 6.5) were run at 25° C. A control reaction was run by substituting 50 mM phosphate buffer (pH 6.5) for the extract total protein solution to determine the concentration of peracetic acid produced by chemical perhydrolysis of 0.1 M acetylated sugar (β-D-ribofuranose-1,2,3,5-tetraacetate, tri-O-acetyl-D-galactal, or tri-O-acetyl-D-glucal by hydrogen peroxide in the absence of added extract protein. The concentration of peracetic acid in the reaction mixtures (Table 25) was determined according to the method of Karst et al. described in Example 2.

TABLE 25

Peracetic acid (PAA) produced by reaction of acetylated sugar (100 mM) and hydrogen peroxide (100 or 500 mM) at pH 6.5 in the presence of 2 mg of total extract protein/mL from transformant cell extracts of *E. coli* KLP18/pSW189 transformant expressing *B. subtilis* BE1010 perhydrolase.

| acetylated sugar | hydrogen peroxide (mM) | total protein (mg/mL) | PAA (ppm); 5 min | PAA (ppm); 30 min |
|---|---|---|---|---|
| β-D-ribofuranose-1,2,3,5-tetraacetate | 500 | 0 | 550 | 705 |
| β-D-ribofuranose-1,2,3,5-tetraacetate | 500 | 2.0 | 1465 | 1950 |
| tri-O-acetyl-D-galactal | 500 | 0 | 185 | 375 |
| tri-O-acetyl-D-galactal | 500 | 2.0 | 880 | 985 |
| tri-O-acetyl-D-glucal | 500 | 0 | 10 | 40 |
| tri-O-acetyl-D-glucal | 500 | 2.0 | 770 | 405 |
| β-D-ribofuranose-1,2,3,5-tetraacetate | 100 | 0 | 52 | 37 |
| β-D-ribofuranose-1,2,3,5-tetraacetate | 100 | 2.0 | 360 | 437 |
| tri-O-acetyl-D-galactal | 100 | 0 | 102 | 112 |
| tri-O-acetyl-D-galactal | 100 | 2.0 | 305 | 262 |
| tri-O-acetyl-D-glucal | 100 | 0 | 12 | 17 |
| tri-O-acetyl-D-glucal | 100 | 2.0 | 240 | 137 |

Example 38

Cloning and Expression of Perhydrolase from *Bacillus clausii* KSM-K16

The gene encoding a cephalosporin-C hydrolase from *B. clausii* KSM-K16 as reported in GENBANK® (accession #YP_175265; SEQ ID NO: 26) was synthesized using codons optimized for expression in *E. coli* (DNA 2.0, Menlo Park Calif.). The gene (SEQ ID NOs: 65) was subsequently amplified by PCR (0.5 min at 94° C., 0.5 min at 55° C., 1 min at 70° C., 30 cycles) using primers identified as SEQ ID NO: 66 and SEQ ID NO: 67. The resulting nucleic acid product (SEQ ID NO: 64) was cut with restriction enzymes PstI and XbaI and subcloned between the PstI and XbaI sites in pUC1 g to generate the plasmid identified as pSW200. The plasmid pSW200 was used to transform *E. coli* UM2 (*E. coli* Genetic Stock Center #7156, Yale University, New Haven Conn.) to generate the strain identified as UM2/pSW200, UM2/pSW200 was gown in LB media at 37° C. with shaking up to $OD_{600\ nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein. Cell paste was frozen and stored at −80° C.

Example 39

Cloning and Expression of Perhydrolase from *Thermoanaerobacterium saccharolyticum*

The gene encoding acetyl xylan esterase from *Thermoanaerobacterium saccharolyticum* as reported in GENBANK® Accession No. S41858 (SEQ ID NO: 70) was synthesized using codons optimized for expression in *E. coli* (DNA 2.0, Menlo Park Calif.). The gene (SEQ ID NO: 69) was subsequently amplified by PCR (0.5 min at 94° C., 0.5 min at 55° C., 1 min at 70° C., 30 cycles) using primers identified as SEQ ID NO: 71 and SEQ ID NO: 72. The resulting nucleic acid product (SEQ ID NO: 68) was cut with restriction enzymes PstI and XbaI and subcloned between the PstI and XbaI sites in pUC19 to generate the plasmid identified as pSW201. The plasmid pSW201 was used to transform *E. coli* UM2 (*E. coli* Genetic Stock Center #7156, Yale University, New Haven Conn.) to generate the strain identified as UM2/pSW201, UM2/pSW201 was gown in LB media at 37° C. with shaking up to $OD_{600\ nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein. Cell paste was frozen and stored at −80° C.

Example 40

Cloning and Expression of Perhydrolase from *Thermotoga maritima* MSB8

The gene encoding acetyl xylan esterase from *T. maritima* MSB8 as reported in GENBANK® (accession #NP_227893.1; SEQ ID NO: 18) was synthesized using codons optimized for expression in *E. coli* (DNA 2.0, Menlo Park Calif.). The gene (SEQ ID NO: 74) was subsequently amplified by PCR (0.5 min at 94° C., 0.5 min at 55° C., 1 min at 70° C., 30 cycles) using primers identified as SEQ ID NO: 71 and SEQ ID NO: 72. The resulting nucleic acid product (SEQ ID NO: 73) was cut with restriction enzymes PstI and XbaI and subcloned between the PstI and XbaI sites in pUC1 g to generate the plasmid identified as pSW202. The plasmid pSW202 was used to transform *E. coli* UM2 (*E. coli* Genetic Stock Center #7156, Yale University, New Haven Conn.) to generate the strain identified as UM2/pSW202, UM2/pSW202 was gown in LB media at 37° C. with shaking up to $OD_{600\ nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein. Cell paste was frozen and stored at −80° C.

Example 41

Peracetic Acid Production Using Perhydrolases from *B. clausii* KSM-K16, *Thermoanaerobacterium saccharolyticum* and *T. maritima* MSB8

Cell extracts of transformants expressing perhydrolases from *B. clausii* KSM-K16 (*E. coli* UM2/pSW200, Example 38), *Thermoanaerobacterium saccharolyticum* (*E. coli* UM2/pSW201, Example 39), and *T. maritima* MSB8 (*E. coli* UM2/pSW202, Example 40) were each prepared by passing a suspension of cell paste (25 wt % wet cell weight) in 0.05 M potassium phosphate buffer (pH 7.0) containing dithiothreitol (1 mM) twice through a French press having a working pressure of 16,000 psi (~110.32 MPa). The crude extract was then centrifuged at 20,000×g to remove cellular debris, producing a clarified cell extract that was assayed for total soluble protein (Bicinchoninic Acid Kit for Protein Determination, Sigma Aldrich, Sigma catalog #BCA1-KT), then frozen and stored at −80° C.

Reactions (5 mL) containing triacetin, hydrogen peroxide and extract total protein (prepared as described above) in 50 mM phosphate buffer (pH 6.5) were run at 25° C. In a first set of duplicate reactions, the reactants (and corresponding concentrations) were: triacetin (250 mM), hydrogen peroxide (1.0 M) and extract total protein (50 µg/mL). In a second set of duplicate reactions, the reactants (and corresponding concentrations) were: triacetin (100 mM), hydrogen peroxide (250 mM) and extract total protein (1.0 mg/mL). A control reaction was run by substituting 50 mM phosphate buffer (pH 6.5) for the extract total protein solution to determine the concentration of peracetic acid produced by chemical perhydrolysis of triacetin by hydrogen peroxide in the absence of added extract protein. All reactions additionally contained 500 ppm of TURPINAL® SL (etidronic acid; Solutia Inc., St. Louis, Mo.), originally added to the aqueous hydrogen peroxide as stabilizer prior to use.

Determination of the concentration of peracetic acid in the reaction mixtures was performed according to the method described by Karst et al., supra. The peracetic acid concentrations produced in 5 min and 30 min are listed in Table 26.

TABLE 26

Dependence of peracetic acid (PAA) concentration on concentrations of triacetin, hydrogen peroxide and extract total protein prepared from transformants expressing perhydrolases from *B. clausii* KSM-K16 (*E. coli* UM2/pSW200), *Thermoanaerobacterium saccharolyticum* (*E. coli* UM2/pSW201), and *T. maritima* MSB8 (*E. coli* UM2/pSW202) at 25° C. and pH 6.5.

| cell extract (UM2/) | perhydrolase source | total protein (mg/mL) | $H_2O_2$ (mM) | triacetin (mM) | PAA in 5 min (ppm) | PAA in 30 min (ppm) |
|---|---|---|---|---|---|---|
| none | control | 0.00 | 1000 | 250 | 60 | 462 |
| pSW200 | *B. clausii* | 0.05 | 1000 | 250 | 85 | 520 |
| pSW200 | *B. clausii* | 0.05 | 1000 | 250 | 110 | 534 |
| pSW201 | *T. saccharolyticum* | 0.05 | 1000 | 250 | 70 | 615 |
| pSW201 | *T. saccharolyticum* | 0.05 | 1000 | 250 | 95 | 595 |
| pSW202 | *T. maritima* | 0.05 | 1000 | 250 | 1995 | 3270 |
| pSW202 | *T. maritima* | 0.05 | 1000 | 250 | 1978 | 3315 |
| none | control | 0.0 | 250 | 100 | 0 | 0 |
| pSW200 | *B. clausii* | 1.0 | 250 | 100 | 105 | 525 |
| pSW200 | *B. clausii* | 1.0 | 250 | 100 | 120 | 585 |
| pSW201 | *T. saccharolyticum* | 1.0 | 250 | 100 | 290 | 790 |
| pSW201 | *T. saccharolyticum* | 1.0 | 250 | 100 | 195 | 855 |
| pSW202 | *T. maritima* | 1.0 | 250 | 100 | 4770 | 6025 |
| pSW202 | *T. maritima* | 1.0 | 250 | 100 | 4770 | 6005 |

What is claimed is:

1. A process for producing a peroxycarboxylic acid comprising:
   a) providing a set of reaction components, said components comprising:
   1) at least one substrate selected from the group consisting of:
      i) esters having the structure

[X]$_m$R$_5$ wherein X=an ester group of the formula R$_6$C(O)O;

R$_6$=a C1 to C7 linear, branched or cyclic hydrocarbyl moiety, optionally substituted with hydroxyl groups or C1 to C4 alkoxy groups, wherein R$_6$ optionally comprises one or more ether linkages for R$_6$=C2 to C7;

R$_5$=a C1 to C6 linear, branched, or cyclic hydrocarbyl moiety optionally substituted with hydroxyl groups, wherein each carbon atom in R$_5$ individually comprises no more than one hydroxyl group or no more than one ester group;

wherein R$_5$ optionally comprises one or more ether linkages;

m=1 to the number of carbon atoms in R$_5$; and wherein said esters have a solubility in water of at least 5 ppm at 25° C.;

ii) glycerides having the structure

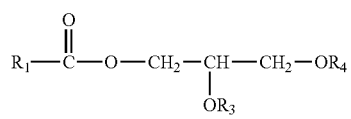

wherein R$_1$=C1 to C7 straight chain or branched chain alkyl optionally substituted with an hydroxyl or a C1 to C4 alkoxy group and R$_3$ and R$_4$ are individually H or R$_1$C(O); and iii) acetylated saccharides selected from the group consisting of acetylated monosaccharides, acetylated disaccharides, and acetylated polysaccharides;

2) a source of peroxygen; and
   3) an enzyme catalyst comprising an enzyme, wherein said enzyme has perhydrolase activity and comprises a polypeptide having at least 95% identity to the amino acid sequence set forth in SEQ ID NO:18; and b) combining said reaction components under suitable reaction conditions whereby a peroxycarboxylic acid is produced.

2. The process of claim 1, further comprising:
   c) contacting a surface or inanimate object with the peroxycarboxylic acid produced in step (b) whereby said surface or said inanimate object is disinfected.

3. The process of claim 1 wherein the substrate is selected from the group consisting of: monoacetin; diacetin; triacetin;

monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; monoesters or diesters of 1,2-ethanediol, 1,2-propanediol, 1,3-propanediol, 1,2-butanediol, 1,3-butanediol, 2,3-butanediol, 1,4-butanediol, 1,2-pentanediol, 2,5-pentanediol, 1,6-pentanediol, 1,2-hexanediol, 2,5-hexanediol, 1,6-hexanediol; and mixtures thereof.

4. The process of claim 1 wherein the enzyme comprises the amino acid sequence set forth in SEQ ID NO:18.

5. The process of claim 1 wherein said enzyme is encoded by a nucleic acid molecule that hybridizes to SEQ ID NO:17 under the following conditions: 0.1×SSC, 0.1% SDS at 65° C. and washed with 2×SSC, 0.1% SDS at 65° C., followed by a second wash with 0.1×SSC, 0.1% SDS at 65° C.

6. The process of claim 5 wherein said nucleic acid molecule has the sequence set forth in SEQ ID NO:17.

\* \* \* \* \*

UNITED STATES PATENT AND TRADEMARK OFFICE
CERTIFICATE OF CORRECTION

| | | |
|---|---|---|
| PATENT NO. | : 8,518,675 B2 | |
| APPLICATION NO. | : 11/943872 | |
| DATED | : August 27, 2013 | |
| INVENTOR(S) | : Dicosimo et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1102 days.

Signed and Sealed this
Twelfth Day of May, 2015

Michelle K. Lee
*Director of the United States Patent and Trademark Office*

SEQUENCE LISTING

<160> NUMBER OF SEQ ID NOS: 74

<210> SEQ ID NO 1
<211> LENGTH: 960
<212> TYPE: DNA
<213> ORGANISM: Bacillus subtilis ATCC 31954
<220> FEATURE:
<221> NAME/KEY: CDS
<222> LOCATION: (1)..(960)

<400> SEQUENCE: 1

```
atg caa cta ttc gat ctg ccg ctc gac caa ttg caa aca tat aag cct       48
Met Gln Leu Phe Asp Leu Pro Leu Asp Gln Leu Gln Thr Tyr Lys Pro
1               5                   10                  15 gaa aaa aca gca ccg aaa gat ttt tct gag ttt tgg aaa ttg tct ttg       96
Glu Lys Thr Ala Pro Lys Asp Phe Ser Glu Phe Trp Lys Leu Ser Leu
                20                  25                  30 gag gaa ctt gca aaa gtc caa gca gaa cct gat tta cag ccg gtt gac      144
Glu Glu Leu Ala Lys Val Gln Ala Glu Pro Asp Leu Gln Pro Val Asp
            35                  40                  45 tat cct gct gac gga gta aaa gtg tac cgt ctc aca tat aaa agc ttc      192
Tyr Pro Ala Asp Gly Val Lys Val Tyr Arg Leu Thr Tyr Lys Ser Phe
        50                  55                  60 gga aac gcc cgc att acc gga tgg tac gcg gtg cct gac aag caa ggc      240
Gly Asn Ala Arg Ile Thr Gly Trp Tyr Ala Val Pro Asp Lys Gln Gly
65                  70                  75                  80 ccg cat ccg gcg atc gtg aaa tat cat ggc tac aat gca agc tat gat      288
Pro His Pro Ala Ile Val Lys Tyr His Gly Tyr Asn Ala Ser Tyr Asp
                85                  90                  95 ggt gag att cat gaa atg gta aac tgg gca ctc cat ggc tac gcc gca      336
```

|     |     |     |     |     |     |     |     |     |     |     |     |     |     |     |
| --- | --- | --- | --- | --- | --- | --- | --- | --- | --- | --- | --- | --- | --- | --- |
| Gly | Glu | Ile | His | Glu | Met | Val | Asn | Trp | Ala | Leu | His | Gly | Tyr | Ala | Ala |
|     |     |     |     | 100 |     |     |     |     | 105 |     |     |     |     | 110 |     |

```
ttc ggc atg ctt gtc cgc ggc cag cag agc agc gag gat acg agt att      384
Phe Gly Met Leu Val Arg Gly Gln Gln Ser Ser Glu Asp Thr Ser Ile
        115                 120                 125 tca ctg cac ggt cac gct ttg ggc tgg atg acg aaa gga att ctt gat      432
Ser Leu His Gly His Ala Leu Gly Trp Met Thr Lys Gly Ile Leu Asp
130                 135                 140 aaa gat aca tac tat tac cgc ggt gtt tat ttg gac gcc gtc cgc gcg      480
Lys Asp Thr Tyr Tyr Tyr Arg Gly Val Tyr Leu Asp Ala Val Arg Ala
145                 150                 155                 160 ctt gag gtc atc agc agc ttc gac gag gtt gac gaa aca agg atc ggt      528
Leu Glu Val Ile Ser Ser Phe Asp Glu Val Asp Glu Thr Arg Ile Gly
                165                 170                 175 gtg aca gga gga agc caa ggc gga ggt tta acc att gcc gca gca gcg      576
Val Thr Gly Gly Ser Gln Gly Gly Gly Leu Thr Ile Ala Ala Ala Ala
            180                 185                 190 ctg tca gac att cca aaa gcc gcg gtt gcc gat tat cct tat tta agc      624
Leu Ser Asp Ile Pro Lys Ala Ala Val Ala Asp Tyr Pro Tyr Leu Ser
        195                 200                 205 aac ttc gaa cgg gcc att gat gtg gcg ctt gaa cag ccg tac ctt gaa      672
Asn Phe Glu Arg Ala Ile Asp Val Ala Leu Glu Gln Pro Tyr Leu Glu
210                 215                 220 atc aat tcc ttc ttc aga aga aat ggc agc ccg gaa aca gaa gtg cag      720
Ile Asn Ser Phe Phe Arg Arg Asn Gly Ser Pro Glu Thr Glu Val Gln
225                 230                 235                 240 gcg atg aag aca ctt tca tat ttc gat att atg aat ctc gct gac cga      768
Ala Met Lys Thr Leu Ser Tyr Phe Asp Ile Met Asn Leu Ala Asp Arg
                245                 250                 255 gtg aag gtg cct gtc ctg atg tca atc ggc ctg att gac aag gtc acg      816
Val Lys Val Pro Val Leu Met Ser Ile Gly Leu Ile Asp Lys Val Thr
            260                 265                 270 ccg ccg tcc acc gtg ttt gcc gcc tac aat cat ttg gaa aca gag aaa      864
Pro Pro Ser Thr Val Phe Ala Ala Tyr Asn His Leu Glu Thr Glu Lys
        275                 280                 285 gag ctg aag gtg tac cgc tac ttc gga cat gag tat atc cct gct ttt      912
Glu Leu Lys Val Tyr Arg Tyr Phe Gly His Glu Tyr Ile Pro Ala Phe
290                 295                 300 caa acg gaa aaa ctt gct ttc ttt aag cag cat ctt aaa ggc tga taa     960
Gln Thr Glu Lys Leu Ala Phe Phe Lys Gln His Leu Lys Gly
305                 310                 315
```

<210> SEQ ID NO 2
<211> LENGTH: 318
<212> TYPE: PRT
<213> ORGANISM: Bacillus subtilis ATCC 31954

<400> SEQUENCE: 2

```
Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
                20                  25                  30

Glu Glu Leu Ala Lys Val Gln Ala Glu Pro Asp Leu Gln Pro Val Asp
            35                  40                  45

Tyr Pro Ala Asp Gly Val Lys Val Tyr Arg Leu Thr Tyr Lys Ser Phe
        50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95
```

```
Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Leu His Gly His Ala Leu Gly Trp Met Thr Lys Gly Ile Leu Asp
130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 3
<211> LENGTH: 24
<212> TYPE: DNA
<213> ORGANISM: artificial sequence
<220> FEATURE:
<223> OTHER INFORMATION: Primer

<400> SEQUENCE: 3
atgcaactat tcgatctgcc gctc                                              24

<210> SEQ ID NO 4
<211> LENGTH: 26
<212> TYPE: DNA
<213> ORGANISM: artificial sequence
<220> FEATURE:
<223> OTHER INFORMATION: Primer

<400> SEQUENCE: 4
ttatcagcct ttaagatgct gcttaa                                            26

<210> SEQ ID NO 5
<211> LENGTH: 957
<212> TYPE: DNA
<213> ORGANISM: Bacillus subtilis subsp. subtilis strain 168

<400> SEQUENCE: 5
atgcaactat tcgatctgcc gctcgaccaa ttgcaaacat ataagcctga aaaacagca       60 ccgaaagatt tttctgagtt ttggaaattg tctttggagg aacttgcaaa agtccaagca     120
gaacctgatt tacagccggt tgactatcct gctgacggag taaaagtgta ccgtctcaca     180
```

```
tataaaagct tcggaaacgc ccgcattacc ggatggtacg cggtgcctga caaggaaggc    240
ccgcatccgg cgatcgtgaa atatcatggc tacaatgcaa gctatgatgg tgagattcat    300
gaaatggtaa actgggcact ccatggctac gccacattcg gcatgcttgt ccgcggccag    360
cagagcagcg aggatacgag tatttcaccg cacggtcacg ctttgggctg atgacgaaa    420 ggaattcttg ataaagatac atactattac cgcggtgttt atttggacgc cgtccgcgcg    480
cttgaggtca tcagcagctt cgacgaggtt gacgaaacaa ggatcggtgt gacaggagga    540
agccaaggcg gaggtttaac cattgccgca gcagcgctgt cagacattcc aaaagccgcg    600
gttgccgatt atccttattt aagcaacttc gaacgggcca ttgatgtggc gcttgaacag    660
ccgtaccttg aaatcaattc cttcttcaga gaaatggca gcccggaaac agaagtgcag    720
gcgatgaaga cactttcata tttcgatatt atgaatctcg ctgaccgagt gaaggtgcct    780
gtcctgatgt caatcggcct gattgacaag gtcacgccgc cgtccaccgt gtttgccgcc    840
tacaatcatt tggaaacaaa gaaagagctg aaggtgtacc gctacttcgg acatgagtat    900
atccctgctt ttcaaactga aaaacttgct ttctttaagc agcatcttaa aggctga       957

<210> SEQ ID NO 6
<211> LENGTH: 318
<212> TYPE: PRT
<213> ORGANISM: Bacillus subtilis subsp. subtilis strain 168

<400> SEQUENCE: 6

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Thr
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240
```

```
Ala Met Lys Thr Leu Ser Tyr Phe Asp Ile Met Asn Leu Ala Asp Arg
            245                 250                 255

Val Lys Val Pro Val Leu Met Ser Ile Gly Leu Ile Asp Lys Val Thr
        260                 265                 270

Pro Pro Ser Thr Val Phe Ala Ala Tyr Asn His Leu Glu Thr Lys Lys
            275                 280                 285

Glu Leu Lys Val Tyr Arg Tyr Phe Gly His Glu Tyr Ile Pro Ala Phe
        290                 295                 300

Gln Thr Glu Lys Leu Ala Phe Phe Lys Gln His Leu Lys Gly
305                 310                 315
```

<210> SEQ ID NO 7
<211> LENGTH: 957
<212> TYPE: DNA
<213> ORGANISM: Bacillus subtilis ATCC 6633

<400> SEQUENCE: 7

```
atgcaactat tcgatctgcc gctcgaccaa ttgcaaacgt ataagcctga aaaacaaca      60
ccgaacgatt tttctgagtt ttggaaatcg tctttggacg aacttgcgaa agtcaaagca    120
gcacctgatt tacagctggt tgattatcct gctgatggag tcaaggtgta ccgcctcaca    180
tataaaagct tcggaaacgc ccgcattacc ggatggtacg cagtgcctga caaggaagga    240
ccgcatccgg cgatcgtcaa atatcatggc tacaacgcta gctatgacgg tgagattcat    300
gaaatggtaa actgggcgct ccacggttac gccgcattcg gcatgctagt ccgcggccag    360
cagagcagcg aggatacgag tatttctcca catggccatg ctttgggctg atgacgaaa    420
ggaatccttg ataaagatac atactattac cggggcgttt atttggacgc tgtccgcgcg    480
cttgaggtca tcagcagctt tgacgaagtt gacgaaacaa gaatcggtgt gacaggcgga    540
agccaaggag gcggcttaac cattgccgca gccgctctgt cagacattcc aaaagccgcg    600
gttgccgatt atccttattt aagcaacttt gaacgggcca ttgatgtggc gcttgaacag    660
ccgtaccttg aaatcaattc cttctttaga agaaatggaa gcccggaaac ggaagagaag    720
gcgatgaaga cactttcata tttcgatatt atgaatctcg ctgaccgagt gaaggtccct    780
gtcctgatgt cgatcggtct gattgacaag gtcacgccgc cgtccaccgt gtttgccgca    840
tacaaccact tggagacaga aaagagctc aaagtgtacc gctacttcgg gcatgagtat    900
atccctgcct ttcaaacaga aaaacttgct ttcctttaagc agcatcttaa aggctga      957
```

<210> SEQ ID NO 8
<211> LENGTH: 318
<212> TYPE: PRT
<213> ORGANISM: Bacillus subtilis ATCC 6633

<400> SEQUENCE: 8

```
Met Gln Leu Phe Asp Leu Pro Leu Asp Gln Leu Gln Thr Tyr Lys Pro
1               5                   10                  15

Glu Lys Thr Thr Pro Asn Asp Phe Ser Glu Phe Trp Lys Ser Ser Leu
            20                  25                  30

Asp Glu Leu Ala Lys Val Lys Ala Ala Pro Asp Leu Gln Leu Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95
```

```
Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Glu Lys
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 9
<211> LENGTH: 957
<212> TYPE: DNA
<213> ORGANISM: Bacillus licheniformis ATCC 14580

<400> SEQUENCE: 9
atgcagcagc ttatgatat gccgcttgaa cagctttatc agtataaacc tgaacggacg      60
gcaccggccg atttaaaga gttctggaag ggttcattgg aggaattggc aaatgaaaaa     120
gcgggaccgc agcttgaacc gcatgaatat ccggctgacg gggtaaaagt ctactggctt     180
acatacagaa gcatcggggg agcgcgaatt aaaggctggt acgcagtacc cgaccgccaa     240
gggcctcatc ctgcgatcgt caaataccac ggctataacg caagctatga cggagacatt     300
cacgatattg tcaattgggc tcttcacggc tatgcggcat cggtatgct ggtccgcgga     360 cagaacagca gtgaagatac agagatctct catcacggac atgtaccggg ctggatgaca     420
aaaggaatcc tcgatccgaa acatattac tacagagggg tctatttaga tgccgtacga     480
gcagtcgaag tggtcagcgg ttttgctgaa gtcgatgaaa agcggatcgg ggtgatcggg     540
gcaagccaag gaggcgggct ggccgtcgcg gtttcggcgc tgtccgatat tccaaaagca     600
gccgtgtcag aataccctta tttaagcaat tttcaacgag cgatcgatac agcgatcgac     660
cagccatatc tcgaaatcaa ctccttttc agaagaaaca ccagtccgga tattgagcag     720
gcggccatgc ataccctgtc ttatttcgat gtcatgaacc ttgcccaatt ggtcaaagcg     780
accgtactca tgtcgatcgg actggttgac catcactc cgccatccac cgtctttgcg     840
gcttacaatc acttggaaac ggataaagaa ataaaagtgt accgttattt tggacacgaa     900
```
tacatcccgc cgttccaaac cgaaaagctg gcgtttctga gaaagcatct gaaataa    957

<210> SEQ ID NO 10
<211> LENGTH: 318
<212> TYPE: PRT
<213> ORGANISM: Bacillus licheniformis ATCC 14580

<400> SEQUENCE: 10

Met Gln Gln Pro Tyr Asp Met Pro Leu Glu Gln Leu Tyr Gln Tyr Lys
1               5                   10                  15

Pro Glu Arg Thr Ala Pro Ala Asp Phe Lys Glu Phe Trp Lys Gly Ser
            20                  25                  30

Leu Glu Glu Leu Ala Asn Glu Lys Ala Gly Pro Gln Leu Glu Pro His
        35                  40                  45

Glu Tyr Pro Ala Asp Gly Val Lys Val Tyr Trp Leu Thr Tyr Arg Ser
    50                  55                  60

Ile Gly Gly Ala Arg Ile Lys Gly Trp Tyr Ala Val Pro Asp Arg Gln
65                  70                  75                  80

Gly Pro His Pro Ala Ile Val Lys Tyr His Gly Tyr Asn Ala Ser Tyr
                85                  90                  95

Asp Gly Asp Ile His Asp Ile Val Asn Trp Ala Leu His Gly Tyr Ala
            100                 105                 110

Ala Phe Gly Met Leu Val Arg Gly Gln Asn Ser Ser Glu Asp Thr Glu
        115                 120                 125

Ile Ser His His Gly His Val Pro Gly Trp Met Thr Lys Gly Ile Leu
    130                 135                 140

Asp Pro Lys Thr Tyr Tyr Tyr Arg Gly Val Tyr Leu Asp Ala Val Arg
145                 150                 155                 160

Ala Val Glu Val Val Ser Gly Phe Ala Glu Val Asp Glu Lys Arg Ile
                165                 170                 175

Gly Val Ile Gly Ala Ser Gln Gly Gly Gly Leu Ala Val Ala Val Ser
            180                 185                 190

Ala Leu Ser Asp Ile Pro Lys Ala Ala Val Ser Glu Tyr Pro Tyr Leu
        195                 200                 205

Ser Asn Phe Gln Arg Ala Ile Asp Thr Ala Ile Asp Gln Pro Tyr Leu
    210                 215                 220

Glu Ile Asn Ser Phe Phe Arg Arg Asn Thr Ser Pro Asp Ile Glu Gln
225                 230                 235                 240

Ala Ala Met His Thr Leu Ser Tyr Phe Asp Val Met Asn Leu Ala Gln
                245                 250                 255

Leu Val Lys Ala Thr Val Leu Met Ser Ile Gly Leu Val Asp Thr Ile
            260                 265                 270

Thr Pro Pro Ser Thr Val Phe Ala Ala Tyr Asn His Leu Glu Thr Asp
        275                 280                 285

Lys Glu Ile Lys Val Tyr Arg Tyr Phe Gly His Glu Tyr Ile Pro Pro
    290                 295                 300

Phe Gln Thr Glu Lys Leu Ala Phe Leu Arg Lys His Leu Lys
305                 310                 315

<210> SEQ ID NO 11
<211> LENGTH: 963
<212> TYPE: DNA
<213> ORGANISM: Bacillus pumilis

<400> SEQUENCE: 11
atgcaattgt tcgatttatc actagaagag ctaaaaaaat ataaaccaaa gaaaacagca    60

```
cgtcctgatt tctcagactt ttggaagaaa tcgctcgaag aactgcgcca agtggaggca    120
gagccaacac ttgaatctta tgactatcca gtgaaaggcg tcaaggtgta ccgcctgacg    180
tatcaaagct ttggacattc taaaattgaa ggcttttatg ctgtgcctga tcaaactggt    240
ccgcatccag cgctcgttcg ttttcatggc tataatgcca gctatgacgg cggcattcac    300
gacatcgtca actgggcgct gcacggctat gcaacatttg gtatgctcgt ccgcggtcaa    360
ggtggcagtg aagacacatc agtgacacca ggcgggcatg cattagggtg gatgacaaaa    420
ggcattttat cgaaagatac gtactattat cgaggcgttt atctagatgc tgttcgtgca    480
cttgaagtca ttcagtcttt ccccgaagta gatgaacacc gtatcggcgt gatcggtgga    540
agtcaggggg gtgcgttagc gattgcggcc gcagccctt cagacattcc aaaagtcgtt    600
gtggcagact atccttactt atcaaatttt gagcgtgcag ttgatgttgc cttggagcag    660
ccttatttag aaatcaattc atactttcgc agaaacagtg atccgaaagt ggaggaaaag    720
gcatttgaga cattaagcta ttttgattta atcaatttag ctggatgggt gaaacagcca    780
acattgatgg cgatcggtct gattgacaaa ataaccccac catctactgt gtttgcggca    840
tacaaccatt tagaaacaga taaagacctg aaagtatatc gctatttggg acacgagttt    900
atccctgctt tcaaacaga gaagctgtcc tttttacaaa agcatttgct tctatcaaca    960
taa                                                                  963
```

<210> SEQ ID NO 12
<211> LENGTH: 320
<212> TYPE: PRT
<213> ORGANISM: Bacillus pumilis

<400> SEQUENCE: 12

```
Met Gln Leu Phe Asp Leu Ser Leu Glu Glu Leu Lys Lys Tyr Lys Pro
1               5                   10                  15

Lys Lys Thr Ala Arg Pro Asp Phe Ser Asp Phe Trp Lys Lys Ser Leu
            20                  25                  30

Glu Glu Leu Arg Gln Val Glu Ala Glu Pro Thr Leu Glu Ser Tyr Asp
        35                  40                  45

Tyr Pro Val Lys Gly Val Lys Val Tyr Arg Leu Thr Tyr Gln Ser Phe
    50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
            100                 105                 110

Phe Gly Met Leu Val Arg Gly Gln Gly Gly Ser Glu Asp Thr Ser Val
        115                 120                 125

Thr Pro Gly Gly His Ala Leu Gly Trp Met Thr Lys Gly Ile Leu Ser
    130                 135                 140

Lys Asp Thr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala Ala
            180                 185                 190

Leu Ser Asp Ile Pro Lys Val Val Val Ala Asp Tyr Pro Tyr Leu Ser
        195                 200                 205
```

```
Asn Phe Glu Arg Ala Val Asp Val Ala Leu Glu Gln Pro Tyr Leu Glu
            210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
                245                 250                 255

Val Lys Gln Pro Thr Leu Met Ala Ile Gly Leu Ile Asp Lys Ile Thr
            260                 265                 270

Pro Pro Ser Thr Val Phe Ala Ala Tyr Asn His Leu Glu Thr Asp Lys
                275                 280                 285

Asp Leu Lys Val Tyr Arg Tyr Phe Gly His Glu Phe Ile Pro Ala Phe
            290                 295                 300

Gln Thr Glu Lys Leu Ser Phe Leu Gln Lys His Leu Leu Leu Ser Thr
305                 310                 315                 320

<210> SEQ ID NO 13
<211> LENGTH: 963
<212> TYPE: DNA
<213> ORGANISM: Clostridium thermocellum ATCC 27405

<400> SEQUENCE: 13
atggcacaat tatatgatat gcctttggag gaattaaaaa aatataagcc tgcgcttaca      60
aaacagaaag attttgatga gttttgggaa aaagccttaa agagctggc tgaaattcct      120 ttaaaatatc aacttatacc ttatgatttt ccggcccgga gggtaaaagt tttcagagtt     180
gaatatcttg ttttaaagg tgcaaatatt gaagggtggc ttgccgttcc cgagggagaa      240
gggttgtatc ccgggcttgt acagtttcac ggatacaact gggcgatgga tggatgtgtt    300
cccgatgtgg taaattgggc tttgaatgga tatgccgcat tcttatgct tgttcgggga     360 cagcagggaa gaagcgtgga caatattgtg cccggcagcg gtcatgcttt gggatggatg   420
tcgaaaggta ttttgtcacc ggaggaatat tattatagag gagtatatat ggatgcggtt    480
cgtgctgttg aaattttggc ttcgcttcct tgtgtggatg aatcgagaat aggagtgaca    540 ggggggcagcc agggtggagg acttgcactg gcggtggctg ctctgtccgg cataccgaaa    600
gttgcagccg tgcattatcc gtttctggca catttgagc gtgccattga cgttgcgccg      660 gacggcccctt atcttgaaat taacgaatat ttaagaagaa acagcggtga agaaatagaa    720
agacaggtaa agaaaaccct ttcctatttt gatatcatga atcttgctcc ccgtataaaa   780
tgccgtactt ggatttgcac tggtcttgtg gatgagatta ctcctccgtc aacggttttt    840
gcagtgtaca atcacctcaa atgcccaaag gaaatttcgg tattcagata ttttgggcat    900
gaacatatgc caggaagcgt tgaaatcaag ctgaggatac ttatggatga gctgaatccg    960
taa                                                                   963

<210> SEQ ID NO 14
<211> LENGTH: 320
<212> TYPE: PRT
<213> ORGANISM: Clostridium thermocellum ATCC 27405

<400> SEQUENCE: 14

Met Ala Gln Leu Tyr Asp Met Pro Leu Glu Glu Leu Lys Lys Tyr Lys
1               5                   10                  15

Pro Ala Leu Thr Lys Gln Lys Asp Phe Asp Glu Phe Trp Glu Lys Ser
            20                  25                  30

Leu Lys Glu Leu Ala Glu Ile Pro Leu Lys Tyr Gln Leu Ile Pro Tyr
        35                  40                  45
```

```
Asp Phe Pro Ala Arg Arg Val Lys Val Phe Arg Val Glu Tyr Leu Gly
 50                  55                  60
Phe Lys Gly Ala Asn Ile Glu Gly Trp Leu Ala Val Pro Glu Gly Glu
 65                  70                  75                  80
Gly Leu Tyr Pro Gly Leu Val Gln Phe His Gly Tyr Asn Trp Ala Met
                 85                  90                  95
Asp Gly Cys Val Pro Asp Val Val Asn Trp Ala Leu Asn Gly Tyr Ala
            100                 105                 110
Ala Phe Leu Met Leu Val Arg Gly Gln Gln Gly Arg Ser Val Asp Asn
        115                 120                 125
Ile Val Pro Gly Ser Gly His Ala Leu Gly Trp Met Ser Lys Gly Ile
    130                 135                 140
Leu Ser Pro Glu Glu Tyr Tyr Tyr Arg Gly Val Tyr Met Asp Ala Val
145                 150                 155                 160
Arg Ala Val Glu Ile Leu Ala Ser Leu Pro Cys Val Asp Glu Ser Arg
                165                 170                 175
Ile Gly Val Thr Gly Ser Gln Gly Gly Leu Ala Leu Ala Val
            180                 185                 190
Ala Ala Leu Ser Gly Ile Pro Lys Val Ala Val His Tyr Pro Phe
        195                 200                 205
Leu Ala His Phe Glu Arg Ala Ile Asp Val Ala Pro Asp Gly Pro Tyr
    210                 215                 220
Leu Glu Ile Asn Glu Tyr Leu Arg Arg Asn Ser Gly Glu Glu Ile Glu
225                 230                 235                 240
Arg Gln Val Lys Lys Thr Leu Ser Tyr Phe Asp Ile Met Asn Leu Ala
                245                 250                 255
Pro Arg Ile Lys Cys Arg Thr Trp Ile Cys Thr Gly Leu Val Asp Glu
            260                 265                 270
Ile Thr Pro Pro Ser Thr Val Phe Ala Val Tyr Asn His Leu Lys Cys
        275                 280                 285
Pro Lys Glu Ile Ser Val Phe Arg Tyr Phe Gly His Glu His Met Pro
    290                 295                 300
Gly Ser Val Glu Ile Lys Leu Arg Ile Leu Met Asp Glu Leu Asn Pro
305                 310                 315                 320
```

<210> SEQ ID NO 15
<211> LENGTH: 978
<212> TYPE: DNA
<213> ORGANISM: Thermotoga neapolitana

<400> SEQUENCE: 15

```
atggccttct tcgatatgcc ccttgaggaa ctgaaaaagt accggcctga aaggtacgag    60
gagaaagatt tcgatgagtt ctggagggaa acacttaaag aaagcgaagg attccctctg   120
gatcccgtct ttgaaaaggt ggactttcat ctcaaaacgg ttgaaacgta cgatgttact   180
ttctctggat acagggggca gagaataaag ggctggcttc ttgttccgaa gttggcggaa   240
gaaaagcttc catgcgtcgt gcagtacata ggttacaatg gtggaagggg ttttccacac   300
gactggctgt tctggccgtc aatgggttac atctgttttg tcatggacac caggggggcag   360
ggaagcggct ggatgaaggg agacacaccg gattaccctg agggtccagt cgatccacag   420
taccccggat tcatgacgag gggcattctg gatccgggaa cctattacta caggcgagtc   480
ttcgtggatg cggtcagggc ggtggaagca gccatttcct tcccgagagt ggattccagg   540
aaggtggtgg tggccggagg cagtcagggt ggggaatcg cccttgcggt gagtgccctg   600
tcgaacaggg tgaaggctct gctctgcgat gtgccgtttc tgtgccactt cagaagggcc   660
```

```
gtgcaacttg tcgacacaca cccatacgtg gagatcacca acttcctcaa aacccacagg    720
gacaaagagg agattgtttt cagaacactt tcctacttcg atggtgtgaa ctttgcagca    780
agggcaaagg tgcccgccct gttttccgtt gggctcatgg acaccatctg tcctccctcg    840
acggtcttcg ccgcttacaa ccactacgcc ggtccaaagg agatcagaat ctatccgtac    900
aacaaccacg aaggtggagg ttcttttcag gcaattgagc aggtgaaatt cttgaagaga    960
ctatttgagg aaggctag                                                  978
```

<210> SEQ ID NO 16
<211> LENGTH: 325
<212> TYPE: PRT
<213> ORGANISM: Thermotoga neapolitana

<400> SEQUENCE: 16

```
Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Val Ala Gly Gly Ser Gln Gly Gly Gly
            180                 185                 190

Ile Ala Leu Ala Val Ser Ala Leu Ser Asn Arg Val Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320
```

Leu Phe Glu Glu Gly
                325

<210> SEQ ID NO 17
<211> LENGTH: 978
<212> TYPE: DNA
<213> ORGANISM: Thermotoga maritima MSB8

<400> SEQUENCE: 17

```
atggccttct tcgatttacc actcgaagaa ctgaagaaat atcgtccaga gcggtacgaa      60
gagaaagact tcgatgagtt ctgggaagag acactcgcag agagcgaaaa gttcccctta     120
gaccccgtct tcgagaggat ggagtctcac ctcaaaacag tcgaagcgta cgatgtcacc     180
ttctccggat acaggggaca gaggatcaaa gggtggctcc ttgttccaaa actggaagaa     240
gaaaaacttc cctgcgttgt gcagtacata ggatacaacg gtggaagagg attccctcac     300
gactggctgt tctggccttc tatgggttac atatgtttcg tcatggatac tcgaggtcag     360
ggaagcggct ggctgaaagg agacacaccg gattaccctg agggtcccgt tgaccctcag     420
tatccaggat tcatgacaag aggaatactg gatcccagaa cttactacta cagacgagtc     480
ttcacggacg ctgtcagagc cgttgaagct gctgcttctt ttcctcaggt agatcaagaa     540
agaatcgtga tagctggagg cagtcagggt ggcggaatag cccttgcggt gagcgctctc     600
tcaaagaaag caaaggctct tctgtgcgat gtgccgtttc tgtgtcactt cagaagagca     660
gtacagcttg tggatacgca tccatacgcg gagatcacga actttctaaa gacccacaga     720
gacaaggaag aaatcgtgtt caggactctt tcctatttcg atggagtgaa cttcgcagcc     780
agagcgaaga tccctgcgct gttttctgtg ggtctcatgg acaacatttg tcctccttca     840
acggttttcg ctgcctacaa ttactacgct ggaccgaagg aaatcagaat ctatccgtac     900
aacaaccacg agggaggagg ctcttttcaa gcggttgaac aggtgaaatt cttgaaaaaa     960
ctatttgaga aaggctaa                                                  978
```

<210> SEQ ID NO 18
<211> LENGTH: 325
<212> TYPE: PRT
<213> ORGANISM: Thermotoga maritima MSB8

<400> SEQUENCE: 18

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

```
Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Cys Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 19
<211> LENGTH: 963
<212> TYPE: DNA
<213> ORGANISM: Thermoanaerobacterium sp.

<400> SEQUENCE: 19
atgggacttt tcgacatgcc attacaaaaa cttagagaat acactggtac aaatccatgc    60
cctgaagatt tcgatgagta ttggaatagg gctttagatg agatgaggtc agttgatcct   120
aaaattgaat tgaaagaaag tagctttcaa gtatcctttg cagaatgcta tgacttgtac   180
tttacaggtg ttcgtggtgc cagaattcat gcaaagtata taaaacctaa gacagaaggg   240
aaacatccag cgttgataag atttcatgga tattcgtcaa attcaggcga ctggaacgac   300
aaattaaatt acgtggcggc aggcttcacc gttgtggcta tggatgtaag aggtcaagga   360
gggcagtctc aagatgttgg cggtgtaact gggaatactt taaatgggca tattataaga   420
gggctagacg atgatgctga taatatgctt tcaggcata ttttcttaga cactgcccaa   480
ttggctggaa tagttatgaa catgccagaa gttgatgaag atagagtggg agtcatggga   540
ccttctcaag gcggagggct gtcgttggcg tgtgctgcat ggagccaag ggtacgcaaa    600 gtagtatctg aatatccttt tttatctgac tacaagagag tttgggactt agaccttgca   660
aaaaacgcct atcaagagat tacggactat ttcaggcttt ttgacccaag gcatgaaagg   720
gagaatgagg tatttacaaa gcttggatat atagacgtta aaaaccttgc gaaaaggata   780
aaaggcgatg tcttaatgtg cgttgggctt atggaccaag tatgtccgcc atcaactgtt   840
tttgcagcct acaacaacat acagtcaaaa aaagatataa agtgtatcc tgattatgga   900 catgaaccta tgagaggatt tggagattta gcgatgcagt ttatgttgga actatattca   960
taa                                                                963
```

```
<210> SEQ ID NO 20
<211> LENGTH: 320
<212> TYPE: PRT
<213> ORGANISM: Thermoanaerobacterium sp.

<400> SEQUENCE: 20

Met Gly Leu Phe Asp Met Pro Leu Gln Lys Leu Arg Glu Tyr Thr Gly
 1               5                  10                  15

Thr Asn Pro Cys Pro Glu Asp Phe Asp Glu Tyr Trp Asn Arg Ala Leu
             20                  25                  30

Asp Glu Met Arg Ser Val Asp Pro Lys Ile Glu Leu Lys Glu Ser Ser
         35                  40                  45

Phe Gln Val Ser Phe Ala Glu Cys Tyr Asp Leu Tyr Phe Thr Gly Val
     50                  55                  60

Arg Gly Ala Arg Ile His Ala Lys Tyr Ile Lys Pro Lys Thr Glu Gly
 65                  70                  75                  80

Lys His Pro Ala Leu Ile Arg Phe His Gly Tyr Ser Ser Asn Ser Gly
                 85                  90                  95

Asp Trp Asn Asp Lys Leu Asn Tyr Val Ala Ala Gly Phe Thr Val Val
            100                 105                 110

Ala Met Asp Val Arg Gly Gln Gly Gln Ser Gln Asp Val Gly Gly
        115                 120                 125

Val Thr Gly Asn Thr Leu Asn Gly His Ile Ile Arg Gly Leu Asp Asp
130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Val Asp Glu Asp Arg Val
                165                 170                 175

Gly Val Met Gly Pro Ser Gln Gly Gly Gly Leu Ser Leu Ala Cys Ala
            180                 185                 190

Ala Leu Glu Pro Arg Val Arg Lys Val Val Ser Glu Tyr Pro Phe Leu
        195                 200                 205

Ser Asp Tyr Lys Arg Val Trp Asp Leu Asp Leu Ala Lys Asn Ala Tyr
    210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270

Gln Val Cys Pro Pro Ser Thr Val Phe Ala Ala Tyr Asn Asn Ile Gln
        275                 280                 285

Ser Lys Lys Asp Ile Lys Val Tyr Pro Asp Tyr Gly His Glu Pro Met
    290                 295                 300

Arg Gly Phe Gly Asp Leu Ala Met Gln Phe Met Leu Glu Leu Tyr Ser
305                 310                 315                 320

<210> SEQ ID NO 21
<211> LENGTH: 1023
<212> TYPE: DNA
<213> ORGANISM: Bacillus sp. NRRL B-14911

<400> SEQUENCE: 21
atgaggacgg ttcctgctcc tgttttttg gagaggagtg gggagatgaa ccttttgat      60 atgccccttg aggagctgca gcattacaag cctgcccaga ccaggcagga tgattttgag    120
tcattctgga aaaagcggat tgaggagaac agtcaatatc cgctgaatat agaagtaatg    180
```

```
gagcgggttt atccggttcc gggagtgaga gtatatgata tttattttga cgggttccgg      240
aattcccgca tccatggggt gtatgttact ccagaaactc cgggagcgga cactcctgcg      300
gcagtgattt tcacggcta taactggaac acgctgcagc cgcattacag cttcaagcac       360
gtgattcagg ggattcctgt actgatggtg gaggtgcggg acaaaatct cttgtctcca       420 gatagaaatc attatgggaa tggaggtccg ggaggctgga tgacactcgg cgtgatggat      480
cccgatcaat attattacag cctggtatat atggactgct ccgcagcat tgatgctgtc       540 agggaactgt cgaggaagag aagtgtgttt gtggaaggcg aagccaggg aggtgcactg       600 gcgattgccg cagccgccct gcaggatgac atcctgcttg cactcgccga catccctttt      660
ctcacccatt tcaagcgttc cgtggagctt tcctcggatg gaccgtatca ggagatttcc      720
cactacttca agttcatga tcctcttcat caaacgaaag agcaggtata tcagacgctc       780
agctatgtgg actgcatgaa catggccagc atggttgaat gtccagtcct tctttcagcc     840
ggtctggaag acatcgtttg tccccgtcc agtgcatttg cactgttcaa ccatctcggc      900
gggccaaaag aaatacgggc ctatccggaa tacgcccatg aagtaccggc tgtccatgaa     960
gaggaaaagc tgaagtttat atcttcaagg ctaaaaaata gagaaaagag gtgccggcca    1020
tga                                                                 1023
```

<210> SEQ ID NO 22
<211> LENGTH: 340
<212> TYPE: PRT
<213> ORGANISM: Bacillus sp. NRRL B-14911

<400> SEQUENCE: 22

```
Met Arg Thr Val Pro Ala Pro Val Phe Leu Glu Arg Ser Gly Glu Met
1               5                   10                  15

Asn Leu Phe Asp Met Pro Leu Glu Glu Leu Gln His Tyr Lys Pro Ala
            20                  25                  30

Gln Thr Arg Gln Asp Asp Phe Glu Ser Phe Trp Lys Lys Arg Ile Glu
        35                  40                  45

Glu Asn Ser Gln Tyr Pro Leu Asn Ile Glu Val Met Glu Arg Val Tyr
    50                  55                  60

Pro Val Pro Gly Val Arg Val Tyr Asp Ile Tyr Phe Asp Gly Phe Arg
65                  70                  75                  80

Asn Ser Arg Ile His Gly Val Tyr Val Thr Pro Glu Thr Pro Gly Ala
                85                  90                  95

Asp Thr Pro Ala Ala Val Ile Phe His Gly Tyr Asn Trp Asn Thr Leu
            100                 105                 110

Gln Pro His Tyr Ser Phe Lys His Val Ile Gln Gly Ile Pro Val Leu
        115                 120                 125

Met Val Glu Val Arg Gly Gln Asn Leu Leu Ser Pro Asp Arg Asn His
130                 135                 140

Tyr Gly Asn Gly Gly Pro Gly Gly Trp Met Thr Leu Gly Val Met Asp
145                 150                 155                 160

Pro Asp Gln Tyr Tyr Tyr Ser Leu Val Tyr Met Asp Cys Phe Arg Ser
                165                 170                 175

Ile Asp Ala Val Arg Glu Leu Ser Arg Lys Arg Ser Val Phe Val Glu
            180                 185                 190

Gly Gly Ser Gln Gly Gly Ala Leu Ala Ile Ala Ala Ala Leu Gln
        195                 200                 205

Asp Asp Ile Leu Leu Ala Leu Ala Asp Ile Pro Phe Leu Thr His Phe
210                 215                 220
```

Lys Arg Ser Val Glu Leu Ser Ser Asp Gly Pro Tyr Gln Glu Ile Ser
225                 230                 235                 240

His Tyr Phe Lys Val His Asp Pro Leu His Gln Thr Glu Glu Gln Val
            245                 250                 255

Tyr Gln Thr Leu Ser Tyr Val Asp Cys Met Asn Met Ala Ser Met Val
        260                 265                 270

Glu Cys Pro Val Leu Leu Ser Ala Gly Leu Glu Asp Ile Val Cys Pro
    275                 280                 285

Pro Ser Ser Ala Phe Ala Leu Phe Asn His Leu Gly Gly Pro Lys Glu
    290                 295                 300

Ile Arg Ala Tyr Pro Glu Tyr Ala His Glu Val Pro Ala Val His Glu
305                 310                 315                 320

Glu Glu Lys Leu Lys Phe Ile Ser Ser Arg Leu Lys Asn Arg Glu Lys
                325                 330                 335

Arg Cys Arg Pro
            340

<210> SEQ ID NO 23
<211> LENGTH: 960
<212> TYPE: DNA
<213> ORGANISM: Bacillus halodurans C-125

<400> SEQUENCE: 23
ttagagatca gataaaaatt gaaaatccg atcacgatgg cctggcaaat cttcgtgagc      60
aaagtctgga tataactcga tactttttgt cgtcgtgagt ttgttataca tggcaaattg    120
tgtagacggc gggcaaaccg tatccattaa cccaacagca agtaagactt ctcccttttac   180
gagtggagca agatgctgaa tatcaatata gcctagcttc gtaaagattt cagcctcacg    240
tcggtgctgt ggatcaaagc gacgaaaata cgtttgcaat tcgtcataag ctttctcggc    300
taaatccatc tcccatacgc gttggtaatc gctaaggaaa ggataaacag agctaccctt   360
tttaattttc ggttccaaag ccgcacaagc aatcgctaag gccctcctt gtgaccaacc    420
tgtcactgcc acgcgctctt catcgacttc aggaaggttc atcacaatgt ggcaagctg    480
agccgtatca agaaacacat gacggaacaa taattgatca gcattatcat cgagtccgcg   540
tattatatga ccggaatgag tattccctt cacgcctcct gtgtcttcag acaagcctcc    600
ttgcccgcga acgtccattg caagaacaga atatccgagg gctgcgtaat gaagtaaacc   660
cgtccattcc cccgcattca tcgtatatcc gtgaaaatga ataaccgccg ggtgtgtccc   720
gctcgtgtgt cttgggcgca cgtattttgc gtgaattcta gcacccctaa cccctgtaaa   780
atataggtgg aagcattctg catacgtggt ttgaaaatca ctcggtatga gctctacgtt    840
tggatttacc tttctcatct cttgtaaagc acgatcccaa tactcagtaa agtcatctgg   900
ctttggatta cgtcccatgt actctttaa ttcggttaac ggcatgtcta ttagtggcat   960

<210> SEQ ID NO 24
<211> LENGTH: 319
<212> TYPE: PRT
<213> ORGANISM: Bacillus halodurans C-125

<400> SEQUENCE: 24

Met Pro Leu Ile Asp Met Pro Leu Thr Glu Leu Lys Glu Tyr Met Gly
1               5                   10                  15

Arg Asn Pro Lys Pro Asp Asp Phe Thr Glu Tyr Trp Asp Arg Ala Leu
            20                  25                  30

Gln Glu Met Arg Lys Val Asn Pro Asn Val Glu Leu Ile Pro Ser Asp

```
                35                  40                  45
Phe Gln Thr Thr Tyr Ala Glu Cys Phe His Leu Tyr Phe Thr Gly Val
 50                  55                  60

Arg Gly Ala Arg Ile His Ala Lys Tyr Val Arg Pro Arg His Thr Ser
 65                  70                  75                  80

Gly Thr His Pro Ala Val Ile His Phe His Gly Tyr Thr Met Asn Ala
                     85                  90                  95

Gly Glu Trp Thr Gly Leu Leu His Tyr Ala Ala Leu Gly Tyr Ser Val
                100                 105                 110

Leu Ala Met Asp Val Arg Gly Gln Gly Gly Leu Ser Glu Asp Thr Gly
                115                 120                 125

Gly Val Lys Gly Asn Thr His Ser Gly His Ile Ile Arg Gly Leu Asp
130                 135                 140

Asp Asn Ala Asp Gln Leu Leu Phe Arg His Val Phe Leu Asp Thr Ala
145                 150                 155                 160

Gln Leu Ala Asn Ile Val Met Asn Leu Pro Glu Val Asp Glu Glu Arg
                165                 170                 175

Val Ala Val Thr Gly Trp Ser Gln Gly Gly Ala Leu Ala Ile Ala Cys
                180                 185                 190

Ala Ala Leu Glu Pro Lys Ile Lys Lys Val Ala Pro Val Tyr Pro Phe
                195                 200                 205

Leu Ser Asp Tyr Gln Arg Val Trp Glu Met Asp Leu Ala Glu Lys Ala
                210                 215                 220

Tyr Asp Glu Leu Gln Thr Tyr Phe Arg Arg Phe Asp Pro Gln His Arg
225                 230                 235                 240

Arg Glu Ala Glu Ile Phe Thr Lys Leu Gly Tyr Ile Asp Ile Gln His
                245                 250                 255

Leu Ala Pro Leu Val Lys Gly Glu Val Leu Leu Ala Val Gly Leu Met
                260                 265                 270

Asp Thr Val Cys Pro Pro Ser Thr Gln Phe Ala Met Tyr Asn Lys Leu
                275                 280                 285

Thr Thr Thr Lys Ser Ile Glu Leu Tyr Pro Asp Phe Ala His Glu Asp
                290                 295                 300

Leu Pro Gly His Arg Asp Arg Ile Phe Gln Phe Leu Ser Asp Leu
305                 310                 315

<210> SEQ ID NO 25
<211> LENGTH: 954
<212> TYPE: DNA
<213> ORGANISM: Bacillus clausii KSM-K16

<400> SEQUENCE: 25
atgccattag tcgatatgcc gttgcgcgag ttgttagctt atgaaggaat aaaccctaaa      60
ccagcagatt ttgaccaata ctggaaccgg gccaaaacgg aaattgaagc gattgatccc     120
gaagtcactc tagtcgaatc ttctttccag tgttcgtttg caaactgtta ccatttctat     180
tatcgaagcg ctggaaatgc aaaaatccat gcgaaatacg tacagccaaa agcaggggag     240
aagacgccag cagtttttat gttccatggg tatgggggc gttcagccga atggagcagc     300
ttgttaaatt atgtagcggc gggttttttct gttttctata tggacgtgcg tggacaaggt     360
ggaacttcag aggatcctgg gggcgtaagg gggaatacat ataggggcca cattattcgc     420
ggcctcgatg ccgggccaga cgcactttttt taccgcagcg ttttcttgga caccgtccaa     480
ttggttcgtg ctgctaaaac attgcctcac atcgataaaa cacggcttat ggccacaggg     540
tggtcgcaag ggggcgcctt aacgcttgcc tgtgctgccc ttgttcctga aatcaagcgt     600
```

-continued

```
cttgctccag tatcccgtt tttaagcgat tacaagcgag tgtggcaaat ggatttagcg        660
gttcgttcgt ataaagaatt ggctgattat ttccgttcat acgatccgca acataaacgc        720
catggcgaaa tttttgaacg ccttggctac atcgatgtcc agcatcttgc tgaccggatt        780
caaggagatg tcctaatggg agttggttta atggatacag aatgcccgcc gtctacccaa        840
tttgctgctt ataataaaat aaaggctaaa aaatcgtatg agctctatcc tgattttggc        900
catgagcacc ttccaggaat gaacgatcat attttttcgct ttttcactag ttga            954
```

<210> SEQ ID NO 26
<211> LENGTH: 317
<212> TYPE: PRT
<213> ORGANISM: Bacillus clausii KSM-K16

<400> SEQUENCE: 26

```
Met Pro Leu Val Asp Met Pro Leu Arg Glu Leu Leu Ala Tyr Glu Gly
1               5                   10                  15

Ile Asn Pro Lys Pro Ala Asp Phe Asp Gln Tyr Trp Asn Arg Ala Lys
            20                  25                  30

Thr Glu Ile Glu Ala Ile Asp Pro Glu Val Thr Leu Val Glu Ser Ser
        35                  40                  45

Phe Gln Cys Ser Phe Ala Asn Cys Tyr His Phe Tyr Tyr Arg Ser Ala
    50                  55                  60

Gly Asn Ala Lys Ile His Ala Lys Tyr Val Gln Pro Lys Ala Gly Glu
65                  70                  75                  80

Lys Thr Pro Ala Val Phe Met Phe His Gly Tyr Gly Gly Arg Ser Ala
                85                  90                  95

Glu Trp Ser Ser Leu Leu Asn Tyr Val Ala Ala Gly Phe Ser Val Phe
            100                 105                 110

Tyr Met Asp Val Arg Gly Gln Gly Gly Thr Ser Glu Asp Pro Gly Gly
        115                 120                 125

Val Arg Gly Asn Thr Tyr Arg Gly His Ile Ile Arg Gly Leu Asp Ala
    130                 135                 140

Gly Pro Asp Ala Leu Phe Tyr Arg Ser Val Phe Leu Asp Thr Val Gln
145                 150                 155                 160

Leu Val Arg Ala Ala Lys Thr Leu Pro His Ile Asp Lys Thr Arg Leu
                165                 170                 175

Met Ala Thr Gly Trp Ser Gln Gly Gly Ala Leu Thr Leu Ala Cys Ala
            180                 185                 190

Ala Leu Val Pro Glu Ile Lys Arg Leu Ala Pro Val Tyr Pro Phe Leu
        195                 200                 205

Ser Asp Tyr Lys Arg Val Trp Gln Met Asp Leu Ala Val Arg Ser Tyr
    210                 215                 220

Lys Glu Leu Ala Asp Tyr Phe Arg Ser Tyr Asp Pro Gln His Lys Arg
225                 230                 235                 240

His Gly Glu Ile Phe Glu Arg Leu Gly Tyr Ile Asp Val Gln His Leu
                245                 250                 255

Ala Asp Arg Ile Gln Gly Asp Val Leu Met Gly Val Gly Leu Met Asp
            260                 265                 270

Thr Glu Cys Pro Pro Ser Thr Gln Phe Ala Ala Tyr Asn Lys Ile Lys
        275                 280                 285

Ala Lys Lys Ser Tyr Glu Leu Tyr Pro Asp Phe Gly His Glu His Leu
    290                 295                 300

Pro Gly Met Asn Asp His Ile Phe Arg Phe Phe Thr Ser
305                 310                 315
```

<210> SEQ ID NO 27
<211> LENGTH: 49
<212> TYPE: DNA
<213> ORGANISM: artificial sequence
<220> FEATURE:
<223> OTHER INFORMATION: Primer

<400> SEQUENCE: 27
taactgcagt aaggaggaat aggacatgca actattcgat ctgccgctc            49

<210> SEQ ID NO 28
<211> LENGTH: 35
<212> TYPE: DNA
<213> ORGANISM: artificial sequence
<220> FEATURE:
<223> OTHER INFORMATION: Primer

<400> SEQUENCE: 28
tgatctagat tatcagcctt taagatgctg cttaa                           35

<210> SEQ ID NO 29
<211> LENGTH: 994
<212> TYPE: DNA
<213> ORGANISM: artificial sequence
<220> FEATURE:
<223> OTHER INFORMATION: Synthetic construct

<400> SEQUENCE: 29
taactgcagt aaggaggaat aggacatgca actattcgat ctgccgctcg accaattgca    60
aacatataag cctgaaaaaa cagcaccgaa agatttttct gagttttgga aattgtcttt   120
ggaggaactt gcaaaagtcc aagcagaacc tgatttacag ccggttgact atcctgctga   180
cggagtaaaa gtgtaccgtc tcacatataa aagcttcgga aacgcccgca ttaccggatg   240
gtacgcggtg cctgacaagc aaggcccgca tccggcgatc gtgaaatatc atggctacaa   300
tgcaagctat gatggtgaga ttcatgaaat ggtaaactgg gcactccatg gctacgccgc   360
attcggcatg cttgtccgcg gccagcgaga cagcgaggat acgagtattt cactgcacgg   420
tcacgctttg ggctggatga cgaaaggaat tcttgataaa gatacatact attaccgcgg   480
tgtttatttg gacgccgtcc gcgcgcttga ggtcatcagc agcttcgacg aggttgacga   540
aacaaggatc ggtgtgacag gaggaagcca aggcggaggt ttaaccattg ccgcagcagc   600
gctgtcagac attccaaaag ccgcggttgc cgattatcct tatttaagca acttcgaacg   660
ggccattgat gtggcgcttg aacagccgta ccttgaaatc aattccttct tcagaagaaa   720
tggcagcccg gaaacagaag tgcaggcgat gaagacactt tcatatttcg atattatgaa   780
tctcgctgac cgagtgaagg tgcctgtcct gatgtcaatc ggcctgattg acaaggtcac   840
gccgccgtcc accgtgtttg ccgcctacaa tcatttggaa acagagaaag agctgaaggt   900
gtaccgctac ttcggacatg agtatatccc tgctttcaa acggaaaaac ttgctttctt   960
taagcagcat cttaaaggct gataatctag atca                             994

<210> SEQ ID NO 30
<211> LENGTH: 994
<212> TYPE: DNA
<213> ORGANISM: artificial sequence
<220> FEATURE:
<223> OTHER INFORMATION: Synthetic construct

<400> SEQUENCE: 30
taactgcagt aaggaggaat aggacatgca actattcgat ctgccgctcg accaattgca    60

```
aacatatatag cctgaaaaaa cagcaccgaa agatttttct gagttttgga aattgtcttt      120
ggaggaactt gcaaaagtcc aagcagaacc tgatttacag ccggttgact atcctgctga      180
cggagtaaaa gtgtaccgtc tcacatataa aagcttcgga aacgcccgca ttaccggatg      240
gtacgcggtg cctgacaagg aaggcccgca tccggcgatc gtgaaatatc atggctacaa      300
tgcaagctat gatggtgaga ttcatgaaat ggtaaactgg gcactccatg gctacgccac      360
attcggcatg cttgtccgcg gccagcagag cagcgaggat acgagtattt caccgcacgg      420
tcacgctttg ggctggatga cgaaaggaat tcttgataaa gatacatact attaccgcgg      480
tgtttatttg gacgccgtcc gcgcgcttga ggtcatcagc agcttcgacg aggttgacga      540
aacaaggatc ggtgtgacag gaggaagcca aggcggaggt ttaaccattg ccgcagcagc      600
gctgtcagac attccaaaag ccgcggttgc cgattatcct tatttaagca acttcgaacg      660
ggccattgat gtggcgcttg aacagccgta ccttgaaatc aattccttct tcagaagaaa      720
tggcagcccg gaaacagaag tgcaggcgat gaagacactt tcatatttcg atattatgaa      780
tctcgctgac cgagtgaagg tgcctgtcct gatgtcaatc ggcctgattg acaaggtcac      840
gccgccgtcc accgtgtttg ccgcctacaa tcatttggaa acaaagaaag agctgaaggt      900
gtaccgctac ttcggacatg agtatatccc tgcttttcaa actgaaaaac ttgctttctt      960
taagcagcat cttaaaggct gataatctag atca                                  994
```

`<210>` SEQ ID NO 31
`<211>` LENGTH: 960
`<212>` TYPE: DNA
`<213>` ORGANISM: Bacillus subtilis ATCC 29233
`<220>` FEATURE:
`<221>` NAME/KEY: CDS
`<222>` LOCATION: (1)..(960)

`<400>` SEQUENCE: 31

```
atg caa cta ttc gat ctg ccg ctc gac caa ttg caa aca tat aag cct        48
Met Gln Leu Phe Asp Leu Pro Leu Asp Gln Leu Gln Thr Tyr Lys Pro
1               5                   10                  15 gaa aaa aca gca ccg aaa gat ttt tct gag ttt tgg aaa ttg tct ttg        96
Glu Lys Thr Ala Pro Lys Asp Phe Ser Glu Phe Trp Lys Leu Ser Leu
                20                  25                  30 gag gaa ctt gca aaa gtc caa gca gaa cct gat cta cag ccg gtt gac       144
Glu Glu Leu Ala Lys Val Gln Ala Glu Pro Asp Leu Gln Pro Val Asp
            35                  40                  45 tat cct gct gac gga gta aaa gtg tac cgt ctc aca tat aaa agc ttc       192
Tyr Pro Ala Asp Gly Val Lys Val Tyr Arg Leu Thr Tyr Lys Ser Phe
        50                  55                  60 gga aac gcc cgc att acc gga tgg tac gcg gtg cct gac aag caa ggc       240
Gly Asn Ala Arg Ile Thr Gly Trp Tyr Ala Val Pro Asp Lys Gln Gly
65                  70                  75                  80 ccg cat ccg gcg atc gtg aaa tat cat ggc tac aat gca agc tat gat       288
Pro His Pro Ala Ile Val Lys Tyr His Gly Tyr Asn Ala Ser Tyr Asp
                85                  90                  95 ggt gag att cat gaa atg gta aac tgg gca ctc cat ggc tac gcc gca       336
Gly Glu Ile His Glu Met Val Asn Trp Ala Leu His Gly Tyr Ala Ala
            100                 105                 110 ttc ggc atg ctt gtc cgc ggc cag cag agc agc gag gat acg agt att       384
Phe Gly Met Leu Val Arg Gly Gln Gln Ser Ser Glu Asp Thr Ser Ile
        115                 120                 125 tca ccg cac ggt cac gct ttg ggc tgg atg acg aaa gga att ctt gat       432
Ser Pro His Gly His Ala Leu Gly Trp Met Thr Lys Gly Ile Leu Asp
    130                 135                 140
```

```
aaa gat aca tac tat tac cgc ggt gtt tat ttg gac gcc gtc cgc gcg      480
Lys Asp Thr Tyr Tyr Tyr Arg Gly Val Tyr Leu Asp Ala Val Arg Ala
145                 150                 155                 160 ctt gag gtc atc agc agc ttc gac gag gtt gac gaa aca agg atc ggt      528
Leu Glu Val Ile Ser Ser Phe Asp Glu Val Asp Glu Thr Arg Ile Gly
                165                 170                 175 gtg aca gga gga agc caa ggc gga ggt tta acc att gcc gca gca gcg      576
Val Thr Gly Gly Ser Gln Gly Gly Gly Leu Thr Ile Ala Ala Ala Ala
            180                 185                 190 ctg tca gac att cca aaa gcc gcg gtt gcc gat tat cct tat tta agc      624
Leu Ser Asp Ile Pro Lys Ala Ala Val Ala Asp Tyr Pro Tyr Leu Ser
        195                 200                 205 aac ttc gaa cgg gcc att gat gtg gcg ctt gaa cag ccg tac ctt gaa      672
Asn Phe Glu Arg Ala Ile Asp Val Ala Leu Glu Gln Pro Tyr Leu Glu
    210                 215                 220 atc aat tcc ttc ttc aga aga aat ggc agc ccg gaa aca gaa gtg cag      720
Ile Asn Ser Phe Phe Arg Arg Asn Gly Ser Pro Glu Thr Glu Val Gln
225                 230                 235                 240 gcg atg aag aca ctt tca tat ttc gat att atg aat ctc gct gac cga      768
Ala Met Lys Thr Leu Ser Tyr Phe Asp Ile Met Asn Leu Ala Asp Arg
                245                 250                 255 gtg aag gtg cct gtc ctg atg tca atc ggc ctg att gac aag gtc acg      816
Val Lys Val Pro Val Leu Met Ser Ile Gly Leu Ile Asp Lys Val Thr
            260                 265                 270 ccg cca tcc acc gtg ttt gcc gcc tac aat cat ttg gaa aca gag aaa      864
Pro Pro Ser Thr Val Phe Ala Ala Tyr Asn His Leu Glu Thr Glu Lys
        275                 280                 285 gag ctg aag gtg tac cgc tac ttc gga cat gag tat atc cct gct ttt      912
Glu Leu Lys Val Tyr Arg Tyr Phe Gly His Glu Tyr Ile Pro Ala Phe
    290                 295                 300 caa acg gaa aaa ctt gct ttc ttt aag cag cat ctt aaa ggc tga taa      960
Gln Thr Glu Lys Leu Ala Phe Phe Lys Gln His Leu Lys Gly
305                 310                 315
```

<210> SEQ ID NO 32
<211> LENGTH: 318
<212> TYPE: PRT
<213> ORGANISM: Bacillus subtilis ATCC 29233

<400> SEQUENCE: 32

```
Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
    50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125

Ser Pro His Gly His Ala Leu Gly Trp Met Thr Lys Gly Ile Leu Asp
    130                 135                 140

Lys Asp Thr Tyr Tyr Tyr Arg Gly Val Tyr Leu Asp Ala Val Arg Ala
```

```
                145                 150                 155                 160
Leu Glu Val Ile Ser Ser Phe Asp Glu Val Asp Glu Thr Arg Ile Gly
                165                 170                 175

Val Thr Gly Gly Ser Gln Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
    210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 33
<211> LENGTH: 24
<212> TYPE: DNA
<213> ORGANISM: artificial sequence
<220> FEATURE:
<223> OTHER INFORMATION: Primer

<400> SEQUENCE: 33
atgcagcagc cttatgatgt gccg                                              24

<210> SEQ ID NO 34
<211> LENGTH: 25
<212> TYPE: DNA
<213> ORGANISM: artificial sequence
<220> FEATURE:
<223> OTHER INFORMATION: Primer

<400> SEQUENCE: 34
ttatttcaga tgctttctca gaaac                                             25

<210> SEQ ID NO 35
<211> LENGTH: 27
<212> TYPE: DNA
<213> ORGANISM: artificial sequence
<220> FEATURE:
<223> OTHER INFORMATION: Primer

<400> SEQUENCE: 35
atggcacaat tatatgatat gcctttg                                           27

<210> SEQ ID NO 36
<211> LENGTH: 28
<212> TYPE: DNA
<213> ORGANISM: artificial sequence
<220> FEATURE:
<223> OTHER INFORMATION: Primer

<400> SEQUENCE: 36
ttacggattc agctcatcca taagtatc                                          28
```

```
<210> SEQ ID NO 37
<211> LENGTH: 24
<212> TYPE: DNA
<213> ORGANISM: artificial sequence
<220> FEATURE:
<223> OTHER INFORMATION: Primer

<400> SEQUENCE: 37
atgcagctgt ttgacctgag cctg                                                24

<210> SEQ ID NO 38
<211> LENGTH: 27
<212> TYPE: DNA
<213> ORGANISM: artificial sequence
<220> FEATURE:
<223> OTHER INFORMATION: Primer

<400> SEQUENCE: 38
ttaggtggac agcagcaggt gcttttg                                             27

<210> SEQ ID NO 39
<211> LENGTH: 24
<212> TYPE: DNA
<213> ORGANISM: artificial sequence
<220> FEATURE:
<223> OTHER INFORMATION: Primer

<400> SEQUENCE: 39
atggctttct ttgacatgcc gctg                                                24

<210> SEQ ID NO 40
<211> LENGTH: 27
<212> TYPE: DNA
<213> ORGANISM: artificial sequence
<220> FEATURE:
<223> OTHER INFORMATION: Primer

<400> SEQUENCE: 40
ttagccttct tcgaacaggc gtttcag                                             27

<210> SEQ ID NO 41
<211> LENGTH: 978
<212> TYPE: DNA
<213> ORGANISM: artificial sequence
<220> FEATURE:
<223> OTHER INFORMATION: Synthetic construct

<400> SEQUENCE: 41
atggctttct ttgacatgcc gctggaagaa ctgaaaaagt accgtccgga acgttacgag         60 gaaaagact tgacgaatt ttggcgcgaa accctgaaag aatccgaggg tttcccactg          120
gacccggtat ttgaaaaagt tgacttccac ctgaagaccg tcgaaactta cgacgtcacc        180
ttcagcggtt atcgtggcca gcgtatcaaa ggttggctgc tggtaccgaa actggcggaa        240
gagaaactgc cgtgtgttgt tcagtacatt ggttacaacg gtggccgtgg tttcccgcac        300
gactggctgt tctggccgtc tatgggttac atctgcttcg ttatggacac cgtggtcag         360 ggtagcggtt ggatgaaggg tgatactccg gactacccgg aaggtccggt ggacccgcag        420
tacccgggct tcatgacgcg cggcatcctg gatcctggca cctattacta ccgtcgtgtg        480
tttgtcgatg ccgtgcgcgc cgttgaagcc gctatcagct cccacgcgt cgattctcgt         540 aaagtggtag ttgctggtgg ctctcaaggt ggcggcattg cactggcagt ttccgcgctg        600
tccaaccgtg ttaaagccct gctgtgcgat gttccgttcc tgtgccactt ccgtcgtgcg        660
```

```
gtacagctgg tggacaccca cccgtacgta gaaattacga acttcctgaa aacccatcgt    720
gataaagaag agatcgtatt ccgtaccctg tcttactttg atggcgttaa ttttgcggct    780
cgtgcaaaag taccggcgct gttcagcgta ggtctgatgg acactatttg tccgccgtct    840
accgtattcg cagcctacaa ccactacgct ggtccgaaag aaatccgcat ctacccgtac    900
aacaaccacg aaggtggtgg ttctttccag gcaatcgaac aggttaaatt cctgaaacgc    960
ctgttcgaag aaggctaa                                                  978

<210> SEQ ID NO 42
<211> LENGTH: 795
<212> TYPE: DNA
<213> ORGANISM: artificial sequence
<220> FEATURE:
<223> OTHER INFORMATION: Primer

<400> SEQUENCE: 42
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
caggacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catctcacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctaa                                                     795

<210> SEQ ID NO 43
<211> LENGTH: 3434
<212> TYPE: DNA
<213> ORGANISM: artificial sequence
<220> FEATURE:
<223> OTHER INFORMATION: Plasmid pKD13

<400> SEQUENCE: 43
agattgcagc attacacgtc ttgagcgatt gtgtaggctg agctgcttc gaagttccta     60 tactttctag agaataggaa cttcggaata ggaacttcaa gatcccctta ttagaagaac    120
tcgtcaagaa ggcgatagaa ggcgatgcgc tgcgaatcgg gagcggcgat accgtaaagc    180
acgaggaagc ggtcagccca ttcgccgcca agctcttcag caatatcacg ggtagccaac    240
gctatgtcct gatagcggtc cgccacaccc agccggccac agtcgatgaa tccagaaaag    300
cggccatttt ccaccatgat attcggcaag caggcatcgc catgggtcac gacgagatcc    360
tcgccgtcgg gcatgcgcgc cttgagcctg gcgaacagtt cggctggcgc gagcccctga    420
tgctcttcgt ccagatcatc ctgatcgaca agaccggctt ccatccgagt acgtgctcgc    480
tcgatgcgat gtttcgcttg gtggtcgaat gggcaggtag ccggatcaag cgtatgcagc    540
cgccgcattg catcagccat gatggatact ttctcggcag gagcaaggtg agatgacagg    600
```

```
agatcctgcc ccggcacttc gcccaatagc agccagtccc ttcccgcttc agtgacaacg    660
tcgagcacag ctgcgcaagg aacgcccgtc gtggccagcc acgatagccg cgctgcctcg    720
tcctgcagtt cattcagggc accggacagg tcggtcttga caaaaagaac cgggcgcccc    780
tgcgctgaca gccggaacac ggcggcatca gagcagccga ttgtctgttg tgcccagtca    840
tagccgaata gcctctccac ccaagcggcc ggagaacctg cgtgcaatcc atcttgttca    900
atcatgcgaa acgatcctca tcctgtctct tgatcagatc ttgatcccct cgccatcag    960 atccttggcg gcaagaaagc catccagttt actttgcagg gcttcccaac cttaccagag   1020
ggcgccccag ctggcaattc cggttcgctt gctgtccata aaaccgccca gtctagctat   1080
cgccatgtaa gcccactgca agctacctgc tttctctttg cgcttgcgtt ttcccttgtc   1140
cagatagccc agtagctgac attcatccgg ggtcagcacc gtttctgcgg actggctttc   1200
tacgtgttcc gcttccttta gcagcccttg cgccctgagt gcttgcggca gcgtgagctt   1260
caaaagcgct ctgaagttcc tatactttct agagaatagg aacttcgaac tgcaggtcga   1320
cggatccccg gaattaattc tcatgtttga cagcttatca ctgatcagtg aattaatggc   1380
gatgacgcat cctcacgata atatccgggt aggcgcaatc actttcgtct ctactccgtt   1440
acaaagcgag gctgggtatt tcccggcctt tctgttatcc gaaatccact gaaagcacag   1500
cggctggctg aggagataaa taataaacga ggggctgtat gcacaaagca tcttctgttg   1560
agttaagaac gagtatcgag atggcacata gccttgctca aattggaatc aggtttgtgc   1620
caataccagt agaaacagac gaagaagcta gctttgcact ggattgcgag gctttgccat   1680
ggctaattcc catgtcagcc gttaagtgtt cctgtgtcac tgaaaattgc tttgagaggc   1740
tctaagggct tctcagtgcg ttacatccct ggcttgttgt ccacaaccgt taaaccttaa   1800
aagctttaaa agccttatat attcttttt ttcttataaa acttaaaacc ttagaggcta   1860
tttaagttgc tgatttatat taattttatt gttcaaacat gagagcttag tacgtgaaac   1920
atgagagctt agtacgttag ccatgagagc ttagtacgtt agccatgagg gtttagttcg   1980
ttaaacatga gagcttagta cgttaaacat gagagcttag tacgtgaaac atgagagctt   2040
agtacgtact atcaacaggt tgaactgcgg atcttgcggc cgcaaaaatt aaaaatgaag   2100
ttttaaatca atctaaagta tatatgagta aacttggtct gacagttacc aatgcttaat   2160
cagtgaggca cctatctcag cgatctgtct atttcgttca tccatagttg cctgactccc   2220
cgtcgtgtag ataactacga tacgggaggg cttaccatct ggccccagtg ctgcaatgat   2280
accgcgagac ccacgctcac cggctccaga tttatcagca ataaaccagc cagccggaag   2340
ggccgagcgc agaagtggtc ctgcaacttt atccgcctcc atccagtcta ttaattgttg   2400
ccgggaagct agagtaagta gttcgccagt taatagtttg cgcaacgttg ttgccattgc   2460
tacaggcatc gtggtgtcac gctcgtcgtt tggtatggct tcattcagct ccggttccca   2520
acgatcaagg cgagttacat gatcccccat gttgtgcaaa aaagcggtta gctccttcgg   2580
tcctccgatc gttgtcagaa gtaagttggc cgcagtgtta tcactcatgg ttatggcagc   2640
actgcataat tctcttactg tcatgccatc cgtaagatgc ttttctgtga ctggtgagta   2700
ctcaaccaag tcattctgag aatagtgtat gcggcgaccg agttgctctt gcccggcgtc   2760
aatacgggat aataccgcgc cacatagcag aactttaaaa gtgctcatca ttggaaaacg   2820
ttcttcgggg cgaaaactct caaggatctt accgctgttg agatccagtt cgatgtaacc   2880
cactcgtgca cccaactgat cttcagcatc ttttactttc accagcgttt ctgggtgagc   2940
aaaaacagga aggcaaaatg ccgcaaaaaa gggaataagg gcgacacgga aatgttgaat   3000
```

| | | |
|---|---|---|
| actcatactc ttcctttttc aatattattg aagcatttat cagggttatt gtctcatgag | 3060 | |
| cggatacata tttgaatgta tttagaaaaa taaacaaata ggggttccgc gcacatttcc | 3120 | |
| ccgaaaagtg ccacctgcat cgatggcccc ccgatggtag tgtggggtct ccccatgcga | 3180 | |
| gagtagggaa ctgccaggca tcaaataaaa cgaaaggctc agtcgaaaga ctgggccttt | 3240 | |
| cgttttatct gttgtttgtc ggtgaacgct ctcctgagta ggacaaatcc gccgggagcg | 3300 | |
| gatttgaacg ttgcgaagca acggcccgga gggtggcggg caggacgccc gccataaact | 3360 | |
| gccaggcatc aaattaagca gaaggccatc ctgacggatg ccttttttgc gtggccagtg | 3420 | |
| ccaagcttgc atgc | 3434 | |

<210> SEQ ID NO 44
<211> LENGTH: 80
<212> TYPE: DNA
<213> ORGANISM: artificial sequence
<220> FEATURE:
<223> OTHER INFORMATION: Primer

<400> SEQUENCE: 44

| | | |
|---|---|---|
| atgagcacgt cagacgatat ccataacacc acagccactg gcaaatgccc gttccatcag | 60 | |
| gtgtaggctg gagctgcttc | 80 | |

<210> SEQ ID NO 45
<211> LENGTH: 82
<212> TYPE: DNA
<213> ORGANISM: artificial sequence
<220> FEATURE:
<223> OTHER INFORMATION: Primer

<400> SEQUENCE: 45

| | | |
|---|---|---|
| taacagcagg tcgaaacggt cgaggttcat cactttcacc catgccgcca cgaagtcttt | 60 | |
| attccgggga tccgtcgacc tg | 82 | |

<210> SEQ ID NO 46
<211> LENGTH: 1424
<212> TYPE: DNA
<213> ORGANISM: artificial sequence
<220> FEATURE:
<223> OTHER INFORMATION: Synthetic construct

<400> SEQUENCE: 46

| | | |
|---|---|---|
| taacagcagg tcgaaacggt cgaggttcat cactttcacc catgccgcca cgaagtcttt | 60 | |
| attccgggga tccgtcgacc tgcagttcga agttcctatt ctctagaaag tataggaact | 120 | |
| tcagagcgct tttgaagctc acgctgccgc aagcactcag ggcgcaaggg ctgctaaagg | 180 | |
| aagcggaaca cgtagaaagc cagtccgcag aaacggtgct gacccccggat gaatgtcagc | 240 | |
| tactgggcta tctggacaag gaaaacgca agcgcaaaga gaaagcaggt agcttgcagt | 300 | |
| gggcttacat ggcgatagct agactgggcg gttttatgga cagcaagcga accggaattg | 360 | |
| ccagctgggg cgccctctgg taaggttggg aagccctgca aagtaaactg gatggctttc | 420 | |
| ttgccgccaa ggatctgatg gcgcagggga tcaagatctg atcaagagac aggatgagga | 480 | |
| tcgtttcgca tgattgaaca agatggattg cacgcaggtt ctccggccgc ttgggtggag | 540 | |
| aggctattcg gctatgactg ggcacaacag acaatcggct gctctgatgc cgccgtgttc | 600 | |
| cggctgtcag cgcaggggcg cccggttctt tttgtcaaga ccgacctgtc cggtgccctg | 660 | |
| aatgaactgc aggacgaggc agcgcggcta tcgtggctgg ccacgacggg cgttccttgc | 720 | |
| gcagctgtgc tcgacgttgt cactgaagcg ggaagggact ggctgctatt gggcgaagtg | 780 | |

-continued

```
ccggggcagg atctcctgtc atctcacctt gctcctgccg agaaagtatc catcatggct      840
gatgcaatgc ggcggctgca tacgcttgat ccggctacct gcccattcga ccaccaagcg      900
aaacatcgca tcgagcgagc acgtactcgg atggaagccg tcttgtcga tcaggatgat      960 ctggacgaag agcatcaggg gctcgcgcca gccgaactgt tcgccaggct caaggcgcgc     1020
atgcccgacg gcgaggatct cgtcgtgacc catggcgatg cctgcttgcc gaatatcatg     1080
gtggaaaatg gccgcttttc tggattcatc gactgtggcc ggctgggtgt ggcggaccgc     1140
tatcaggaca tagcgttggc tacccgtgat attgctgaag agcttggcgg cgaatgggct     1200
gaccgcttcc tcgtgcttta cggtatcgcc gctcccgatt cgcagcgcat cgccttctat     1260
cgccttcttg acgagttctt ctaataaggg gatcttgaag ttcctattcc gaagttccta     1320
ttctctagaa agtataggaa cttcgaagca gctccagcct acacctgatg gaacgggcat     1380
ttgccagtgg ctgtggtgtt atggatatcg tctgacgtgc tcat                     1424
```

```
<210> SEQ ID NO 47
<211> LENGTH: 2181
<212> TYPE: DNA
<213> ORGANISM: Escherichia coli
<220> FEATURE:
<221> NAME/KEY: CDS
<222> LOCATION: (1)..(2181)

<400> SEQUENCE: 47
```

```
atg agc acg tca gac gat atc cat aac acc aca gcc act ggc aaa tgc       48
Met Ser Thr Ser Asp Asp Ile His Asn Thr Thr Ala Thr Gly Lys Cys
1               5                  10                  15 ccg ttc cat cag ggc ggt cac gac cag agt gcg ggg gcg ggc aca acc       96
Pro Phe His Gln Gly Gly His Asp Gln Ser Ala Gly Ala Gly Thr Thr
            20                  25                  30 act cgc gac tgg tgg cca aat caa ctt cgt gtt gac ctg tta aac caa      144
Thr Arg Asp Trp Trp Pro Asn Gln Leu Arg Val Asp Leu Leu Asn Gln
        35                  40                  45 cat tct aat cgt tct aac cca ctg ggt gag gac ttt gac tac cgc aaa      192
His Ser Asn Arg Ser Asn Pro Leu Gly Glu Asp Phe Asp Tyr Arg Lys
    50                  55                  60 gaa ttc agc aaa tta gat tac tac ggc ctg aaa aaa gat ctg aaa gcc      240
Glu Phe Ser Lys Leu Asp Tyr Tyr Gly Leu Lys Lys Asp Leu Lys Ala
65                  70                  75                  80 ctg ttg aca gaa tct caa ccg tgg tgg cca gcc gac tgg ggc agt tac      288
Leu Leu Thr Glu Ser Gln Pro Trp Trp Pro Ala Asp Trp Gly Ser Tyr
                85                  90                  95 gcc ggt ctg ttt att cgt atg gcc tgg cac ggc gcg ggg act tac cgt      336
Ala Gly Leu Phe Ile Arg Met Ala Trp His Gly Ala Gly Thr Tyr Arg
            100                 105                 110 tca atc gat gga cgc ggt ggc gcg ggt cgt ggt cag caa cgt ttt gca      384
Ser Ile Asp Gly Arg Gly Gly Ala Gly Arg Gly Gln Gln Arg Phe Ala
        115                 120                 125 ccg ctg aac tcc tgg ccg gat aac gta agc ctc gat aaa gcg cgt cgc      432
Pro Leu Asn Ser Trp Pro Asp Asn Val Ser Leu Asp Lys Ala Arg Arg
    130                 135                 140 ctg ttg tgg cca atc aaa cag aaa tat ggt cag aaa atc tcc tgg gcc      480
Leu Leu Trp Pro Ile Lys Gln Lys Tyr Gly Gln Lys Ile Ser Trp Ala
145                 150                 155                 160 gac ctg ttt atc ctc gcg ggt aac gtg gcg cta gaa aac tcc ggc ttc      528
Asp Leu Phe Ile Leu Ala Gly Asn Val Ala Leu Glu Asn Ser Gly Phe
                165                 170                 175 cgt acc ttc ggt ttt ggt gcc ggt cgt gaa gac gtc tgg gaa ccg gat      576
Arg Thr Phe Gly Phe Gly Ala Gly Arg Glu Asp Val Trp Glu Pro Asp
            180                 185                 190
```

```
ctg gat gtt aac tgg ggt gat gaa aaa gcc tgg ctg act cac cgt cat    624
Leu Asp Val Asn Trp Gly Asp Glu Lys Ala Trp Leu Thr His Arg His
        195                 200                 205 ccg gaa gcg ctg gcg aaa gca ccg ctg ggt gca acc gag atg ggt ctg    672
Pro Glu Ala Leu Ala Lys Ala Pro Leu Gly Ala Thr Glu Met Gly Leu
210                 215                 220 att tac gtt aac ccg gaa ggc ccg gat cac agc ggt gaa ccg ctt tct    720
Ile Tyr Val Asn Pro Glu Gly Pro Asp His Ser Gly Glu Pro Leu Ser
225                 230                 235                 240 gcg gca gca gct atc cgc gcg acc ttc ggc aac atg ggc atg aac gac    768
Ala Ala Ala Ala Ile Arg Ala Thr Phe Gly Asn Met Gly Met Asn Asp
                245                 250                 255 gaa gaa acc gtg gcg ctg att gcg ggt ggt cat acg ctg ggt aaa acc    816
Glu Glu Thr Val Ala Leu Ile Ala Gly Gly His Thr Leu Gly Lys Thr
            260                 265                 270 cac ggt gcc ggt ccg aca tca aat gta ggt cct gat cca gaa gct gca    864
His Gly Ala Gly Pro Thr Ser Asn Val Gly Pro Asp Pro Glu Ala Ala
        275                 280                 285 ccg att gaa gaa caa ggt tta ggt tgg gcg agc act tac ggc agc ggc    912
Pro Ile Glu Glu Gln Gly Leu Gly Trp Ala Ser Thr Tyr Gly Ser Gly
290                 295                 300 gtt ggc gca gat gcc att acc tct ggt ctg gaa gta gtc tgg acc cag    960
Val Gly Ala Asp Ala Ile Thr Ser Gly Leu Glu Val Val Trp Thr Gln
305                 310                 315                 320 acg ccg acc cag tgg agc aac tat ttc ttc gag aac ctg ttc aag tat   1008
Thr Pro Thr Gln Trp Ser Asn Tyr Phe Phe Glu Asn Leu Phe Lys Tyr
                325                 330                 335 gag tgg gta cag acc cgc agc ccg gct ggc gca atc cag ttc gaa gcg   1056
Glu Trp Val Gln Thr Arg Ser Pro Ala Gly Ala Ile Gln Phe Glu Ala
            340                 345                 350 gta gac gca ccg gaa att atc ccg gat ccg ttt gat ccg tcg aag aaa   1104
Val Asp Ala Pro Glu Ile Ile Pro Asp Pro Phe Asp Pro Ser Lys Lys
        355                 360                 365 cgt aaa ccg aca atg ctg gtg acc gac ctg acg ctg cgt ttt gat cct   1152
Arg Lys Pro Thr Met Leu Val Thr Asp Leu Thr Leu Arg Phe Asp Pro
370                 375                 380 gag ttc gag aag atc tct cgt cgt ttc ctc aac gat ccg cag gcg ttc   1200
Glu Phe Glu Lys Ile Ser Arg Arg Phe Leu Asn Asp Pro Gln Ala Phe
385                 390                 395                 400 aac gaa gcc ttt gcc cgt gcc tgg ttc aaa ctg acg cac agg gat atg   1248
Asn Glu Ala Phe Ala Arg Ala Trp Phe Lys Leu Thr His Arg Asp Met
                405                 410                 415 ggg ccg aaa tct cgc tac atc ggg ccg gaa gtg ccg aaa gaa gat ctg   1296
Gly Pro Lys Ser Arg Tyr Ile Gly Pro Glu Val Pro Lys Glu Asp Leu
            420                 425                 430 atc tgg caa gat ccg ctg ccg cag ccg atc tac aac ccg acc gag cag   1344
Ile Trp Gln Asp Pro Leu Pro Gln Pro Ile Tyr Asn Pro Thr Glu Gln
        435                 440                 445 gac att atc gat ctg aaa ttc gcg att gcg gat tct ggt ctg tct gtt   1392
Asp Ile Ile Asp Leu Lys Phe Ala Ile Ala Asp Ser Gly Leu Ser Val
450                 455                 460 agt gag ctg gta tcg gtg gcc tgg gca tct gct tct acc ttc cgt ggt   1440
Ser Glu Leu Val Ser Val Ala Trp Ala Ser Ala Ser Thr Phe Arg Gly
465                 470                 475                 480 ggc gac aaa cgc ggt ggt gcc aac ggt gcg cgt ctg gca tta atg ccg   1488
Gly Asp Lys Arg Gly Gly Ala Asn Gly Ala Arg Leu Ala Leu Met Pro
                485                 490                 495 cag cgc gac tgg gat gtg aac gcc gca gcc gtt cgt gct ctg cct gtt   1536
Gln Arg Asp Trp Asp Val Asn Ala Ala Ala Val Arg Ala Leu Pro Val
            500                 505                 510
```

| | | | | | | | | | | | | | | |
|---|---|---|---|---|---|---|---|---|---|---|---|---|---|---|
| ctg | gag | aaa | atc | cag | aaa | gag | tct | ggt | aaa | gcc | tcg | ctg | gcg | gat | atc | 1584 |
| Leu | Glu | Lys | Ile | Gln | Lys | Glu | Ser | Gly | Lys | Ala | Ser | Leu | Ala | Asp | Ile | |
| | | | 515 | | | | 520 | | | | 525 | | | | | |
| ata | gtg | ctg | gct | ggt | gtg | gtt | ggt | gtt | gag | aaa | gcc | gca | agc | gcc | gca | 1632 |
| Ile | Val | Leu | Ala | Gly | Val | Val | Gly | Val | Glu | Lys | Ala | Ala | Ser | Ala | Ala | |
| 530 | | | | | 535 | | | | | 540 | | | | | | |
| ggt | ttg | agc | att | cat | gta | ccg | ttt | gcg | ccg | ggt | cgc | gtt | gat | gcg | cgt | 1680 |
| Gly | Leu | Ser | Ile | His | Val | Pro | Phe | Ala | Pro | Gly | Arg | Val | Asp | Ala | Arg | |
| 545 | | | | 550 | | | | | 555 | | | | | 560 | | |
| cag | gat | cag | act | gac | att | gag | atg | ttt | gag | ctg | ctg | gag | cca | att | gct | 1728 |
| Gln | Asp | Gln | Thr | Asp | Ile | Glu | Met | Phe | Glu | Leu | Leu | Glu | Pro | Ile | Ala | |
| | | | | 565 | | | | 570 | | | | | 575 | | | |
| gac | ggt | ttc | cgt | aac | tat | cgc | gct | cgt | ctg | gac | gtt | tcc | acc | acc | gag | 1776 |
| Asp | Gly | Phe | Arg | Asn | Tyr | Arg | Ala | Arg | Leu | Asp | Val | Ser | Thr | Thr | Glu | |
| | | | 580 | | | | | 585 | | | | | 590 | | | |
| tca | ctg | ctg | atc | gac | aaa | gca | cag | caa | ctg | acg | ctg | acc | gcg | ccg | gaa | 1824 |
| Ser | Leu | Leu | Ile | Asp | Lys | Ala | Gln | Gln | Leu | Thr | Leu | Thr | Ala | Pro | Glu | |
| | | | 595 | | | | 600 | | | | | 605 | | | | |
| atg | act | gcg | ctg | gtg | ggc | ggc | atg | cgt | gta | ctg | ggt | gcc | aac | ttc | gat | 1872 |
| Met | Thr | Ala | Leu | Val | Gly | Gly | Met | Arg | Val | Leu | Gly | Ala | Asn | Phe | Asp | |
| | 610 | | | | | 615 | | | | | 620 | | | | | |
| ggc | agc | aaa | aac | ggc | gtc | ttc | act | gac | cgc | gtt | ggc | gta | ttg | agc | aat | 1920 |
| Gly | Ser | Lys | Asn | Gly | Val | Phe | Thr | Asp | Arg | Val | Gly | Val | Leu | Ser | Asn | |
| 625 | | | | | 630 | | | | | 635 | | | | | 640 | |
| gac | ttc | ttc | gtg | aac | ttg | ctg | gat | atg | cgt | tac | gag | tgg | aaa | gcg | acc | 1968 |
| Asp | Phe | Phe | Val | Asn | Leu | Leu | Asp | Met | Arg | Tyr | Glu | Trp | Lys | Ala | Thr | |
| | | | | 645 | | | | | 650 | | | | | 655 | | |
| gac | gaa | tcg | aaa | gag | ctg | ttc | gaa | ggc | cgt | gac | cgt | gaa | acc | ggc | gaa | 2016 |
| Asp | Glu | Ser | Lys | Glu | Leu | Phe | Glu | Gly | Arg | Asp | Arg | Glu | Thr | Gly | Glu | |
| | | | 660 | | | | | 665 | | | | | 670 | | | |
| gtg | aaa | ttt | acg | gcc | agc | cgt | gcg | gat | ctg | gtg | ttt | ggt | tct | aac | tcc | 2064 |
| Val | Lys | Phe | Thr | Ala | Ser | Arg | Ala | Asp | Leu | Val | Phe | Gly | Ser | Asn | Ser | |
| | | | 675 | | | | | 680 | | | | | 685 | | | |
| gtc | ctg | cgt | gcg | gtg | gcg | gaa | gtt | tac | gcc | agt | agc | gat | gcc | cac | gag | 2112 |
| Val | Leu | Arg | Ala | Val | Ala | Glu | Val | Tyr | Ala | Ser | Ser | Asp | Ala | His | Glu | |
| | | 690 | | | | | 695 | | | | | 700 | | | | |
| aag | ttt | gtt | aaa | gac | ttc | gtg | gcg | gca | tgg | gtg | aaa | gtg | atg | aac | ctc | 2160 |
| Lys | Phe | Val | Lys | Asp | Phe | Val | Ala | Ala | Trp | Val | Lys | Val | Met | Asn | Leu | |
| 705 | | | | 710 | | | | | 715 | | | | | 720 | | |
| gac | cgt | ttc | gac | ctg | ctg | taa | | | | | | | | | | 2181 |
| Asp | Arg | Phe | Asp | Leu | Leu | | | | | | | | | | | |
| | | | | 725 | | | | | | | | | | | | |

<210> SEQ ID NO 48
<211> LENGTH: 726
<212> TYPE: PRT
<213> ORGANISM: Escherichia coli

<400> SEQUENCE: 48

Met Ser Thr Ser Asp Asp Ile His Asn Thr Thr Ala Thr Gly Lys Cys
1               5                   10                  15

Pro Phe His Gln Gly Gly His Asp Gln Ser Ala Gly Ala Gly Thr Thr
            20                  25                  30

Thr Arg Asp Trp Trp Pro Asn Gln Leu Arg Val Asp Leu Leu Asn Gln
        35                  40                  45

His Ser Asn Arg Ser Asn Pro Leu Gly Glu Asp Phe Asp Tyr Arg Lys
    50                  55                  60

Glu Phe Ser Lys Leu Asp Tyr Tyr Gly Leu Lys Lys Asp Leu Lys Ala
65                  70                  75                  80

-continued

```
Leu Leu Thr Glu Ser Gln Pro Trp Trp Pro Ala Asp Trp Gly Ser Tyr
             85                  90                  95

Ala Gly Leu Phe Ile Arg Met Ala Trp His Gly Ala Gly Thr Tyr Arg
            100                 105                 110

Ser Ile Asp Gly Arg Gly Gly Ala Gly Arg Gly Gln Gln Arg Phe Ala
            115                 120                 125

Pro Leu Asn Ser Trp Pro Asp Asn Val Ser Leu Asp Lys Ala Arg Arg
            130                 135                 140

Leu Leu Trp Pro Ile Lys Gln Lys Tyr Gly Gln Lys Ile Ser Trp Ala
145                 150                 155                 160

Asp Leu Phe Ile Leu Ala Gly Asn Val Ala Leu Glu Asn Ser Gly Phe
                165                 170                 175

Arg Thr Phe Gly Phe Gly Ala Gly Arg Glu Asp Val Trp Glu Pro Asp
            180                 185                 190

Leu Asp Val Asn Trp Gly Asp Glu Lys Ala Trp Leu Thr His Arg His
            195                 200                 205

Pro Glu Ala Leu Ala Lys Ala Pro Leu Gly Ala Thr Glu Met Gly Leu
            210                 215                 220

Ile Tyr Val Asn Pro Glu Gly Pro Asp His Ser Gly Glu Pro Leu Ser
225                 230                 235                 240

Ala Ala Ala Ala Ile Arg Ala Thr Phe Gly Asn Met Gly Met Asn Asp
                245                 250                 255

Glu Glu Thr Val Ala Leu Ile Ala Gly His Thr Leu Gly Lys Thr
            260                 265                 270

His Gly Ala Gly Pro Thr Ser Asn Val Gly Pro Asp Pro Glu Ala Ala
            275                 280                 285

Pro Ile Glu Glu Gln Gly Leu Gly Trp Ala Ser Thr Tyr Gly Ser Gly
            290                 295                 300

Val Gly Ala Asp Ala Ile Thr Ser Gly Leu Glu Val Val Trp Thr Gln
305                 310                 315                 320

Thr Pro Thr Gln Trp Ser Asn Tyr Phe Phe Glu Asn Leu Phe Lys Tyr
                325                 330                 335

Glu Trp Val Gln Thr Arg Ser Pro Ala Gly Ala Ile Gln Phe Glu Ala
            340                 345                 350

Val Asp Ala Pro Glu Ile Ile Pro Asp Pro Phe Asp Pro Ser Lys Lys
            355                 360                 365

Arg Lys Pro Thr Met Leu Val Thr Asp Leu Thr Leu Arg Phe Asp Pro
            370                 375                 380

Glu Phe Glu Lys Ile Ser Arg Arg Phe Leu Asn Asp Pro Gln Ala Phe
385                 390                 395                 400

Asn Glu Ala Phe Ala Arg Ala Trp Phe Lys Leu Thr His Arg Asp Met
                405                 410                 415

Gly Pro Lys Ser Arg Tyr Ile Gly Pro Glu Val Pro Lys Glu Asp Leu
            420                 425                 430

Ile Trp Gln Asp Pro Leu Pro Gln Pro Ile Tyr Asn Pro Thr Glu Gln
            435                 440                 445

Asp Ile Ile Asp Leu Lys Phe Ala Ile Ala Asp Ser Gly Leu Ser Val
            450                 455                 460

Ser Glu Leu Val Ser Val Ala Trp Ala Ser Ala Ser Thr Phe Arg Gly
465                 470                 475                 480

Gly Asp Lys Arg Gly Gly Ala Asn Gly Ala Arg Leu Ala Leu Met Pro
                485                 490                 495

Gln Arg Asp Trp Asp Val Asn Ala Ala Ala Val Arg Ala Leu Pro Val
            500                 505                 510
```

```
Leu Glu Lys Ile Gln Lys Glu Ser Gly Lys Ala Ser Leu Ala Asp Ile
            515                 520                 525
Ile Val Leu Ala Gly Val Val Gly Val Glu Lys Ala Ala Ser Ala Ala
            530                 535                 540
Gly Leu Ser Ile His Val Pro Phe Ala Pro Gly Arg Val Asp Ala Arg
545                 550                 555                 560
Gln Asp Gln Thr Asp Ile Glu Met Phe Glu Leu Leu Glu Pro Ile Ala
            565                 570                 575
Asp Gly Phe Arg Asn Tyr Arg Ala Arg Leu Asp Val Ser Thr Thr Glu
            580                 585                 590
Ser Leu Leu Ile Asp Lys Ala Gln Gln Leu Thr Leu Thr Ala Pro Glu
            595                 600                 605
Met Thr Ala Leu Val Gly Gly Met Arg Val Leu Gly Ala Asn Phe Asp
            610                 615                 620
Gly Ser Lys Asn Gly Val Phe Thr Asp Arg Val Gly Val Leu Ser Asn
625                 630                 635                 640
Asp Phe Phe Val Asn Leu Leu Asp Met Arg Tyr Glu Trp Lys Ala Thr
            645                 650                 655
Asp Glu Ser Lys Glu Leu Phe Glu Gly Arg Asp Arg Glu Thr Gly Glu
            660                 665                 670
Val Lys Phe Thr Ala Ser Arg Ala Asp Leu Val Phe Gly Ser Asn Ser
            675                 680                 685
Val Leu Arg Ala Val Ala Glu Val Tyr Ala Ser Ser Asp Ala His Glu
            690                 695                 700
Lys Phe Val Lys Asp Phe Val Ala Ala Trp Val Lys Val Met Asn Leu
705                 710                 715                 720
Asp Arg Phe Asp Leu Leu
            725

<210> SEQ ID NO 49
<211> LENGTH: 6329
<212> TYPE: DNA
<213> ORGANISM: artificial sequence
<220> FEATURE:
<223> OTHER INFORMATION: Plasmid pKD46

<400> SEQUENCE: 49
catcgattta ttatgacaac ttgacggcta catcattcac ttttcttca caaccggcac      60 ggaactcgct cgggctggcc ccggtgcatt ttttaaatac ccgcgagaaa tagagttgat    120
cgtcaaaacc aacattgcga ccgacggtgg cgataggcat ccgggtggtg ctcaaaagca    180
gcttcgcctg gctgatacgt tggtcctcgc gccagcttaa gacgctaatc cctaactgct    240
ggcggaaaag atgtgacaga cgcgacggcg acaagcaaac atgctgtgcg acgctggcga    300
tatcaaaatt gctgtctgcc aggtgatcgc tgatgtactg acaagcctcg cgtacccgat    360
tatccatcgg tggatggagc gactcgttaa tcgcttccat gcgccgcagt aacaattgct    420
caagcagatt tatcgccagc agctccgaat agcgcccttc cccttgcccg gcgttaatga    480
tttgcccaaa caggtcgctg aaatgcggct ggtgcgcttc atccgggcga agaaccccg     540 tattggcaaa tattgacggc cagttaagcc attcatgcca gtaggcgcgc ggacgaaagt    600
aaacccactg gtgataccat tcgcgagcct ccggatgacg accgtagtga tgaatctctc    660
ctggcgggaa cagcaaaata tcacccggtc ggcaaacaaa ttctcgtccc tgatttttca    720
ccaccccctg accgcgaatg gtgagattga gaatataacc tttcattccc agcggtcggt    780
cgataaaaaa atcgagataa ccgttggcct caatcggcgt taaacccgcc accagatggg    840
```

```
cattaaacga gtatcccggc agcaggggat cattttgcgc ttcagccata ctttcatac      900
tcccgccatt cagagaagaa accaattgtc catattgcat cagacattgc cgtcactgcg     960
tcttttactg gctcttctcg ctaaccaaac cggtaacccc gcttattaaa agcattctgt    1020
aacaaagcgg gaccaaagcc atgacaaaaa cgcgtaacaa aagtgtctat aatcacggca    1080
gaaaagtcca cattgattat ttgcacggcg tcacactttg ctatgccata gcatttttat    1140
ccataagatt agcggatcct acctgacgct ttttatcgca actctctact gtttctccat    1200
acccgttttt ttgggaattc gagctctaag gaggttataa aaatggata ttaatactga     1260
aactgagatc aagcaaaagc attcactaac cccctttcct gttttcctaa tcagcccggc    1320
atttcgcggg cgatattttc acagctattt caggagttca gccatgaacg cttattacat    1380
tcaggatcgt cttgaggctc agagctgggc gcgtcactac cagcagctcg cccgtgaaga    1440
gaaagaggca gaactggcag acgacatgga aaaaggcctg ccccagcacc tgtttgaatc    1500
gctatgcatc gatcatttgc aacgccacg ggccagcaaa aaatccatta cccgtgcgtt     1560
tgatgacgat gttgagtttc aggagcgcat ggcagaacac atccggtaca tggttgaaac    1620
cattgctcac caccaggttg atattgattc agaggtataa aacgaatgag tactgcactc    1680
gcaacgctgg ctgggaagct ggctgaacgt gtcggcatgg attctgtcga cccacaggaa    1740
ctgatcacca ctcttcgcca gacggcattt aaaggtgatg ccagcgatgc gcagttcatc    1800
gcattactga tcgttgccaa ccagtacggc cttaatccgt ggacgaaaga aatttacgcc    1860
tttcctgata agcagaatgg catcgttccg gtggtgggcg ttgatggctg gtcccgcatc    1920
atcaatgaaa accagcagtt tgatggcatg gactttgagc aggacaatga atcctgtaca    1980
tgccggattt accgcaagga ccgtaatcat ccgatctgcg ttaccgaatg gatggatgaa    2040
tgccgccgcg aaccattcaa aactcgcgaa ggcagagaaa tcacggggcc gtggcagtcg    2100
catcccaaac ggatgttacg tcataaagcc atgattcagt gtgcccgtct ggccttcgga    2160
tttgctggta tctatgacaa ggatgaagcc gagcgcattg tcgaaaatac tgcatacact    2220
gcagaacgtc agccggaacg cgacatcact ccggttaacg atgaaaccat gcaggagatt    2280
aacactctgc tgatcgccct ggataaaaca tgggatgacg acttattgcc gctctgttcc    2340
cagatatttc gccgcgacat tcgtgcatcg tcagaactga cacaggccga agcagtaaaa    2400
gctcttggat tcctgaaaca gaaagccgca gagcagaagg tggcagcatg acaccggaca    2460
ttatcctgca gcgtaccggg atcgatgtga gagctgtcga acaggggat gatgcgtggc     2520
acaaattacg gctcggcgtc atcaccgctt cagaagttca caacgtgata gcaaacccc     2580
gctccggaaa gaagtggcct gacatgaaaa tgtcctactt ccacaccctg cttgctgagg    2640
tttgcaccgg tgtggctccg gaagttaacg ctaaagcact ggcctgggga aaacagtacg    2700
agaacgacgc cagaaccctg tttgaattca cttccggcgt gaatgttact gaatccccga    2760
tcatctatcg cgacgaaagt atgcgtaccg cctgctctcc cgatggttta tgcagtgacg    2820
gcaacggcct tgaactgaaa tgcccgttta cctcccggga tttcatgaag ttccggctcg    2880
gtggtttcga ggccataaag tcagcttaca tggcccaggt gcagtacagc atgtgggtga    2940
cgcgaaaaaa tgcctggtac tttgccaact atgacccgcg tatgaagcgt gaaggcctgc    3000
attatgtcgt gattgagcgg gatgaaaagt acatggcgag ttttgacgag atcgtgccgg    3060
agttcatcga aaaaatggac gaggcactgg ctgaaattgg ttttgtattt ggggagcaat    3120
ggcgatgacg catcctcacg ataatatccg ggtaggcgca atcacttcg tctactccgt     3180
tacaaagcga ggctgggtat ttcccggcct ttctgttatc cgaaatccac tgaaagcaca    3240
```

```
gcggctggct gaggagataa ataataaacg aggggctgta tgcacaaagc atcttctgtt    3300
gagttaagaa cgagtatcga gatggcacat agccttgctc aaattggaat caggtttgtg    3360
ccaataccag tagaaacaga cgaagaatcc atgggtatgg acagttttcc ctttgatatg    3420
taacggtgaa cagttgttct acttttgttt gttagtcttg atgcttcact gatagataca    3480
agagccataa gaacctcaga tccttccgta tttagccagt atgttctcta gtgtggttcg    3540 ttgttttgc gtgagccatg agaacgaacc attgagatca tacttacttt gcatgtcact    3600
caaaaatttt gcctcaaaac tggtgagctg aattttttgca gttaaagcat cgtgtagtgt    3660
ttttcttagt ccgttacgta ggtaggaatc tgatgtaatg gttgttggta ttttgtcacc    3720
attcattttt atctggttgt tctcaagttc ggttacgaga tccatttgtc tatctagttc    3780
aacttggaaa atcaacgtat cagtcgggcg gcctcgctta tcaaccacca atttcatatt    3840
gctgtaagtg tttaaatctt tacttattgg tttcaaaacc cattggttaa gccttttaaa    3900
ctcatggtag ttattttcaa gcattaacat gaacttaaat tcatcaaggc taatctctat    3960
atttgccttg tgagttttct tttgtgttag ttctttaat aaccactcat aaatcctcat    4020
agagtatttg ttttcaaaag acttaacatg ttccagatta tattttatga atttttttaa    4080
ctggaaaaga taaggcaata tctcttcact aaaaactaat tctaattttt cgcttgagaa    4140
cttggcatag tttgtccact ggaaaatctc aaagccttta accaaggat tcctgatttc    4200 cacagttctc gtcatcagct ctctggttgc tttagctaat acaccataag catttccct    4260 actgatgttc atcatctgag cgtattggtt ataagtgaac gataccgtcc gttcttcct    4320 tgtagggttt tcaatcgtgg ggttgagtag tgccacacag cataaaatta gcttggtttc    4380
atgctccgtt aagtcatagc gactaatcgc tagttcattt gctttgaaaa caactaattc    4440
agacatacat ctcaattggt ctaggtgatt ttaatcacta taccaattga gatgggctag    4500
tcaatgataa ttactagtcc ttttcctttg agttgtgggt atctgtaaat tctgctagac    4560
ctttgctgga aaacttgtaa attctgctag accctctgta aattccgcta gacctttgtg    4620 tgttttttt gtttatattc aagtggttat aatttataga ataagaaag aataaaaaaa    4680 gataaaaga atagatccca gccctgtgta taactcacta ctttagtcag ttccgcagta    4740 ttacaaagg atgtcgcaaa cgctgtttgc tcctctacaa aacagacctt aaaaccctaa    4800
aggcttaagt agcaccctcg caagctcggt tgcggccgca atcgggcaaa tcgctgaata    4860 ttcctttgt ctccgaccat caggcacctg agtcgctgtc ttttcgtga cattcagttc    4920 gctgcgctca cggctctggc agtgaatggg ggtaaatggc actacaggcg ccttttatgg    4980
attcatgcaa ggaaactacc cataatacaa gaaaagcccg tcacgggctt ctcagggcgt    5040
tttatggcgg gtctgctatg tggtgctatc tgactttttg ctgttcagca gttcctgccc    5100
tctgattttc cagtctgacc acttcggatt atcccgtgac aggtcattca gactggctaa    5160
tgcacccagt aaggcagcgg tatcatcaac ggggtctgac gctcagtgga acgaaaactc    5220
acgttaaggg attttggtca tgagattatc aaaaaggatc ttcacctaga tccttttaaa    5280
ttaaaaatga agttttaaat caatctaaag tatatatgag taaacttggt ctgacagtta    5340
ccaatgctta atcagtgagg cacctatctc agcgatctgt ctatttcgtt catccatagt    5400
tgcctgactc cccgtcgtgt agataactac gatacgggga ggcttaccat ctggccccag    5460
tgctgcaatg ataccgcgag acccacgctc accggctcca gatttatcag caataaacca    5520
gccagccgga agggccgagc gcagaagtgg tcctgcaact ttatccgcct ccatccagtc    5580
tattaattgt tgccgggaag ctagagtaag tagttcgcca gttaatagtt tgcgcaacgt    5640
```

```
tgttgccatt gctacaggca tcgtggtgtc acgctcgtcg tttggtatgg cttcattcag    5700
ctccggttcc caacgatcaa ggcgagttac atgatccccc atgttgtgca aaaaagcggt    5760
tagctccttc ggtcctccga tcgttgtcag aagtaagttg gccgcagtgt tatcactcat    5820
ggttatggca gcactgcata attctcttac tgtcatgcca tccgtaagat gcttttctgt    5880
gactggtgag tactcaacca agtcattctg agaatagtgt atgcggcgac cgagttgctc    5940
ttgcccggcg tcaatacggg ataataccgc gccacatagc agaactttaa aagtgctcat    6000
cattggaaaa cgttcttcgg ggcgaaaact ctcaaggatc ttaccgctgt tgagatccag    6060
ttcgatgtaa cccactcgtg cacccaactg atcttcagca tcttttactt tcaccagcgt    6120
ttctgggtga gcaaaaacag gaaggcaaaa tgccgcaaaa aagggaataa gggcgacacg    6180
gaaatgttga atactcatac tcttcctttt tcaatattat tgaagcattt atcagggtta    6240
ttgtctcatg agcggataca tatttgaatg tatttagaaa aataaacaaa tagggggttcc    6300 gcgcacattt ccccgaaaag tgccacctg                                      6329

<210> SEQ ID NO 50
<211> LENGTH: 25
<212> TYPE: DNA
<213> ORGANISM: artificial sequence
<220> FEATURE:
<223> OTHER INFORMATION: Primer

<400> SEQUENCE: 50
aacaatatgt aagatctcaa ctatc                                          25

<210> SEQ ID NO 51
<211> LENGTH: 25
<212> TYPE: DNA
<213> ORGANISM: artificial sequence
<220> FEATURE:
<223> OTHER INFORMATION: Primer

<400> SEQUENCE: 51
cagacatgag agatccagtg tgtag                                          25

<210> SEQ ID NO 52
<211> LENGTH: 9332
<212> TYPE: DNA
<213> ORGANISM: artificial sequence
<220> FEATURE:
<223> OTHER INFORMATION: Plasmid pCP20

<400> SEQUENCE: 52
gagacacaac gtggctttgt tgaataaatc gaacttttgc tgagttgaag gatcagatca    60
cgcatcttcc cgacaacgca gaccgttccg tggcaaagca aaagttcaaa atcaccaact    120
ggtccaccta caacaaagct ctcatcaacc gtggctccct cactttctgg ctggatgatg    180
gggcgattca ggcctggtat gagtcagcaa caccttcttc acgaggcaga cctcagcgcc    240
acaggtgcgg ttgctggcgc taaccgtttt tatcaggctc tgggaggcag aataaatgat    300
catatcgtca attattacct ccacggggag agcctgagca aactggcctc aggcatttga    360
gaagcacacg gtcacactgc ttccggtagt caataaaccg gtaaaccagc aatagacata    420
agcggctatt taacgaccct gccctgaacc gacgaccggg tcgaatttgc tttcgaattt    480
ctgccattca tccgcttatt atcacttatt caggcgtagc aaccaggcgt ttaagggcac    540
caataactgc cttaaaaaaa ttacgccccg ccctgccact catcgcagta ctgttgtaat    600
tcattaagca ttctgccgac atggaagcca tcacaaacgg catgatgaac ctgaatcgcc    660
```

```
agcggcatca gcaccttgtc gccttgcgta taatatttgc ccatggtgaa aacgggggcg      720
aagaagttgt ccatattggc cacgtttaaa tcaaaactgg tgaaactcac ccagggattg      780
gctgagacga aaaacatatt ctcaataaac cctttaggga aataggccag gttttcaccg      840
taacacgcca catcttgcga atatatgtgt agaaactgcc ggaaatcgtc gtggtattca      900
ctccagagcg atgaaaacgt ttcagtttgc tcatggaaaa cggtgtaaca agggtgaaca      960
ctatcccata tcaccagctc accgtctttc attgccatac ggaattccgg atgagcattc     1020
atcaggcggg caagaatgtg aataaaggcc ggataaaact tgtgcttatt tttctttacg     1080
gtctttaaaa aggccgtaat atccagctga acggtctggt tataggtaca ttgagcaact     1140
gactgaaatg cctcaaaatg ttctttacga tgccattggg atatatcaac ggtggtatat     1200
ccagtgattt ttttctccat tttagcttcc ttagctcctg aaaatctcga taactcaaaa     1260
aatacgcccg gtagtgatct tatttcatta tggtgaaagt tggaacctct tacgtgccga     1320
tcaacgtctc attttcgcca aaagttggcc cagggcttcc cggtatcaac agggacacca     1380
ggatttattt attctgcgaa gtgatcttcc gtcacaggta tttattcggc gcaaagtgcg     1440
tcgggtgatg ctgccaactt actgatttag tgtatgatgg tgttttttgag gtgctccagt     1500 ggcttctgtt tctatcagct gtccctcctg ttcagctact gacggggtgg tgcgtaacgg     1560
caaaagcacc gccggacatc agcgcttgtt tcggcgtggg tatggtggca ggcccgtgg      1620 ccggggact gttgggcgcc tgtagtgcca tttaccccca ttcactgcca gagccgtgag     1680
cgcagcgaac tgaatgtcac gaaaaagaca gcgactcagg tgcctgatgg tcggagacaa     1740
aaggaatatt cagcgatttg cccgagcttg cgagggtgct acttaagcct ttagggtttt     1800
aaggtctgtt ttgtagagga gcaaacagcg tttgcgacat cctttttgtaa tactgcggaa     1860 ctgactaaag tagtgagtta tacacagggc tgggatctat tcttttttatc ttttttttatt     1920 ctttctttat tctataaatt ataaccactt gaatataaac aaaaaaaaca cacaaaggtc     1980
tagcggaatt tacagagggt ctagcagaat ttacaagttt tccagcaaag gtctagcaga     2040
atttacagat acccacaact caaaggaaaa ggactagtaa ttatcattga ctagcccatc     2100
tcaattggta tagtgattaa aatcacctag accaattgag atgtatgtct gaattagttg     2160
ttttcaaagc aaatgaacta gcgattagtc gctatgactt aacggagcat gaaaccaagc     2220
taattttatg ctgtgtggca ctactcaacc ccacgattga aaaccctaca aggaaagaac     2280
ggacggtatc gttcacttat aaccaatacg ttcagatgat gaacatcagt agggaaaatg     2340
cttatggtgt attagctaaa gcaaccagag agctgatgac gagaactgtg gaaatcagga     2400
atcctttggt taaaggcttt gagattttcc agtggacaaa ctatgccaag ttctcaagcg     2460
aaaaattaga attagttttt agtgaagaga tattgcctta tcttttccag ttaaaaaaat     2520
tcataaaata taatctggaa catgttaagt cttttgaaaa caaatactct atgaggattt     2580
atgagtggtt attaaaagaa ctaacacaaa agaaaactca caaggcaaat atagagatta     2640
gccttgatga atttaagttc atgttaatgc ttgaaaataa ctaccatgag tttaaaggc      2700 ttaaccaatg ggttttgaaa ccaataagta aagatttaaa cacttacagc aatatgaaat     2760
tggtggttga taagcgaggc cgcccgactg atacgttgat tttccaagtt gaactagata     2820
gacaaatgga tctcgtaacc gaacttgaga caaccagat aaaatgaat ggtgacaaaa       2880 taccaacaac cattacatca gattcctacc tacataacgg actaagaaaa acactacacg     2940
atgctttaac tgcaaaaatt cagctcacca gttttgaggc aaaattttg agtgacatgc      3000 aaagtaagta tgatctcaat ggttcgttct catggctcac gcaaaaacaa cgaaccacac     3060
```

```
tagagaacat actggctaaa tacggaagga tctgaggttc ttatggctct tgtatctatc    3120
agtgaagcat caagactaac aaacaaaagt agaacaactg ttcaccgtta catatcaaag    3180
ggaaaactgt ccatatgcac agatgaaaac ggtgtaaaaa agatagatac atcagagctt    3240
ttacgagttt ttggtgcatt taaagctgtt caccatgaac agatcgacaa tgtaacagat    3300
gaacagcatg taacacctaa tagaacaggt gaaaccagta aaacaaagca actagaacat    3360
gaaattgaac acctgagaca acttgttaca gctcaacagt cacacataga cagcctgaaa    3420
caggcgatgc tgcttatcga atcaaagctg ccgacaacac gggagccagt gacgcctccc    3480
gtggggaaaa aatcatggca attctggaag aaatagcgcc tgtttcgttt caggcaggtt    3540
atcagggagt gtcagcgtcc tgcggttctc cggggcgttc gggtcatgca gcccgtaatg    3600
gtgatttacc agcgtctgcc aggcatcaat tctaggcctg tctgcgcggt cgtagtacgg    3660
ctggaggcgt tttccggtct gtagctccat gttcggaatg acaaaattca gctcaagccg    3720
tcccttgtcc tggtgctcca cccacaggat gctgtactga ttttttttcga gacccgggcat    3780 cagtacacgc tcaaagctcg ccatcacttt ttcacgtcct cccggcggca gctccttctc    3840
cgcgaacgac agaacaccgg acgtgtattt cttcgcaaat ggcgtggcat cgatgagttc    3900
ccggacttct tccggattac cctgaagcac cgttgcgcct tcgcggttac gctccctccc    3960
cagcaggtaa tcaaccggac cactgccacc accttttccc ctggcatgaa atttaactat    4020
catcccgcgc ccctgttcc ctgacagcca gacgcagccg gcgcagctca tccccgatgg    4080
ccatcagtgc ggccaccacc tgaacccggt caccggaaga ccactgcccg ctgttcacct    4140
tacgggctgt ctgattcagg ttatttccga tggcggccag ctgacgcagt aacggcggtg    4200
ccagtgtcgg cagttttccg gaacgggcaa ccggctcccc caggcagacc cgccgcatcc    4260
ataccgccag ttgtttaccc tcacagcgtt caagtaaccg ggcatgttca tcatcagtaa    4320
cccgtattgt gagcatcctc tcgcgtttca tcggtatcat tacccccatga acagaaatcc    4380 cccttacacg gaggcatcag tgactaaacg gggtctgacg ctcagtggaa cgaaaactca    4440
cgttaaggga ttttggtcat gagattatca aaaaggatct tcacctagat cctttttaaat    4500 taaaaatgaa gttttaaatc aatctaaagt atatatgagt aaacttggtc tgacagttac    4560
caatgcttaa tcagtgaggc acctatctca gcgatctgtc tatttcgttc atccatagtt    4620
gcctgactcc ccgtcgtgta gataactacg atacgggagg gcttaccatc tggccccagt    4680
gctgcaatga taccgcgaga cccacgctca ccggctccag atttatcagc aataaaccag    4740
ccagccggaa gggccgagcg cagaagtggt cctgcaactt tatccgcctc catccagtct    4800
attaattgtt gccgggaagc tagagtaagt agttcgccag ttaatagttt gcgcaacgtt    4860
gttgccattg ctgcaggcat cgtggtgtca cgctcgtcgt ttggtatggc ttcattcagc    4920
tccggttccc aacgatcaag gcgagttaca tgatccccca tgttgtgcaa aaaagcggtt    4980
agctccttcg gtcctccgat cgttgtcaga agtaagttgg ccgcagtgtt atcactcatg    5040
gttatggcag cactgcataa ttctcttact gtcatgccat ccgtaagatg cttttctgtg    5100
actggtgagt actcaaccaa gtcattctga gaatagtgta tgcggcgacc gagttgctct    5160
tgcccggcgt caacacggga taataccgcg ccacatagca gaactttaaa agtgctcatc    5220
attggaaaac gttcttcggg gcgaaaactc tcaaggatct taccgctgtt gagatccagt    5280
tcgatgtaac ccactcgtgc acccaactga tcttcagcat cttttacttt caccagcgtt    5340
tctgggtgag caaaaacagg aaggcaaaat gccgcaaaaa agggaataag gcgacacgg    5400 aaatgttgaa tactcatact cttcctttt caatattatt gaagcattta tcagggttat    5460
```

```
tgtctcatga gcggatacat atttgaatgt atttagaaaa ataaacaaat aggggttccg   5520
cgcacatttc cccgaaaagt gccacctgac gtctaagaaa ccattattat catgacatta   5580
acctataaaa ataggcgtat cacgaggccc tttcgtcttc aagaatttta taaaccgtgg   5640
agcgggcaat actgagctga tgagcaattt ccgttgcacc agtgcccttc tgatgaagcg   5700
tcagcacgac gttcctgtcc acggtacgcc tgcggccaaa tttgattcct ttcagctttg   5760
cttcctgtcg gccctcattc gtgcgctcta ggatcctcta cgccggacgc atcgtggccg   5820
gcatcaccgg cgctgaggtc tgcctcgtga agaaggtgtt gctgactcat accaggcctg   5880
aatcgcccca tcatccagcc agaaagtgag ggagccacgg ttgatgagag ctttgttgta   5940
ggtggaccag ttggtgattt tgaacttttg ctttgccacg gaacggtctg cgttgtcggg   6000
aagatgcgtg atctgatcct tcaactcagc aaaagttcga tttattcaac aaagccgccg   6060
tcccgtcaag tcagcgtaat gctctgccag tgttacaacc aattaaccaa ttctgattag   6120
aaaaactcat cgagcatcaa atgaaactgc aatttattca tatcaggatt atcaatacca   6180 tattttgaa aaagccgttt ctgtaatgaa ggagaaaact caccgaggca gttccatagg   6240
atggcaagat cctggtatcg gtctgcgatt ccgactcgtc caacatcaat acaacctatt   6300
aatttcccct cgtcaaaaat aaggttatca agtgagaaat caccatgagt gacgactgaa   6360
tccggtgaga atggcagaat aggaacttcg gaataggaac ttcaaagcgt ttccgaaaac   6420
gagcgcttcc gaaaatgcaa cgcgagctgc gcacatacag ctcactgttc acgtcgcacc   6480
tatatctgcg tgttgcctgt atatatatat acatgagaag aacggcatag tgcgtgttta   6540
tgcttaaatg cgtacttata tgcgtctatt tatgtaggat gaaaggtagt ctagtacctc   6600
ctgtgatatt atcccattcc atgcggggta tcgtatgctt ccttcagcac tacccttttag  6660 ctgttctata tgctgccact cctcaattgg attagtctca tccttcaatg ctatcatttc   6720
ctttgatatt ggatcatatg catagtaccg agaaactagt gcgaagtagt gatcaggtat   6780
tgctgttatc tgatgagtat acgttgtcct ggccacggca gaagcacgct tatcgctcca   6840
atttcccaca acattagtca actccgttag gcccttcatt gaaagaaatg aggtcatcaa   6900
atgtcttcca atgtgagatt tgggccatt ttttatagca aagattgaat aaggcgcatt   6960
tttcttcaaa gctttattgt acgatctgac taagttatct tttaataatt ggtattcctg   7020
tttattgctt gaagaattgc cggtcctatt tactcgtttt aggactggtt cagaattcct   7080
caaaaattca tccaaatata caagtggatc gatcctaccc cttgcgctaa agaagtatat   7140
gtgcctacta acgcttgtct ttgtctctgt cactaaacac tggattatta ctcccagata   7200 cttatttgg actaatttaa atgatttcgg atcaacgttc ttaatatcgc tgaatcttcc   7260
acaattgatg aaagtagcta ggaagaggaa ttggtataaa gttttgttt ttgtaaatct   7320 cgaagtatac tcaaacgaat ttagtatttt ctcagtgatc tcccagatgc tttcaccctc   7380
acttagaagt gctttaagca ttttttact gtggctattt cccttatctg cttcttccga   7440
tgattcgaac tgtaattgca aactacttac aatatcagtg atatcagatt gatgtttttg   7500
tccatagtaa ggaataattg taaattccca agcaggaatc aatttcttta atgaggcttc   7560
cagaattgtt gcttttgcg tcttgtattt aaactggagt gatttattga caatatcgaa   7620
actcagcgaa ttgcttatga tagtattata gctcatgaat gtggctctct tgattgctgt   7680
tccgttatgt gtaatcatcc aacataaata ggttagttca gcagcacata atgctatttt   7740
ctcacctgaa ggtctttcaa accttccac aaactgacga acaagcacct taggtggtgt   7800
tttacataat atatcaaatt gtggcataca acctccttag tacatgcaac cattatcacc   7860
```

-continued

```
gccagaggta aaatagtcaa cacgcacggt gttagatatt tatcccttgc ggtgatagat    7920
ttaacgtatg agcacaaaaa agaaaccatt aacacaagag cagcttgagg acgcacgtcg    7980
ccttaaagca atttatgaaa aaagaaaaa tgaacttggc ttatcccagg aatctgtcgc     8040
agacaagatg gggatggggc agtcaggcgt tggtgcttta tttaatggca tcaatgcatt    8100
aaatgcttat aacgccgcat tgcttacaaa aattctcaaa gttagcgttg aagaatttag    8160
cccttcaatc gccagagaaa tctacgagat gtatgaagcg gttagtatgc agccgtcact    8220
tagaagtgag tatgagtacc ctgttttttc tcatgttcag gcagggatgt tctcacctaa    8280
gcttagaacc tttaccaaag gtgatgcgga gagatgggta agcacaacca aaaaagccag    8340
tgattctgca ttctggcttg aggttgaagg taattccatg accgcaccaa caggctccaa    8400
gccaagcttt cctgacggaa tgttaattct cgttgaccct gagcaggctg ttgagccagg    8460
tgatttctgc atagccagac ttgggggtga tgagtttacc ttcaagaaac tgatcaggga    8520
tagcggtcag gtgtttttac aaccactaaa cccacagtac ccaatgatcc catgcaatga    8580
gagttgttcc gttgtgggga aagttatcgc tagtcagtgg cctgaagaga cgtttggctg    8640
atcggcaagg tgttctggtc ggcgcatagc tgataacaat tgagcaagaa tctgcatttc    8700
tttccagact tgttcaacag gccagccatt acgctcgtca tcaaaatcac tcgcatcaac    8760
caaaccgtta ttcattcgtg attgcgcctg agcgagacga aatacgcgat cgctgttaaa    8820
aggacaatta caaacaggaa tcgaatgcaa ccggcgcagg aacactgcca gcgcatcaac    8880
aatattttca cctgaatcag gatattcttc taatacctgg aatgctgttt cccgggggat    8940
cgcagtggtg agtaaccatg catcatcagg agtacggata aaatgcttga tggtcggaag    9000
aggcataaat tccgtcagcc agtttagtct gaccatctca tctgtaacat cattggcaac    9060
gctacctttg ccatgtttca gaaacaactc tggcgcatcg ggcttcccat acaatcgata    9120
gattgtcgca cctgattgcc cgacattatc gcgagcccat ttatacccat ataaatcagc    9180
atccatgttg gaatttaatc gcggcctcga gcaagacgtt tcccgttgaa tatggctcat    9240
aacacccctt gtattactgt ttatgtaagc agacagtttt attgttcatg atgatatatt    9300
tttatcttgt gcaatgtaac atcagagatt tt                                  9332
```

<210> SEQ ID NO 53
<211> LENGTH: 80
<212> TYPE: DNA
<213> ORGANISM: artificial sequence
<220> FEATURE:
<223> OTHER INFORMATION: Primer

<400> SEQUENCE: 53

```
atgtcgcaac ataacgaaaa gaacccacat cagcaccagt caccactaca cgattccagc    60
gtgtaggctg gagctgcttc                                                80
```

<210> SEQ ID NO 54
<211> LENGTH: 82
<212> TYPE: DNA
<213> ORGANISM: artificial sequence
<220> FEATURE:
<223> OTHER INFORMATION: Primer

<400> SEQUENCE: 54

```
ttacgccggg attttgtcaa tcttaggaat gcgtgaccac acgcggtgtg ctgtcatcag    60
attccgggga tccgtcgacc tg                                             82
```

<210> SEQ ID NO 55
<211> LENGTH: 1424
<212> TYPE: DNA
<213> ORGANISM: artificial sequence
<220> FEATURE:
<223> OTHER INFORMATION: Synthetic construct

<400> SEQUENCE: 55

```
ttacgccggg attttgtcaa tcttaggaat gcgtgaccac acgcggtgtg ctgtcatcag      60
attccggggga tccgtcgacc tgcagttcga agttcctatt ctctagaaag tataggaact    120
tcagagcgct tttgaagctc acgctgccgc aagcactcag ggcgcaaggg ctgctaaagg     180
aagcggaaca cgtagaaagc cagtccgcag aaacggtgct gaccccggat gaatgtcagc     240
tactgggcta tctggacaag ggaaaacgca agcgcaaaga gaaagcaggt agcttgcagt     300
gggcttacat ggcgatagct agactgggcg gttttatgga cagcaagcga accggaattg     360
ccagctgggg cgccctctgg taaggttggg aagccctgca agtaaactg gatggctttc      420
ttgccgccaa ggatctgatg gcgcagggga tcaagatctg atcaagagac aggatgagga     480
tcgtttcgca tgattgaaca agatggattg cacgcaggtt ctccggccgc ttgggtggag     540
aggctattcg gctatgactg gcacaacaga caatcggct gctctgatgc cgccgtgttc      600
cggctgtcag cgcaggggcg cccggttctt tttgtcaaga ccgacctgtc cggtgccctg    660
aatgaactgc aggacgaggc agcgcggcta tcgtggctgg ccacgacggg cgttccttgc    720
gcagctgtgc tcgacgttgt cactgaagcg ggaagggact ggctgctatt gggcgaagtg    780
ccggggcagg atctcctgtc atctcacctt gctcctgccg agaaagtatc catcatggct    840
gatgcaatgc ggcggctgca tacgcttgat ccggctacct gcccattcga ccaccaagcg    900
aaacatcgca tcgagcgagc acgtactcgg atggaagccg gtcttgtcga tcaggatgat    960
ctggacgaag agcatcaggg gctcgcgcca gccgaactgt tcgccaggct caaggcgcgc   1020
atgcccgacg gcgaggatct cgtcgtgacc catggcgatg cctgcttgcc gaatatcatg   1080
gtggaaaatg gccgcttttc tggattcatc gactgtggcc ggctgggtgt ggcggaccgc   1140
tatcaggaca tagcgttggc tacccgtgat attgctgaag agcttggcgg cgaatgggct   1200
gaccgcttcc tcgtgcttta cggtatcgcc gctcccgatt cgcagcgcat cgccttctat   1260
cgccttcttg acgagttctt ctaataaggg gatcttgaag ttcctattcc gaagttccta   1320
ttctctagaa agtataggaa cttcgaagca gctccagcct acacgctgga atcgtgtagt   1380
ggtgactggt gctgatgtgg gttcttttcg ttatgttgcg acat                    1424
```

<210> SEQ ID NO 56
<211> LENGTH: 2262
<212> TYPE: DNA
<213> ORGANISM: Escherichia coli
<220> FEATURE:
<221> NAME/KEY: CDS
<222> LOCATION: (1)..(2262)

<400> SEQUENCE: 56

| atg | tcg | caa | cat | aac | gaa | aag | aac | cca | cat | cag | cac | cag | tca | cca | cta | 48 |
|-----|-----|-----|-----|-----|-----|-----|-----|-----|-----|-----|-----|-----|-----|-----|-----|----|
| Met | Ser | Gln | His | Asn | Glu | Lys | Asn | Pro | His | Gln | His | Gln | Ser | Pro | Leu | |
| 1 | | | | 5 | | | | | 10 | | | | | 15 | | |

| cac | gat | tcc | agc | gaa | gcg | aaa | ccg | ggg | atg | gac | tca | ctg | gca | cct | gag | 96 |
|-----|-----|-----|-----|-----|-----|-----|-----|-----|-----|-----|-----|-----|-----|-----|-----|----|
| His | Asp | Ser | Ser | Glu | Ala | Lys | Pro | Gly | Met | Asp | Ser | Leu | Ala | Pro | Glu | |
| | | | 20 | | | | | 25 | | | | | 30 | | | |

| gac | ggc | tct | cat | cgt | cca | gcg | gct | gaa | cca | aca | ccg | cca | ggt | gca | caa | 144 |
|-----|-----|-----|-----|-----|-----|-----|-----|-----|-----|-----|-----|-----|-----|-----|-----|-----|
| Asp | Gly | Ser | His | Arg | Pro | Ala | Ala | Glu | Pro | Thr | Pro | Pro | Gly | Ala | Gln | |
| | | 35 | | | | | 40 | | | | | 45 | | | | |

```
                                                                -continued cct acc gcc cca ggg agc ctg aaa gcc cct gat acg cgt aac gaa aaa           192
Pro Thr Ala Pro Gly Ser Leu Lys Ala Pro Asp Thr Arg Asn Glu Lys
    50              55              60 ctt aat tct ctg gaa gac gta cgc aaa ggc agt gaa aat tat gcg ctg           240
Leu Asn Ser Leu Glu Asp Val Arg Lys Gly Ser Glu Asn Tyr Ala Leu
65              70              75              80 acc act aat cag ggc gtg cgc atc gcc gac gat caa aac tca ctg cgt           288
Thr Thr Asn Gln Gly Val Arg Ile Ala Asp Asp Gln Asn Ser Leu Arg
            85              90              95 gcc ggt agc cgt ggt cca acg ctg ctg gaa gat ttt att ctg cgc gag           336
Ala Gly Ser Arg Gly Pro Thr Leu Leu Glu Asp Phe Ile Leu Arg Glu
        100             105             110 aaa atc acc cac ttt gac cat gag cgc att ccg gaa cgt att gtt cat           384
Lys Ile Thr His Phe Asp His Glu Arg Ile Pro Glu Arg Ile Val His
        115             120             125 gca cgc gga tca gcc gct cac ggt tat ttc cag cca tat aaa agc tta           432
Ala Arg Gly Ser Ala Ala His Gly Tyr Phe Gln Pro Tyr Lys Ser Leu
    130             135             140 agc gat att acc aaa gcg gat ttc ctc tca gat ccg aac aaa atc acc           480
Ser Asp Ile Thr Lys Ala Asp Phe Leu Ser Asp Pro Asn Lys Ile Thr
145             150             155             160 cca gta ttt gta cgt ttc tct acc gtt cag ggt ggt gct ggc tct gct           528
Pro Val Phe Val Arg Phe Ser Thr Val Gln Gly Gly Ala Gly Ser Ala
            165             170             175 gat acc gtg cgt gat atc cgt ggc ttt gcc acc aag ttc tat acc gaa           576
Asp Thr Val Arg Asp Ile Arg Gly Phe Ala Thr Lys Phe Tyr Thr Glu
        180             185             190 gag ggt att ttt gac ctc gtt ggc aat aac acg cca atc ttc ttt atc           624
Glu Gly Ile Phe Asp Leu Val Gly Asn Asn Thr Pro Ile Phe Phe Ile
        195             200             205 cag gat gcg cat aaa ttc ccc gat ttt gtt cat gcg gta aaa cca gaa           672
Gln Asp Ala His Lys Phe Pro Asp Phe Val His Ala Val Lys Pro Glu
    210             215             220 ccg cac tgg gca att cca caa ggg caa agt gcc cac gat act ttc tgg           720
Pro His Trp Ala Ile Pro Gln Gly Gln Ser Ala His Asp Thr Phe Trp
225             230             235             240 gat tat gtt tct ctg caa cct gaa act ctg cac aac gtg atg tgg gcg           768
Asp Tyr Val Ser Leu Gln Pro Glu Thr Leu His Asn Val Met Trp Ala
            245             250             255 atg tcg gat cgc ggc atc ccc cgc agt tac cgc acc atg gaa ggc ttc           816
Met Ser Asp Arg Gly Ile Pro Arg Ser Tyr Arg Thr Met Glu Gly Phe
        260             265             270 ggt att cac acc ttc cgc ctg att aat gcc gaa ggg aag gca acg ttt           864
Gly Ile His Thr Phe Arg Leu Ile Asn Ala Glu Gly Lys Ala Thr Phe
        275             280             285 gta cgt ttc cac tgg aaa cca ctg gca ggt aaa gcc tca ctc gtt tgg           912
Val Arg Phe His Trp Lys Pro Leu Ala Gly Lys Ala Ser Leu Val Trp
    290             295             300 gat gaa gca caa aaa ctc acc gga cgt gac ccg gac ttc cac cgc cgc           960
Asp Glu Ala Gln Lys Leu Thr Gly Arg Asp Pro Asp Phe His Arg Arg
305             310             315             320 gag ttg tgg gaa gcc att gaa gca ggc gat ttt ccg gaa tac gaa ctg          1008
Glu Leu Trp Glu Ala Ile Glu Ala Gly Asp Phe Pro Glu Tyr Glu Leu
            325             330             335 ggc ttc cag ttg att cct gaa gaa gat gaa ttc aag ttc gac ttc gat          1056
Gly Phe Gln Leu Ile Pro Glu Glu Asp Glu Phe Lys Phe Asp Phe Asp
        340             345             350 ctt ctc gat cca acc aaa ctt atc ccg gaa gaa ctg gtg ccc gtt cag          1104
Leu Leu Asp Pro Thr Lys Leu Ile Pro Glu Glu Leu Val Pro Val Gln
        355             360             365
```

```
cgt gtc ggc aaa atg gtg ctc aat cgc aac ccg gat aac ttc ttt gct     1152
Arg Val Gly Lys Met Val Leu Asn Arg Asn Pro Asp Asn Phe Phe Ala
    370             375             380 gaa aac gaa cag gcg gct ttc cat cct ggg cat atc gtg ccg gga ctg     1200
Glu Asn Glu Gln Ala Ala Phe His Pro Gly His Ile Val Pro Gly Leu
385             390             395             400 gac ttc acc aac gat ccg ctg ttg cag gga cgt ttg ttc tcc tat acc     1248
Asp Phe Thr Asn Asp Pro Leu Leu Gln Gly Arg Leu Phe Ser Tyr Thr
            405             410             415 gat aca caa atc agt cgt ctt ggt ggg ccg aat ttc cat gag att ccg     1296
Asp Thr Gln Ile Ser Arg Leu Gly Gly Pro Asn Phe His Glu Ile Pro
        420             425             430 att aac cgt ccg acc tgc cct tac cat aat ttc cag cgt gac ggc atg     1344
Ile Asn Arg Pro Thr Cys Pro Tyr His Asn Phe Gln Arg Asp Gly Met
    435             440             445 cat cgc atg ggg atc gac act aac ccg gcg aat tac gaa ccg aac tcg     1392
His Arg Met Gly Ile Asp Thr Asn Pro Ala Asn Tyr Glu Pro Asn Ser
    450             455             460 att aac gat aac tgg ccg cgc gaa aca ccg ccg ggg ccg aaa cgc ggc     1440
Ile Asn Asp Asn Trp Pro Arg Glu Thr Pro Pro Gly Pro Lys Arg Gly
465             470             475             480 ggt ttt gaa tca tac cag gag cgc gtg gaa ggc aat aaa gtt cgc gag     1488
Gly Phe Glu Ser Tyr Gln Glu Arg Val Glu Gly Asn Lys Val Arg Glu
            485             490             495 cgc agc cca tcg ttt ggc gaa tat tat tcc cat ccg cgt ctg ttc tgg     1536
Arg Ser Pro Ser Phe Gly Glu Tyr Tyr Ser His Pro Arg Leu Phe Trp
        500             505             510 cta agt cag acg cca ttt gag cag cgc cat att gtc gat ggt ttc agt     1584
Leu Ser Gln Thr Pro Phe Glu Gln Arg His Ile Val Asp Gly Phe Ser
    515             520             525 ttt gag tta agc aaa gtc gtt cgt ccg tat att cgt gag cgc gtt gtt     1632
Phe Glu Leu Ser Lys Val Val Arg Pro Tyr Ile Arg Glu Arg Val Val
530             535             540 gac cag ctg gcg cat att gat ctc act ctg gcc cag gcg gtg gcg aaa     1680
Asp Gln Leu Ala His Ile Asp Leu Thr Leu Ala Gln Ala Val Ala Lys
545             550             555             560 aat ctc ggt atc gaa ctg act gac gac cag ctg aat atc acc cca cct     1728
Asn Leu Gly Ile Glu Leu Thr Asp Asp Gln Leu Asn Ile Thr Pro Pro
            565             570             575 ccg gac gtc aac ggt ctg aaa aag gat cca tcc tta agt ttg tac gcc     1776
Pro Asp Val Asn Gly Leu Lys Lys Asp Pro Ser Leu Ser Leu Tyr Ala
        580             585             590 att cct gac ggt gat gtg aaa ggt cgc gtg gta gcg att tta ctt aat     1824
Ile Pro Asp Gly Asp Val Lys Gly Arg Val Val Ala Ile Leu Leu Asn
    595             600             605 gat gaa gtg aga tcg gca gac ctt ctg gcc att ctc aag gcg ctg aag     1872
Asp Glu Val Arg Ser Ala Asp Leu Leu Ala Ile Leu Lys Ala Leu Lys
610             615             620 gcc aaa ggc gtt cat gcc aaa ctg ctc tac tcc cga atg ggt gaa gtg     1920
Ala Lys Gly Val His Ala Lys Leu Leu Tyr Ser Arg Met Gly Glu Val
625             630             635             640 act gcg gat gac ggt acg gtg ttg cct ata gcc gct acc ttt gcc ggt     1968
Thr Ala Asp Asp Gly Thr Val Leu Pro Ile Ala Ala Thr Phe Ala Gly
            645             650             655 gca cct tcg ctg acg gtc gat gcg gtc att gtc cct tgc ggc aat atc     2016
Ala Pro Ser Leu Thr Val Asp Ala Val Ile Val Pro Cys Gly Asn Ile
        660             665             670 gcg gat atc gct gac aac ggc gat gcc aac tac tac ctg atg gaa gcc     2064
Ala Asp Ile Ala Asp Asn Gly Asp Ala Asn Tyr Tyr Leu Met Glu Ala
    675             680             685
```

-continued

| | | | | | | | | | | | | | | | | |
|---|---|---|---|---|---|---|---|---|---|---|---|---|---|---|---|---|
| tac | aaa | cac | ctt | aaa | ccg | att | gcg | ctg | gcg | ggt | gac | gcg | cgc | aag | ttt | 2112 |
| Tyr | Lys | His | Leu | Lys | Pro | Ile | Ala | Leu | Ala | Gly | Asp | Ala | Arg | Lys | Phe | |
| | 690 | | | | 695 | | | | 700 | | | | | | | |
| aaa | gca | aca | atc | aag | atc | gct | gac | cag | ggt | gaa | gaa | ggg | att | gtg | gaa | 2160 |
| Lys | Ala | Thr | Ile | Lys | Ile | Ala | Asp | Gln | Gly | Glu | Glu | Gly | Ile | Val | Glu | |
| 705 | | | | 710 | | | | | 715 | | | | | | 720 | |
| gct | gac | agc | gct | gac | ggt | agt | ttt | atg | gat | gaa | ctg | cta | acg | ctg | atg | 2208 |
| Ala | Asp | Ser | Ala | Asp | Gly | Ser | Phe | Met | Asp | Glu | Leu | Leu | Thr | Leu | Met | |
| | | | | 725 | | | | | 730 | | | | | 735 | | |
| gca | gca | cac | cgc | gtg | tgg | tca | cgc | att | cct | aag | att | gac | aaa | att | cct | 2256 |
| Ala | Ala | His | Arg | Val | Trp | Ser | Arg | Ile | Pro | Lys | Ile | Asp | Lys | Ile | Pro | |
| | | | 740 | | | | | 745 | | | | | 750 | | | |
| gcc | tga | | | | | | | | | | | | | | | 2262 |
| Ala | | | | | | | | | | | | | | | | |

<210> SEQ ID NO 57
<211> LENGTH: 753
<212> TYPE: PRT
<213> ORGANISM: Escherichia coli

<400> SEQUENCE: 57

Met Ser Gln His Asn Glu Lys Asn Pro His Gln His Gln Ser Pro Leu
1               5                   10                  15

His Asp Ser Ser Glu Ala Lys Pro Gly Met Asp Ser Leu Ala Pro Glu
            20                  25                  30

Asp Gly Ser His Arg Pro Ala Ala Glu Pro Thr Pro Pro Gly Ala Gln
        35                  40                  45

Pro Thr Ala Pro Gly Ser Leu Lys Ala Pro Asp Thr Arg Asn Glu Lys
    50                  55                  60

Leu Asn Ser Leu Glu Asp Val Arg Lys Gly Ser Glu Asn Tyr Ala Leu
65                  70                  75                  80

Thr Thr Asn Gln Gly Val Arg Ile Ala Asp Asp Gln Asn Ser Leu Arg
                85                  90                  95

Ala Gly Ser Arg Gly Pro Thr Leu Leu Glu Asp Phe Ile Leu Arg Glu
            100                 105                 110

Lys Ile Thr His Phe Asp His Glu Arg Ile Pro Glu Arg Ile Val His
        115                 120                 125

Ala Arg Gly Ser Ala Ala His Gly Tyr Phe Gln Pro Tyr Lys Ser Leu
    130                 135                 140

Ser Asp Ile Thr Lys Ala Asp Phe Leu Ser Asp Pro Asn Lys Ile Thr
145                 150                 155                 160

Pro Val Phe Val Arg Phe Ser Thr Val Gln Gly Ala Gly Ser Ala
                165                 170                 175

Asp Thr Val Arg Asp Ile Arg Gly Phe Ala Thr Lys Phe Tyr Thr Glu
            180                 185                 190

Glu Gly Ile Phe Asp Leu Val Gly Asn Asn Thr Pro Ile Phe Phe Ile
        195                 200                 205

Gln Asp Ala His Lys Phe Pro Asp Phe Val His Ala Val Lys Pro Glu
    210                 215                 220

Pro His Trp Ala Ile Pro Gln Gly Gln Ser Ala His Asp Thr Phe Trp
225                 230                 235                 240

Asp Tyr Val Ser Leu Gln Pro Glu Thr Leu His Asn Val Met Trp Ala
                245                 250                 255

Met Ser Asp Arg Gly Ile Pro Arg Ser Tyr Arg Thr Met Glu Gly Phe
            260                 265                 270

Gly Ile His Thr Phe Arg Leu Ile Asn Ala Glu Gly Lys Ala Thr Phe
        275                 280                 285

```
Val Arg Phe His Trp Lys Pro Leu Ala Gly Lys Ala Ser Leu Val Trp
    290                 295                 300
Asp Glu Ala Gln Lys Leu Thr Gly Arg Asp Pro Asp Phe His Arg Arg
305                 310                 315                 320
Glu Leu Trp Glu Ala Ile Glu Ala Gly Asp Phe Pro Glu Tyr Glu Leu
                325                 330                 335
Gly Phe Gln Leu Ile Pro Glu Glu Asp Glu Phe Lys Phe Asp Phe Asp
                340                 345                 350
Leu Leu Asp Pro Thr Lys Leu Ile Pro Glu Glu Leu Val Pro Val Gln
            355                 360                 365
Arg Val Gly Lys Met Val Leu Asn Arg Asn Pro Asp Asn Phe Phe Ala
370                 375                 380
Glu Asn Glu Gln Ala Ala Phe His Pro Gly His Ile Val Pro Gly Leu
385                 390                 395                 400
Asp Phe Thr Asn Asp Pro Leu Leu Gln Gly Arg Leu Phe Ser Tyr Thr
                405                 410                 415
Asp Thr Gln Ile Ser Arg Leu Gly Gly Pro Asn Phe His Glu Ile Pro
                420                 425                 430
Ile Asn Arg Pro Thr Cys Pro Tyr His Asn Phe Gln Arg Asp Gly Met
            435                 440                 445
His Arg Met Gly Ile Asp Thr Asn Pro Ala Asn Tyr Glu Pro Asn Ser
450                 455                 460
Ile Asn Asp Asn Trp Pro Arg Glu Thr Pro Pro Gly Pro Lys Arg Gly
465                 470                 475                 480
Gly Phe Glu Ser Tyr Gln Glu Arg Val Glu Gly Asn Lys Val Arg Glu
                485                 490                 495
Arg Ser Pro Ser Phe Gly Glu Tyr Tyr Ser His Pro Arg Leu Phe Trp
            500                 505                 510
Leu Ser Gln Thr Pro Phe Glu Gln Arg His Ile Val Asp Gly Phe Ser
            515                 520                 525
Phe Glu Leu Ser Lys Val Val Arg Pro Tyr Ile Arg Glu Arg Val Val
    530                 535                 540
Asp Gln Leu Ala His Ile Asp Leu Thr Leu Ala Gln Ala Val Ala Lys
545                 550                 555                 560
Asn Leu Gly Ile Glu Leu Thr Asp Asp Gln Leu Asn Ile Thr Pro Pro
                565                 570                 575
Pro Asp Val Asn Gly Leu Lys Lys Asp Pro Ser Leu Ser Leu Tyr Ala
            580                 585                 590
Ile Pro Asp Gly Asp Val Lys Gly Arg Val Val Ala Ile Leu Leu Asn
        595                 600                 605
Asp Glu Val Arg Ser Ala Asp Leu Leu Ala Ile Leu Lys Ala Leu Lys
    610                 615                 620
Ala Lys Gly Val His Ala Lys Leu Leu Tyr Ser Arg Met Gly Glu Val
625                 630                 635                 640
Thr Ala Asp Asp Gly Thr Val Leu Pro Ile Ala Ala Thr Phe Ala Gly
                645                 650                 655
Ala Pro Ser Leu Thr Val Asp Ala Val Ile Val Pro Cys Gly Asn Ile
            660                 665                 670
Ala Asp Ile Ala Asp Asn Gly Asp Ala Asn Tyr Tyr Leu Met Glu Ala
        675                 680                 685
Tyr Lys His Leu Lys Pro Ile Ala Leu Ala Gly Asp Ala Arg Lys Phe
    690                 695                 700
Lys Ala Thr Ile Lys Ile Ala Asp Gln Gly Glu Glu Gly Ile Val Glu
```

```
                    705                 710                 715                 720
Ala Asp Ser Ala Asp Gly Ser Phe Met Asp Glu Leu Leu Thr Leu Met
                725                 730                 735

Ala Ala His Arg Val Trp Ser Arg Ile Pro Lys Ile Asp Lys Ile Pro
            740                 745                 750

Ala

<210> SEQ ID NO 58
<211> LENGTH: 25
<212> TYPE: DNA
<213> ORGANISM: artificial sequence
<220> FEATURE:
<223> OTHER INFORMATION: Primer

<400> SEQUENCE: 58
gatctgactg gtggtctata gttag                                              25

<210> SEQ ID NO 59
<211> LENGTH: 25
<212> TYPE: DNA
<213> ORGANISM: artificial sequence
<220> FEATURE:
<223> OTHER INFORMATION: Primer

<400> SEQUENCE: 59
gtagttatca tgatgtgtaa gtaag                                              25

<210> SEQ ID NO 60
<211> LENGTH: 963
<212> TYPE: DNA
<213> ORGANISM: artificial sequence
<220> FEATURE:
<223> OTHER INFORMATION: Synthetic construct

<400> SEQUENCE: 60
atgcagctgt ttgacctgag cctggaagaa ctgaaaaagt ataaaccgaa aaagaccgcc         60
cgtcctgact tctctgattt ctggaagaaa tctctggaag aactgcgtca ggtagaagct        120
gaaccgaccc tggaaagcta cgactatcca gtaaaggggc gtgaaagtgta ccgtctgact       180 taccagtctt tcggtcactc taagattgaa ggtttctacg ctgtaccgga ccaaactggt       240
ccgcatccgg cgctggttcg tttccatggc tacaatgctt cttatgatgg cggtattcac       300
gacatcgtca attgggctct gcacggctac gcaactttcg gcatgctggt ccgtggccag       360
ggtggcagcg aagataccag cgtcactcca ggcggccatg cactgggttg gatgaccaaa       420
ggtattctga gcaaagacac ctactactac cgcggcgtct acctggatgc ggtacgtgct       480
ctggaagtca ttcagtcttt cccggaagtc gacgaacacc gtatcggtgt aattggtggc       540
tctcagggtg gcgccctggc catcgcggca gcggcactgt ccgatatccc gaaggtggtg       600
gtggcggatt acccgtacct gtctaacttc gaacgtgcgg ttgacgtggc tctgaacag       660 ccgtacctgg agatcaactc ttacttccgc cgtaacagcg atccgaaagt ggaggagaaa      720
gcgttcgaaa ccctgagcta cttcgatctg atcaacctgg caggctgggt gaaacagccg      780
actctgatgg ctattggtct gatcgataag atcaccccgc catccactgt cttcgcggct      840
tacaaccacc tggaaactga taagatctg aaagtatacc gttacttcgg ccacgagttt      900
atccctgcat ccagaccga gaaactgtct ttcctgcaaa agcacctgct gctgtccacc      960
taa                                                                     963

<210> SEQ ID NO 61
```

```
<211> LENGTH: 182
<212> TYPE: PRT
<213> ORGANISM: Bacillus subtilis ATCC 31954

<400> SEQUENCE: 61

Arg Gly Gln Gln Ser Ser Glu Asp Thr Ser Ile Ser Leu His Gly His
 1               5                  10                  15

Ala Leu Gly Trp Met Thr Lys Gly Ile Leu Asp Lys Asp Thr Tyr Tyr
            20                  25                  30

Tyr Arg Gly Val Tyr Leu Asp Ala Val Arg Ala Leu Glu Val Ile Ser
        35                  40                  45

Ser Phe Asp Glu Val Asp Glu Thr Arg Ile Gly Val Thr Gly Gly Ser
    50                  55                  60

Gln Gly Gly Gly Leu Thr Ile Ala Ala Ala Leu Ser Asp Ile Pro
65                  70                  75                  80

Lys Ala Ala Val Ala Asp Tyr Pro Tyr Leu Ser Asn Phe Glu Arg Ala
                85                  90                  95

Ile Asp Val Ala Leu Glu Gln Pro Tyr Leu Glu Ile Asn Ser Phe Phe
            100                 105                 110

Arg Arg Asn Gly Ser Pro Glu Thr Glu Val Gln Ala Met Lys Thr Leu
        115                 120                 125

Ser Tyr Phe Asp Ile Met Asn Leu Ala Asp Arg Val Lys Val Pro Val
    130                 135                 140

Leu Met Ser Ile Gly Leu Ile Asp Lys Val Thr Pro Pro Ser Thr Val
145                 150                 155                 160

Phe Ala Ala Tyr Asn His Leu Glu Thr Glu Lys Glu Leu Lys Val Tyr
                165                 170                 175

Arg Tyr Phe Gly His Glu
            180

<210> SEQ ID NO 62
<211> LENGTH: 53
<212> TYPE: DNA
<213> ORGANISM: artificial sequence
<220> FEATURE:
<223> OTHER INFORMATION: Primer

<400> SEQUENCE: 62
taactgcagt aaggaggaat aggacatgcc tctggttgat atgcctctgc gtg        53

<210> SEQ ID NO 63
<211> LENGTH: 39
<212> TYPE: DNA
<213> ORGANISM: artificial sequence
<220> FEATURE:
<223> OTHER INFORMATION: Primer

<400> SEQUENCE: 63
tgatctagat taggaggtga agaagcggaa gatctgatc                         39

<210> SEQ ID NO 64
<211> LENGTH: 988
<212> TYPE: DNA
<213> ORGANISM: artificial sequence
<220> FEATURE:
<223> OTHER INFORMATION: PCR amplification product

<400> SEQUENCE: 64
taactgcagt aaggaggaat aggacatgcc tctggttgat atgcctctgc gtgaactgct   60
ggcttatgaa ggcatcaacc caaaacctgc tgacttcgat cagtattgga accgcgctaa  120
```

| | | | |
|---|---|---|---|
| aaccgaaatt gaggctatcg atcctgaagt aactctggta gagtcctcct tccagtgctc | 180 |
| cttcgctaac tgctaccatt tctattatcg ttccgcgggc aacgctaaaa tccacgcgaa | 240 |
| gtacgtacag ccaaaagcgg gtgaaaaaac tccggcagtc ttcatgtttc acggctacgg | 300 |
| tggtcgttcc gctgaatggt cctctctgct gaactacgtt gctgctggtt tcagcgtctt | 360 |
| ctacatggat gttcgtggcc agggcggtac ctccgaggac ccgggtggcg tacgtggtaa | 420 |
| cacctatcgt ggtcatatca tccgtggcct ggacgcgggt ccggatgcgc tgttctaccg | 480 |
| ttccgtgttc ctggacacgg tacagctggt gcgcgctgca aaaaccctgc cgcacattga | 540 |
| caagacccgt ctgatggcca ccggctggag ccagggtggc gcactgactc tggcgtgtgc | 600 |
| agcgctggta ccggaaatca aacgtctggc gccggtctac ccgttcctgt ctgactacaa | 660 |
| acgcgtatgg cagatggacc tggctgttcg ttcctacaaa gaactggcgg actatttccg | 720 |
| ctcctatgat ccgcagcata aacgccacgg tgaaattttc gaacgcctgg ttatatcga | 780 |
| cgttcagcac ctggctgatc gtattcaggg cgacgttctg atgggtgtgg gcctgatgga | 840 |
| caccgaatgc cgccgagca cccaatttgc ggcgtacaac aagattaaag ctaagaaaag | 900 |
| ctacgaactg tacccggact ttggtcatga gcatctgcct ggtatgaacg atcacatctt | 960 |
| ccgcttcttc acctcctaat ctagatca | 988 |

<210> SEQ ID NO 65
<211> LENGTH: 951
<212> TYPE: DNA
<213> ORGANISM: artificial sequence
<220> FEATURE:
<223> OTHER INFORMATION: Synthetic gene - codon optimized

<400> SEQUENCE: 65

| | |
|---|---|
| atgcctctgg ttgatatgcc tctgcgtgaa ctgctggctt atgaaggcat caacccaaaa | 60 |
| cctgctgact cgatcagta ttggaaccgc gctaaaaccg aaattgaggc tatcgatcct | 120 |
| gaagtaactc tggtagagtc ctccttccag tgctccttcg ctaactgcta ccatttctat | 180 |
| tatcgttccg cgggcaacgc taaaatccac gcgaagtacg tacagccaaa agcgggtgaa | 240 |
| aaaactccgg cagtcttcat gtttcacggc tacggtggtc gttccgctga atggtcctct | 300 |
| ctgctgaact acgttgctgc tggtttcagc gtcttctaca tggatgttcg tggccagggc | 360 |
| ggtacctccg aggacccggg tggcgtacgt ggtaacacct atcgtggtca tatcatccgt | 420 |
| ggcctggacg cgggtccgga tgcgctgttc taccgttccg tgttcctgga cacggtacag | 480 |
| ctggtgcgcg ctgcaaaaac cctgccgcac attgacaaga cccgtctgat ggccaccggc | 540 |
| tggagccagg gtggcgcact gactctggcg tgtgcagcgc tggtaccgga aatcaaacgt | 600 |
| ctggcgccgg tctacccgtt cctgtctgac tacaaacgcg tatggcagat ggacctggct | 660 |
| gttcgttcct acaaagaact ggcggactat ttccgctcct atgatccgca gcataaacgc | 720 |
| cacggtgaaa ttttcgaacg cctgggttat atcgacgttc agcacctggc tgatcgtatt | 780 |
| cagggcgacg ttctgatggg tgtgggcctg atggacaccg aatgcccgcc gagcacccaa | 840 |
| tttgcggcgt acaacaagat taaagctaag aaaagctacg aactgtaccc ggactttggt | 900 |
| catgagcatc tgcctggtat gaacgatcac atcttccgct tcttcacctc c | 951 |

<210> SEQ ID NO 66
<211> LENGTH: 52
<212> TYPE: DNA
<213> ORGANISM: artificial sequence
<220> FEATURE:
<223> OTHER INFORMATION: Primer

<400> SEQUENCE: 66

```
taactgcagt aaggaggaat aggacatggg tctgttcgat atgccactgc aa        52
```

<210> SEQ ID NO 67
<211> LENGTH: 36
<212> TYPE: DNA
<213> ORGANISM: artificial sequence
<220> FEATURE:
<223> OTHER INFORMATION: Primer

<400> SEQUENCE: 67

```
tgatctagat taagaataca gttccagcat gaactg                          36
```

<210> SEQ ID NO 68
<211> LENGTH: 997
<212> TYPE: DNA
<213> ORGANISM: artificial sequence
<220> FEATURE:
<223> OTHER INFORMATION: PCR amplification product

<400> SEQUENCE: 68

```
taactgcagt aaggaggaat aggacatggg tctgttcgat atgccactgc aaaaactgcg   60
tgaatatacc ggtaccaacc catgtcctga ggatttcgat gaatactggg atcgcgcact  120
ggacgaaatg cgtagcgttg atcctaaaat caagatgaag aagagctcct ttcaagttcc  180
gttcgcggaa tgttacgatc tgtatttac cggcgttcgt ggtgcccgca ttcacgcgaa   240
atacattcgt ccgaaaaccg aaggcaaaca cccggcgctg attcgcttcc atggttactc  300
cagcaactct ggtgattgga cgacaagct gaactacgtt gcggctggtt ttaccgtagt   360
agcgatggac gctcgtggcc agggtggcca atctcaggac gtcggcggtg ttaatggcaa  420
caccctgaac ggtcacatca tccgtggcct ggacgatgat gcagataaca tgctgttccg  480
tcatattttc ctggacaccg cgcagctggc tggtatcgtt atgaacatgc cggaaatcga  540
tgaggaccgc gtagctgtta tgggtccgtc ccagggcggc ggtctgtccc tggcgtgtgc  600
ggctctggaa cctaaaatcc gtaaagtagt gtccgaatat ccgttcctga gcgactacaa  660
gcgtgtgtgg gatctggatc tggccaaaaa tgcgtaccaa gaaatcactg actatttccg  720
tctgttcgac ccacgccacg aacgtgagaa cgaggttttt actaaactgg ttacattga   780
cgtaaagaac ctggcgaaac gtatcaaagg tgatgttctg atgtgcgtgg gcctgatgga  840
tcaggtctgc cgccgagca ccgtatttgc agcatacaac aacatccagt ccaagaagga  900
catcaaagtc tacccggact atggtcacga accgatgcgt ggcttcggtg acctggctat  960
gcagttcatg ctggaactgt attcttaatc tagatca                           997
```

<210> SEQ ID NO 69
<211> LENGTH: 960
<212> TYPE: DNA
<213> ORGANISM: artificial sequence
<220> FEATURE:
<223> OTHER INFORMATION: Synthetic gene - codon optimized

<400> SEQUENCE: 69

```
atgggtctgt tcgatatgcc actgcaaaaa ctgcgtgaat ataccggtac caacccatgt   60
cctgaggatt tcgatgaata ctgggatcgc gcactggacg aaatgcgtag cgttgatcct  120
aaaatcaaga tgaagaagag ctcctttcaa gttccgttcg cggaatgtta cgatctgtat  180
tttaccggcg ttcgtggtgc ccgcattcac gcgaaataca ttcgtccgaa aaccgaaggc  240
aaacacccgg cgctgattcg cttccatggt tactccagca actctggtga ttggaacgac  300
```

```
aagctgaact acgttgcggc tggttttacc gtagtagcga tggacgctcg tggccagggt    360
ggccaatctc aggacgtcgg cggtgttaat ggcaacaccc tgaacggtca catcatccgt    420
ggcctggacg atgatgcaga taacatgctg ttccgtcata ttttcctgga caccgcgcag    480
ctggctggta tcgttatgaa catgccggaa atcgatgagg accgcgtagc tgttatgggt    540
ccgtcccagg gcggcggtct gtccctggcg tgtgcggctc tggaacctaa aatccgtaaa    600
gtagtgtccg aatatccgtt cctgagcgac tacaagcgtg tgtgggatct ggatctggcc    660
aaaaatgcgt accaagaaat cactgactat ttccgtctgt tcgacccacg ccacgaacgt    720
gagaacgagg tttttactaa actgggttac attgacgtaa agaacctggc gaaacgtatc    780
aaaggtgatg ttctgatgtg cgtgggcctg atggatcagg tctgcccgcc gagcaccgta    840
tttgcagcat acaacaacat ccagtccaag aaggacatca agtctaccc ggactatggt    900
cacgaaccga tgcgtggctt cggtgacctg gctatgcagt tcatgctgga actgtattct    960
```

<210> SEQ ID NO 70
<211> LENGTH: 320
<212> TYPE: PRT
<213> ORGANISM: Thermoanaerobacterium saccharolyticum

<400> SEQUENCE: 70

```
Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asp Arg Ala Leu
            20                  25                  30

Asp Glu Met Arg Ser Val Asp Pro Lys Ile Lys Met Lys Lys Ser Ser
        35                  40                  45

Phe Gln Val Pro Phe Ala Glu Cys Tyr Asp Leu Tyr Phe Thr Gly Val
    50                  55                  60

Arg Gly Ala Arg Ile His Ala Lys Tyr Ile Arg Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Ala Arg Gly Gln Gly Gly Gln Ser Gln Asp Val Gly Gly
        115                 120                 125

Val Asn Gly Asn Thr Leu Asn Gly His Ile Ile Arg Gly Leu Asp Asp
    130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Ile Asp Glu Asp Arg Val
                165                 170                 175

Ala Val Met Gly Pro Ser Gln Gly Gly Gly Leu Ser Leu Ala Cys Ala
            180                 185                 190

Ala Leu Glu Pro Lys Ile Arg Lys Val Val Ser Glu Tyr Pro Phe Leu
        195                 200                 205

Ser Asp Tyr Lys Arg Val Trp Asp Leu Asp Leu Ala Leu Asn Ala Tyr
    210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270
```

```
Gln Val Cys Pro Pro Ser Thr Val Phe Ala Ala Tyr Asn Asn Ile Gln
            275                 280                 285

Ser Lys Lys Asp Ile Lys Val Tyr Pro Asp Tyr Gly His Glu Pro Met
        290                 295                 300

Arg Gly Phe Gly Asp Leu Ala Met Gln Phe Met Leu Glu Leu Tyr Ser
305                 310                 315                 320

<210> SEQ ID NO 71
<211> LENGTH: 49
<212> TYPE: DNA
<213> ORGANISM: artificial sequence
<220> FEATURE:
<223> OTHER INFORMATION: Primer

<400> SEQUENCE: 71
taactgcagt aaggaggaat aggacatggg gttcttcgac ctgcctctg             49

<210> SEQ ID NO 72
<211> LENGTH: 38
<212> TYPE: DNA
<213> ORGANISM: artificial sequence
<220> FEATURE:
<223> OTHER INFORMATION: Primer

<400> SEQUENCE: 72
tgatctagat tagcccttct caaacagttt ctttcagg                         38

<210> SEQ ID NO 73
<211> LENGTH: 1012
<212> TYPE: DNA
<213> ORGANISM: artificial sequence
<220> FEATURE:
<223> OTHER INFORMATION: PCR amplification product

<400> SEQUENCE: 73
taactgcagt aaggaggaat aggacatggc gttcttcgac ctgcctctgg aagaactgaa   60
gaaataccgt ccagagcgtt acgaagagaa ggacttcgac gagttctggg aggaaactct  120
ggcggagagc gaaaagtttc gctggaccc agtgttcgag cgtatggaat ctcacctgaa  180
aaccgtggag gcatatgacg ttactttttc tggttaccgt ggccagcgta tcaaaggctg  240
gctgctggtt ccgaaactgg aggaagaaaa actgccgtgc gtagttcagt acatcggtta  300
caacggtggc cgtggctttc gcacgattg gctgttctgg ccgtctatgg ctacatttg  360 cttcgtcatg gatactcgtg gtcagggttc cggctggctg aaaggcgata tccggatta  420 tccggagggc ccggtagacc cgcagtaccc tggcttcatg acgcgtggta ttctggatcc  480
gcgtacctat tactatcgcc gcgttttac cgatgcagtt cgtgccgtag aggccgcggc  540
ttctttccct caggttgacc aggagcgtat tgttatcgct ggtggctccc agggtggcgg  600
catcgccctg gcggtatctg cgctgagcaa gaaagctaag gcactgctgt gtgacgtccc  660
gttcctgtgt acttccgtc gcgctgttca gctggtagat acccatccgt acgcggagat  720
tactaacttc ctgaaaactc accgcgacaa agaagaaatc gttttccgca ccctgtccta  780
tttcgacggc gttaacttcg cggctcgtgc aaaaattccg gcactgttct ctgttggtct  840
gatggacaac atctgccctc cttctaccgt tttcgcggca tataactatt atgcgggtcc  900
gaaagaaatc cgtatctatc cgtacaacaa ccacgaaggc ggtggtagct ttcaggctgt  960
tgaacaagtg aaattcctga gaaaactgtt tgagaagggc taatctagat ca         1012

<210> SEQ ID NO 74
```

```
<211> LENGTH: 975
<212> TYPE: DNA
<213> ORGANISM: artificial sequence
<220> FEATURE:
<223> OTHER INFORMATION: Synthetic gene - codon optimized

<400> SEQUENCE: 74
atggcgttct tcgacctgcc tctggaagaa ctgaagaaat accgtccaga gcgttacgaa      60
gagaaggact tcgacgagtt ctgggaggaa actctggcgg agagcgaaaa gtttccgctg     120
gacccagtgt tcgagcgtat ggaatctcac ctgaaaaccg tggaggcata tgacgttact     180
ttttctggtt accgtggcca gcgtatcaaa ggctggctgc tggttccgaa actggaggaa     240
gaaaaactgc cgtgcgtagt tcagtacatc ggttacaacg gtggccgtgg ctttccgcac     300
gattggctgt tctggccgtc tatgggctac atttgcttcg tcatggatac tcgtggtcag     360
ggttccggct ggctgaaagg cgatactccg gattatccgg agggcccggt agacccgcag     420
taccctggct tcatgacgcg tggtattctg gatccgcgta cctattacta tcgccgcgtt     480
tttaccgatg cagttcgtgc cgtagaggcc gcggcttctt tccctcaggt tgaccaggag     540
cgtattgtta tcgctggtgg ctcccagggt ggcggcatcg ccctggcggt atctgcgctg     600
agcaagaaag ctaaggcact gctgtgtgac gtcccgttcc tgtgtcactt ccgtcgcgct     660
gttcagctgg tagataccca tccgtacgcg gagattacta acttcctgaa aactcaccgc     720
gacaaagaag aaatcgtttt ccgcaccctg tcctatttcg acggcgttaa cttcgcggct     780
cgtgcaaaaa ttccggcact gttctctgtt ggtctgatgg acaacatctg ccctccttct     840
accgttttcg cggcatataa ctattatgcg ggtccgaaag aaatccgtat ctatccgtac     900
aacaaccacg aaggcggtgg tagctttcag gctgttgaac aagtgaaatt cctgaagaaa     960
ctgtttgaga agggc                                                     975
```